United States Patent
Smith et al.

(10) Patent No.: US 9,266,873 B2
(45) Date of Patent: *Feb. 23, 2016

(54) PYRIDINE DERIVATIVES

(71) Applicant: Asana Biosciences, LLC, Bridgewater, NJ (US)

(72) Inventors: Roger Astbury Smith, Chester Springs, PA (US); Nicholas James Laping, West Chester, PA (US); Aranapakam M. Venkatesan, Malvern, PA (US); Raghava Reddy Kethiri, Noida (IN); Chandregowda Venkateshappa, Noida (IN); Bheemashankar Kulkarni, Noida (IN); Purushottam Dewang, Noida (IN); Rajendra Kristam, Noida (IN); Rajesh Devraj, Noida (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,949

(22) Filed: Aug. 18, 2014

(65) Prior Publication Data

US 2014/0378511 A1  Dec. 25, 2014

Related U.S. Application Data

(63) Continuation of application No. 13/632,006, filed on Sep. 30, 2012, now Pat. No. 8,809,372, which is a continuation of application No. PCT/US2012/057899, filed on Sep. 28, 2012.

(60) Provisional application No. 61/541,621, filed on Sep. 30, 2011.

(51) Int. Cl.
| | |
|---|---|
| *C07D 417/06* | (2006.01) |
| *C07D 417/14* | (2006.01) |
| *C07D 401/14* | (2006.01) |
| *C07D 401/06* | (2006.01) |
| *C07D 409/14* | (2006.01) |
| *C07D 413/06* | (2006.01) |
| *C07D 405/14* | (2006.01) |
| *C07D 213/30* | (2006.01) |
| *C07D 213/84* | (2006.01) |

(52) U.S. Cl.
CPC ............ *C07D 417/06* (2013.01); *C07D 213/30* (2013.01); *C07D 213/84* (2013.01); *C07D 401/06* (2013.01); *C07D 401/14* (2013.01); *C07D 405/14* (2013.01); *C07D 409/14* (2013.01); *C07D 413/06* (2013.01); *C07D 417/14* (2013.01)

(58) Field of Classification Search
CPC .................................................. C07D 417/06
See application file for complete search history.

(56) References Cited

U.S. PATENT DOCUMENTS

| | | | |
|---|---|---|---|
| 4,118,487 | A | 10/1978 | Regel et al. |
| 4,649,146 | A | 3/1987 | Takaya et al. |
| 4,661,603 | A | 4/1987 | Tsuruda et al. |
| 4,859,691 | A | 8/1989 | Bowman |
| 4,914,207 | A | 4/1990 | Nagel et al. |
| 5,068,237 | A | 11/1991 | Hobbs |
| 5,128,327 | A | 7/1992 | Chakravarty et al. |
| 5,137,879 | A | 8/1992 | Edie et al. |
| 5,389,635 | A | 2/1995 | Olson |
| 5,389,641 | A | 2/1995 | Naka et al. |
| 5,612,365 | A | 3/1997 | Heitsch et al. |
| 5,808,064 | A | 9/1998 | Chen et al. |
| 5,874,452 | A | 2/1999 | Anthony |
| 5,877,329 | A | 3/1999 | Chen et al. |
| 6,335,343 | B1 | 1/2002 | Lumma, Jr. et al. |
| 6,562,817 | B1 | 5/2003 | Tanimoto et al. |
| 6,653,306 | B1 | 11/2003 | Alexander et al. |
| 6,982,268 | B2 | 1/2006 | Xie et al. |
| 7,019,006 | B2 | 3/2006 | Cirillo et al. |
| 7,129,264 | B2 | 10/2006 | Smallheer et al. |

(Continued)

FOREIGN PATENT DOCUMENTS

| | | |
|---|---|---|
| EP | 0300688 A1 | 1/1989 |
| EP | 1070711 A2 | 1/2001 |
| EP | 2447261 A1 | 5/2012 |
| GB | 2276161 A | 9/1994 |
| GB | 2276162 A | 9/1994 |
| GB | 2427406 A | 12/2006 |
| WO | 9717070 A1 | 5/1997 |
| WO | 9748676 A1 | 12/1997 |
| WO | 9838177 A1 | 9/1998 |
| WO | 0076510 A1 | 12/2000 |

(Continued)

OTHER PUBLICATIONS

Berge et al., J. Pharm. Sci. 1977, vol. 66 1-18.
CAS registry No. 92164-39-1, entered STN database on 1962.
Devita, "Investigation of the 4-0-Aikylamine Substituent of Nonpeptide quinolone GnRH Receptor Antagonists", Bioorganic & Medicinal Chemistry Letters, 9:2621-2624 (1999).

(Continued)

*Primary Examiner* — Yong Chu
*Assistant Examiner* — Ana Z Muresan
(74) *Attorney, Agent, or Firm* — Lerner, David, Littenberg, Krumholz & Mentlik, LLP

(57) ABSTRACT

The present application provides novel pyridine compounds and pharmaceutically acceptable salts or prodrugs thereof. Also provided are methods for preparing these compounds. These compounds are useful in inhibiting CYP17 activity by administering a therapeutically effective amount of one or more of the compounds to a patient. By doing so, these compounds are effective in treating conditions associated with CYP17 activity. A variety of conditions can be treated using these compounds and include diseases which are characterized by abnormal cellular proliferation. In one embodiment, the disease is cancer, such as prostate cancer.

10 Claims, No Drawings

(56) References Cited

U.S. PATENT DOCUMENTS

| | | |
|---|---|---|
| 7,169,779 B2 | 1/2007 | Salituro et al. |
| 7,312,235 B2 | 12/2007 | Zhu et al. |
| 7,598,274 B2 | 10/2009 | Finsinger et al. |
| 2002/0151715 A1 | 10/2002 | Alanine et al. |
| 2003/0083269 A1 | 5/2003 | Brouillette et al. |
| 2003/0220380 A1 | 11/2003 | Dhanoa et al. |
| 2004/0006095 A1 | 1/2004 | Zhang et al. |
| 2004/0054173 A1 | 3/2004 | Kimura et al. |
| 2004/0167224 A1 | 8/2004 | Ozaki et al. |
| 2004/0248850 A1 | 12/2004 | Ernst et al. |
| 2004/0267017 A1 | 12/2004 | Bierer et al. |
| 2005/0014759 A1 | 1/2005 | Cai et al. |
| 2005/0054663 A1 | 3/2005 | Bennett et al. |
| 2005/0176710 A1 | 8/2005 | Schwink et al. |
| 2005/0203151 A1 | 9/2005 | Malecha et al. |
| 2005/0261236 A1 | 11/2005 | Okusa et al. |
| 2006/0004021 A1 | 1/2006 | Johansson et al. |
| 2006/0009472 A1 | 1/2006 | Wang et al. |
| 2006/0035893 A1 | 2/2006 | Jung et al. |
| 2006/0263411 A1 | 11/2006 | Tachdjian et al. |
| 2007/0082913 A1 | 4/2007 | Kim et al. |
| 2007/0123516 A1 | 5/2007 | Jung |
| 2007/0155724 A1 | 7/2007 | Moss et al. |
| 2007/0293507 A1 | 12/2007 | Baik et al. |
| 2008/0039511 A1 | 2/2008 | Takemura et al. |
| 2008/0194656 A1 | 8/2008 | Berwaer et al. |
| 2008/0262028 A1 | 10/2008 | Kallus et al. |
| 2009/0082370 A1 | 3/2009 | Thompson et al. |
| 2009/0093527 A1 | 4/2009 | Li et al. |
| 2009/0137592 A1 | 5/2009 | Scott et al. |
| 2009/0203699 A1 | 8/2009 | Barth et al. |
| 2009/0221586 A1 | 9/2009 | Okada et al. |
| 2009/0270359 A1 | 10/2009 | Ito et al. |
| 2009/0275592 A1 | 11/2009 | Zeng et al. |
| 2009/0318436 A1 | 12/2009 | Albrecht et al. |
| 2010/0022564 A1 | 1/2010 | Davies et al. |
| 2010/0075990 A1 | 3/2010 | Endres et al. |
| 2010/0130464 A1 | 5/2010 | Davies et al. |
| 2010/0166699 A1 | 7/2010 | Thompson et al. |
| 2010/0179059 A1 | 7/2010 | Renner et al. |
| 2010/0222326 A1 | 9/2010 | Kenda et al. |
| 2010/0234591 A1 | 9/2010 | Zhou et al. |
| 2010/0292258 A1 | 11/2010 | Ackermann et al. |
| 2011/0065129 A1 | 3/2011 | Lowe et al. |
| 2011/0068306 A1 | 3/2011 | Liao et al. |
| 2011/0263431 A1 | 10/2011 | Corsi et al. |
| 2011/0294836 A1 | 12/2011 | Song et al. |
| 2011/0301034 A1 | 12/2011 | Corsi et al. |
| 2012/0053180 A1 | 3/2012 | Kang et al. |
| 2012/0071524 A1 | 3/2012 | Lu et al. |
| 2012/0094980 A1 | 4/2012 | Gunzner et al. |
| 2012/0270871 A1 | 10/2012 | Wucherer-Plietker et al. |
| 2012/0270880 A1 | 10/2012 | Wucherer-Plietker et al. |
| 2013/0085164 A1 | 4/2013 | Smith et al. |

FOREIGN PATENT DOCUMENTS

| | | |
|---|---|---|
| WO | 0216324 A1 | 2/2002 |
| WO | 03086294 A2 | 10/2003 |
| WO | 2006036936 A2 | 4/2006 |
| WO | 2007011759 A2 | 1/2007 |
| WO | 2007038425 A2 | 4/2007 |
| WO | 2008065054 A1 | 6/2008 |
| WO | 2009058944 A2 | 5/2009 |
| WO | 2010139966 A1 | 12/2010 |
| WO | 2011011872 A1 | 2/2011 |
| WO | 2011076316 A1 | 6/2011 |
| WO | 2011076327 A1 | 6/2011 |
| WO | 2011082098 A1 | 7/2011 |
| WO | 2011153192 A2 | 12/2011 |
| WO | 2012010567 A1 | 1/2012 |
| WO | 2012044650 A1 | 4/2012 |
| WO | 2012051036 A1 | 4/2012 |
| WO | 2012052540 A1 | 4/2012 |
| WO | 2012112969 A1 | 8/2012 |

OTHER PUBLICATIONS

Effenberge et al. Synthesis (2000), (9), 1229-1236.
Hartmann, "Inhibition of CYP17, a new strategy for the treatment of prostate cancer", Archiv Der Pharmazie, 335 ( 4 ): 119-128 (Apr. 2002).
Hille, "First selective CYP11 B1 inhibitors for the treatment of cortisol-dependent diseases", ACS Medicinal Chemistry Letters, 2:2-6 (2011; e-publication: Oct. 22, 2010).
Hu et al. J. Med. Chem., 2010, 53, 5749-5758.
Hu, "Synthesis, biological evaluation and molecular modeling studies of methyleneimidazole substituted biaryls as inhibitors of human 17a-hydroxylase-17,20-lyase (CYP17). Part II: Core rigidification and influence of substituents at the methylene bridge", Bioorganic & Medicinal Chemistry, 16:7715-7727 (2008; epublication: Jul. 9, 2008).
International Preliminary Report on Patentability (Chapter I of the Patent Cooperation Treaty) issued for International Application No. PCT/US2012/057899 dated Apr. 1, 2014.
International Search Report dated Jan. 9, 2013 issued in corresponding International Patent Application No. PCT/US0212/057899.
Jagusch, "Synthesis, biological evaluation and molecular modeling studies of methyleneimidazole substituted biaryls as inhibitors of human 17a-hydroxylase-17,20-lyase (CYP17). Part 1: Heterocyclic modifications of the core structure", Bioorganic & Medicinal Chemistry, 16:1992-2010 (2008: e-publication: Nov. 4, 2007).
Laping, "EN3356, a novel CYP17 inhibitor for the treatment of castration resistant prostate cancer", Poster presented at the AACR-NCI-EORTC symposium, Boston, MA, Oct. 19-23, 2013 (poster presented: Oct. 22, 2013).
Liu, "Acid Solution is a Suitable Medium for Introducing QX-314 into Nociceptors through TRPV1 Channels to Produce Sensory-Specific Analgesic Effects", Plos ONE, 6(12):e29395 (Dec. 28, 2011).
Marxer et al. Helvetica Chimica Acta (1974), 57(7) 1988-2000.
Medarde, "Heterolignanolides: antitumor activity of furyl-, thienyl-, and pyridyl analogs of lignanolides", Archiv Der Pharmazie, 328(5):403-407 (1995).
Meyer, "Synthesis and Stereochemistry of Indolizidine and Pyrrolizidine Methosalts", Journal of the American Chemical Society, 86(16):3343-3350 (1964).
Neidle S. Cancer Drug Design and Discovery, ed. (Elsevier/Academic Press, 2008), 427-431.
Reid, "CYP17 inhibition as a hormonal strategy for prostate cancer", Nature Clin. Prac., 5(11):610 (Nov. 2008).
Yap, "Targeting CYP17: established and novel approaches in prostate cancer", Current Opinion in Pharmacology, 8:449-457 (2008; e-publication: Jul. 28, 2008).
Vasaitis, "CYP17 inhibitors for prostate cancer therapy", Journal of Steroid Biochemistry & Molecular Biology, 125:23-31 (May 2011; e-publication: Nov. 17, 2010).
Alexander et al., "(Acyloxy)alkyl Carbamate Prodrugs of Norfloxacin", J. Med. Chem., 1991, 34, 78-81.
Alexander et al., "(Acyloxy)alkyl Carbamates as Novel Bioreversible Prodrugs for Amines: Increased Permeation through Biological Membranes", J. Med. Chem., 1988, 31, 318-322.
Alexander et al., "Investigation of (Oxodioxolenyl)methyl Carbamates as Nonchiral Bioreversible Prodrug Moieties for Chiral Amines", J. Med. Chem., 1996, 39, 480-486.
Beaumont et al., "Design of ester prodrugs to enhance oral absorption of poorly permeable compounds: Challenges to the discovery scientist", Current Drug Metabolism, 2003, 4, 461-485.
Ettmayer et al., "Lessons learned from marketed and investigational prodrugs", Journal of Medicinal Chemistry, vol. 47, No. 10, pp. 2393-2404, May 6, 2004.
Li et al., "Synthesis of (alkoxycarbonyloxy) methyl, (acyloxy) methyl and (oxodioxolenyl) methyl carbamates as bioreversible prodrug moieties for amines", Bioorganic & Medical Chemistry Letters, vol. 7, No. 22, pp. 2909-2912, 1997.

(56) References Cited

OTHER PUBLICATIONS

Polshettiwar et al., "Greener and rapid access to bio-active heterocycles: one-pot solvent-free synthesis of 1,3,4-oxadiazoles and 1,3,4-thiadiazoles", Science Direct, Tetrahedron Letters 49, 2008, pp. 879-883.

Rautio et al., "Prodrugs: design and clinical applications", Nature Reviews/Drug Discovery, Mar. 2008, vol. 7, pp. 255-270.

Sanders et al., "Metal-free sequential [3+2]-dipolar cycloadditions using cyclooctynes and 1,3-dipoles of different reactivity", Journal of the American Chemical Society, 2011, 133, pp. 949-957.

Simplicio et al., "Prodrugs for Amines", Molecules 2008, 13, 519-547.

PYRIDINE DERIVATIVES

CROSS-REFERENCE TO RELATED APPLICATIONS

The present application is a continuation of U.S. patent application Ser. No. 13/632,006, filed Sep. 30, 2012, which claims priority from International Application No. PCT/US2012/057899, filed Sep. 28, 2012, which claims the benefit of the filing date of U.S. Provisional Patent Application No. 61/541,621, filed on Sep. 30, 2011, all of which are incorporated herein by reference.

BACKGROUND

Prostate cancer is the most common malignancy for older men and is a major cause of death for that population. Until recently, it was believed that reduction of testosterone was a key component in treating patients diagnosed with prostate cancer. However, a large number of patients having prostate cancer do not respond to reduction of testosterone levels instigated by luteinizing hormone releasing hormone (LHRH) agonists and were thereby dubbed as having "hormone resistant" cancer. Only half of these patients having "hormone-resistant" prostate cancer respond to hormonal treatments.

It is currently recognized that LHRH agonists or antagonists do not completely reduce circulating testosterone levels due to sources other than the testes that can synthesize testosterone, including the adrenal gland and the prostate tumors themselves. The cytochrome P450 (CYP) enzymes include a large family of highly conserved enzymes, including CYP17, that are involved in the synthesis of cholesterol and other bioactive steroids. The fact that these enzymes are involved in steroid hormone biosynthesis has led to recent findings that castration-resistant prostate cancer in men and certain breast cancers in women are responsive to CYP17 inhibition.

CYP17 is a key enzyme in the production of androgenic steroids in many tissues, including prostate tumors, and catalyzes the 17α-hydroxylase reaction and 17,20-lyase reaction of both progesterone and pregnenolone. Inhibition of CYP17 results in reducing the levels of dehydroepiandrostenedione (DHEA) and androstenedione, which are weak androgens and precursors that are subsequently converted to testosterone and dihydrotestosterone by other enzymes.

Designing inhibitors of CYP17 is problematic for several reasons. First, there is limited information regarding the structure of this enzyme. Second, human CYP17 is not available from natural sources, thereby requiring its recombinant generation. Ketoconazole has been used to inhibit CYP17, but is not very potent and is non-selective since it inhibits other CYP enzymes. Other CYP17 inhibitors have been reported, and the steroidal CYP17 inhibitor Zytiga™ (abiraterone acetate) was recently approved by the U.S. Food and Drug Administration (FDA) for use in combination with prednisone for the treatment of patients with metastatic castration-resistant prostate cancer (CRPC) who have received prior chemotherapy containing docetaxel. Most CYP17 inhibitors, however, including both steroidal compounds such as abiraterone and non-steroidal compounds, have limited selectivity for CYP17, short in vivo half-lives, and/or poor bioavailability.

What is needed are alternative medications for treating prostate and other cancers that function by inhibiting CYP17.

SUMMARY OF THE INVENTION

In one aspect, the present invention provides a compound of formula (I), wherein A, B and $R^1$ are defined herein, or a pharmaceutically acceptable salt or prodrug thereof.

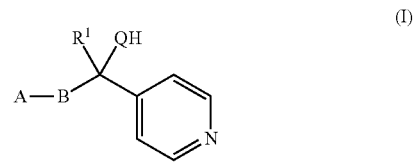

(I)

In another aspect, the invention provides a pharmaceutical composition containing a compound of formula (I) and a pharmaceutically acceptable carrier.

In a further aspect, the invention provides a method for regulating CYP17 by administering a therapeutically effective amount of a compound of formula (I) to a patient in need thereof.

In another aspect, the invention provides a method for inhibiting CYP17 activity by administering a therapeutically effective amount of a compound of formula (I) to a patient in need thereof.

In yet another aspect, methods for treating conditions treatable by inhibiting CYP17 activity are provided and include administering a compound of formula (I) to a patient in need thereof.

In a further aspect, methods for treating cancer, such as prostate cancer, are provided and include administering a compound of formula (I) to a patient in need thereof.

In a still further aspect, methods for reducing testosterone production in a patient by administering a therapeutically effective amount of a compound of formula (I) to a patient in need thereof.

Other aspects and advantages of the invention will be readily apparent from the following detailed description of the invention.

DETAILED DESCRIPTION OF THE INVENTION

The invention provides compounds and pharmaceutical composition thereof, which are useful for regulating CYP17 activity and are, therefore, capable of treating conditions associated with abnormal cell proliferation. Specifically, the inventors found that it was the linking of the pyridine ring to a phenyl-heteroaryl or bi-heteroaryl group via a hydroxymethylene fragment or an aminomethylene fragment which provided compounds that selectively inhibit CYP17.

The compounds discussed herein are encompassed by the following structure of formula (I):

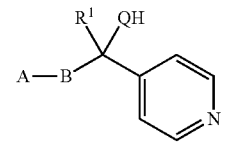

In this structure, A is optionally substituted phenyl or optionally substituted heteroaryl.

a. In one embodiment, A is

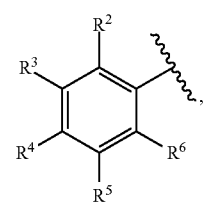

wherein $R^2$, $R^3$, $R^4$, $R^5$, and $R^6$ are, independently, selected from among H, halogen, OH, CN, optionally substituted $C_1$ to $C_6$ alkyl, $C_1$ to $C_6$ alkoxy, $H_2NC(O)$—, ($C_1$ to $C_4$ alkyl)-NHC(O)—, ($C_1$ to $C_4$ alkyl)$_2$NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl). 3, 4 or 5 of $R^2$, $R^3$, $R^4$, $R^5$, and $R^6$ are hydrogen.

b. In another embodiment, A is

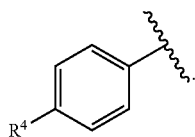

c. In a further embodiment, A is

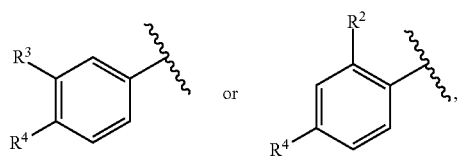

d. In another embodiment, A is optionally substituted pyridine.

e. In still a further embodiment, A is

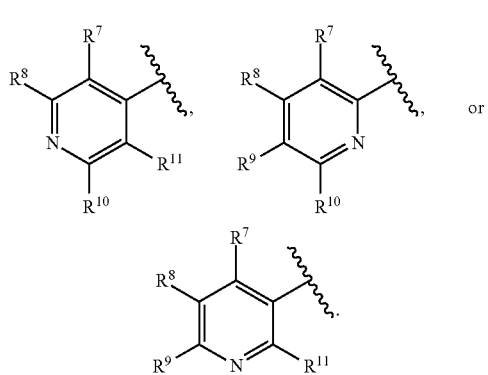

In these structures, $R^7$, $R^8$, $R^9$, $R^{10}$, and $R^{11}$ are, independently, selected from among H, halogen, OH, CN, optionally substituted $C_1$ to $C_6$ alkyl, $C_1$ to $C_6$ alkoxy, $H_2NC(O)$—, ($C_1$ to $C_4$ alkyl)-NHC(O)—, ($C_1$ to $C_4$ alkyl)$_2$NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl). 2, 3 or 4 of $R^7$, $R^8$, $R^9$, $R^{10}$, and $R^{11}$ are hydrogen.

f. In still another embodiment, A is

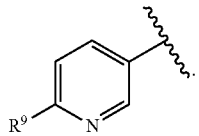

g. In yet a further embodiment, A is optionally substituted pyridone.

h. In another embodiment, A is

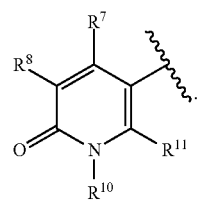

In this structure, $R^7$, $R^8$, $R^{10}$ and $R^{11}$ are, independently, selected from among H, halogen, OH, CN, optionally substituted $C_1$ to $C_6$ alkyl, $C_1$ to $C_6$ alkoxy, $H_2NC(O)$—, ($C_1$ to $C_4$ alkyl)-NHC(O)—, ($C_1$ to $C_4$ alkyl)$_2$NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl).

i. In still a further embodiment, A is

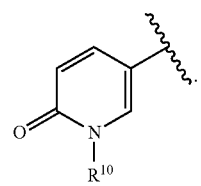

In one example, $R^{10}$ is $C_1$ to $C_6$ alkyl.

j. In yet another embodiment, A is

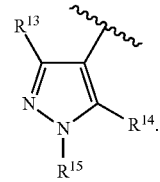

In this structure, $R^{13}$ and $R^{14}$ are, independently, selected from among H, halogen, OH, CN, optionally substituted $C_1$ to $C_6$ alkyl, $C_1$ to $C_6$ alkoxy, $H_2NC(O)$—, ($C_1$ to $C_4$ alkyl)-NHC(O)—, ($C_1$ to $C_4$ alkyl)$_2$NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl); and $R^{15}$ is H or $C_1$ to $C_6$ alkyl.

k. In a further embodiment, A is

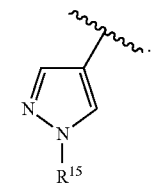

In one example, $R^{15}$ is H.

In formula (I), B is an optionally substituted heteroaryl.

i. In one embodiment, B is an optionally substituted pyridine.

ii. In another embodiment, B is

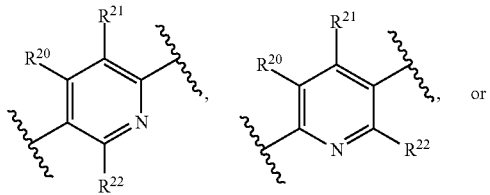

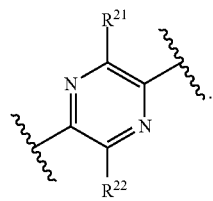

In these structures for B, $R^{20}$, $R^{21}$ and $R^{22}$ are independently selected from among H, F, Cl, $CH_3$, $CF_3$, and CN.

iii. In a further embodiment, B is

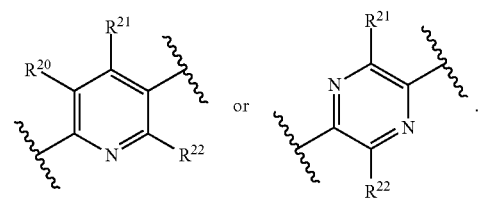

In one example, $R^{20}$, $R^{21}$, and $R^{22}$ are H.

iv. In yet another embodiment, B is

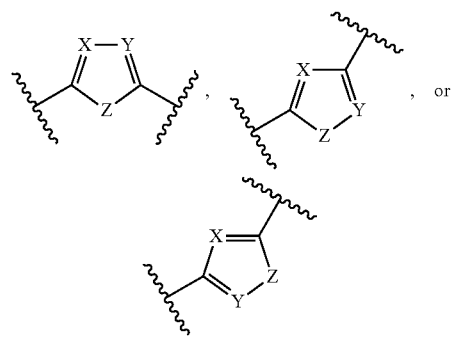

In these structures, X and Y are independently selected from among $CR^{23}$ and N; Z is $NR^{24}$, O or S. Each $R^{23}$ is, independently, H, F, Cl, $CH_3$, $CF_3$ or CN and $R^{24}$ is H or $C_1$ to $C_4$ alkyl.

v. In still a further embodiment, B is

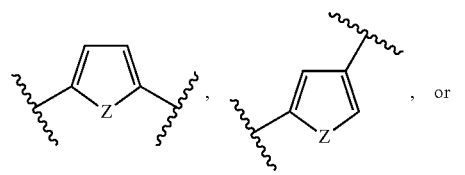

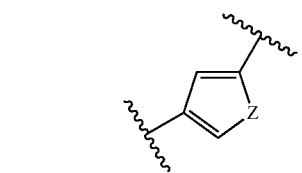

vi. In yet another embodiment, B is

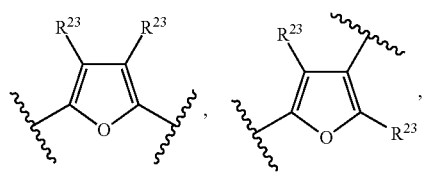

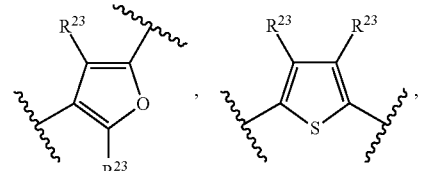

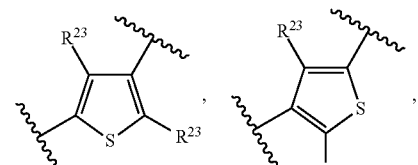

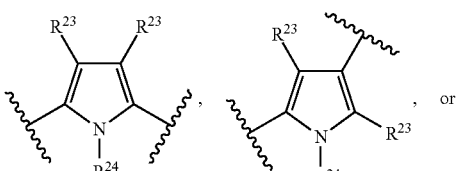

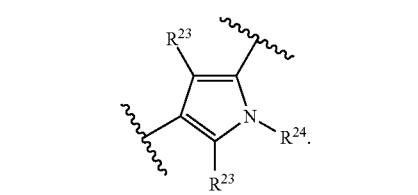

vii. In a further embodiment, B is

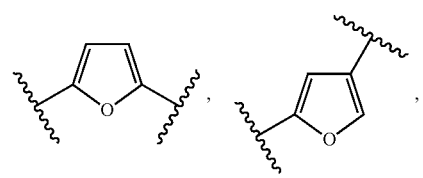

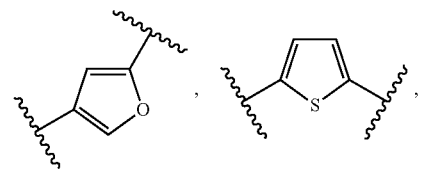

viii. In yet another embodiment, B is
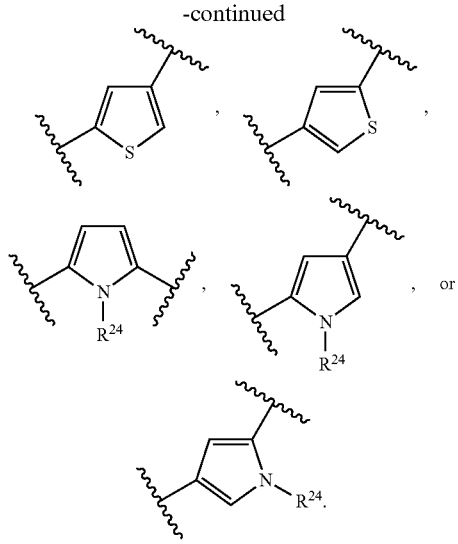
ix. In still a further embodiment, B is
x. In still another embodiment, B is
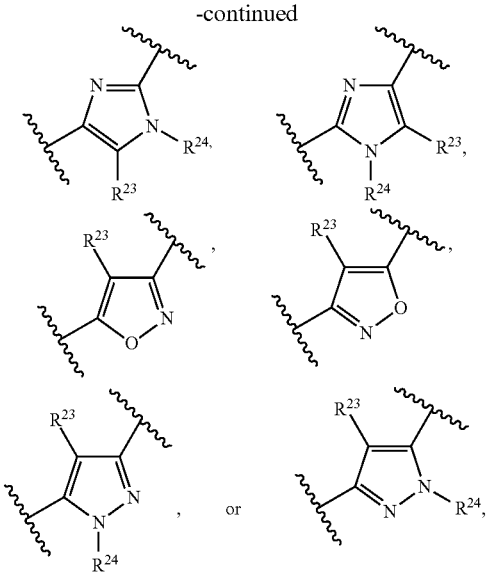
xi. In yet a further embodiment, B is In another embodiment, B is

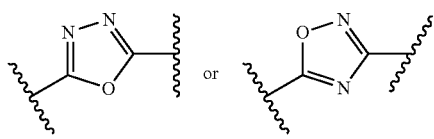

or.

In the structure of formula (I), $R^1$ is H or $C_1$ to $C_4$ alkyl. In another embodiment, $R^1$ is two or three methylene fragments, which are joined to a carbon atom at the 3-position of the pyridine ring. Further, Q is O or NH.

In another embodiment, the compounds discussed herein are encompassed by the following structure of formula (I-A), wherein A, B, and $R^1$ are defined herein.

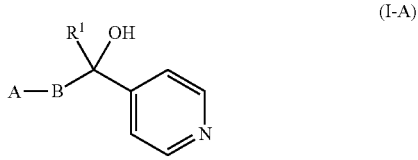
(I-A)

In a further embodiment, the compounds discussed herein are encompassed by the following structure of formula (I-B), wherein A, B, and $R^1$ are defined herein.

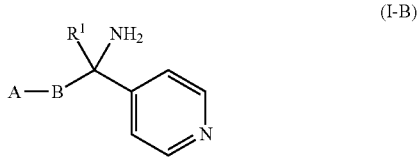
(I-B)

In still another embodiment, the compounds discussed herein are encompassed by the following structure of formula (I-D), wherein A, B, and $R^1$ are defined herein and $R^Z$ is $C_1$ to $C_6$ alkyl.

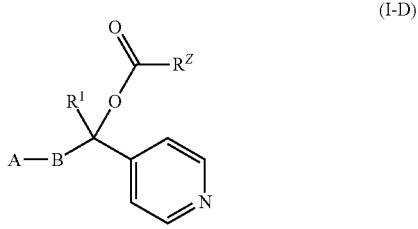
(I-D)

In yet a further embodiment, the compounds discussed herein are encompassed by the following structure of formula (I-E), wherein A, B, and $R^1$ are defined herein and $R^Z$ is $C_1$ to $C_6$ alkyl.

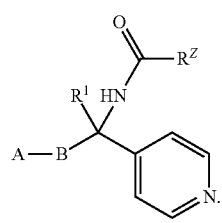

One of skill in the art would readily be able to select the A, B, and $R^1$ groups with the knowledge that stable chemical bonds must be formed. Specifically, one of skill in the art would readily understand which chemical bonds could/could not be formed and how to tailor the reactions in view thereof. The term "stable" as used in this context, refers to a resultant molecule that can be prepared and isolated without degradation.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds of the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. The structures that are represented here are drawn without any stereochemical indication. It is implied that when a chiral center is present in a molecule, it represent both enantiomers. Terms not defined herein have the meaning commonly attributed to them by those skilled in the art.

"Alkyl" refers to a hydrocarbon chain that may be straight or branched, or to a hydrocarbon group that consists of or contains a cyclic alkyl radical. In one embodiment, an alkyl contains 1 to 8 (inclusive) carbon atoms or integers or ranges there between. In another embodiment, an alkyl contains 1 to 7 (inclusive) carbon atoms or ranges there between. In a further embodiment, an alkyl contains 1 to 6 (inclusive) carbon atoms. In yet another embodiment, an alkyl contains 1 to 5 (inclusive) carbon atoms. In still a further embodiment, an alkyl contains 1 to 4 (inclusive) carbon atoms. Examples of alkyl groups that are hydrocarbon chains include, but are not limited to, methyl, ethyl, propyl, butyl, pentyl, hexyl, and heptyl, where all isomers of these examples are contemplated. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl.

"Optionally substituted alkyl" refers to an alkyl group, as defined above, that is unsubstituted or substituted with one or more F, one or two Cl, one or two OH, one amino group, one (alkyl)amino group (i.e., alkyl-NH—), one (dialkyl)amino group (i.e., (alkyl)$_2$N—), one or two alkoxy groups, or one cyano group, or any combination of these substituents. "Substituted" means that one or more of the alkyl group's hydrogen atoms is replaced with a substituent group as listed above.

"Alkoxy" refers to the group R—O— where R is an alkyl group, as defined above. Exemplary $C_1$-$C_6$ alkoxy groups include but are not limited to methoxy, ethoxy, n-propoxy, i-propoxy, n-butoxy and t-butoxy.

"(Alkoxy)carbonyl-" refers to the group alkyl-O—C(O)—. Exemplary ($C_1$-$C_6$ alkoxy)carbonyl groups include, but are not limited to, methoxy, ethoxy, n-propoxy, 1-propoxy, n-butoxy and t-butoxy.

"(Alkyl)amido-" refers to the group —C(O)NH-alkyl. Representative examples of ($C_1$-$C_6$ alkyl)amido include, but are not limited to, —C(O)NHCH$_3$, —C(O)NHCH$_2$CH$_3$, —C(O)NHCH$_2$CH$_2$CH$_3$, —C(O)NHCH$_2$CH$_2$CH$_2$CH$_3$, —C(O)NHCH$_2$CH$_2$CH$_2$CH$_2$CH$_3$, —C(O)NHCH(CH$_3$)$_2$, —C(O)NHCH$_2$CH(CH$_3$)$_2$, —C(O)NHCH(CH$_3$)CH$_2$CH$_3$, —C(O)NH—C(CH$_3$)$_3$ and —C(O)NHCH$_2$C(CH$_3$)$_3$.

"Di(alkyl)amido-" refers to a —C(O)—N group in which the nitrogen atom of the group is attached, independently, to alkyl groups, as defined above. Each alkyl group can be independently selected. Representative examples of ($C_1$-$C_6$ alkyl)$_2$amido include, but are not limited to, —C(O)N(CH$_3$)$_2$, —C(O)N(CH$_2$CH$_3$)$_2$, —C(O)N(CH$_2$CH$_2$CH$_3$)$_2$, —C(O)N(CH$_2$CH$_2$CH$_2$CH$_3$)$_2$, —C(O)N(CH$_2$CH$_2$CH$_2$CH$_2$CH$_3$)$_2$, —C(O)N(CH$_3$)(CH$_2$CH$_3$), and —C(O)N(CH$_2$CH$_3$)(CH$_2$CH$_2$CH$_3$)$_2$.

"Alkylsulfonyl" refers to an alkyl-S(O)$_2$— group. Representative examples of ($C_1$-$C_6$ alkyl)sulfonyl group are, but are not limited to, CH$_3$S(O)$_2$— and CH$_3$CH$_2$S(O)$_2$—.

"(Alkyl)amino-" refers to an alkyl-NH— group. Representative examples of ($C_1$-$C_6$ alkyl)amino group are, but are not limited to, CH$_3$NH—, CH$_3$CH$_2$NH—, CH$_3$CH$_2$CH$_2$NH—, CH$_3$CH$_2$CH$_2$CH$_2$NH—, (CH$_3$)$_2$CHNH—, (CH$_3$)$_2$CHCH$_2$NH—, CH$_3$CH$_2$CH(CH$_3$)NH— and (CH$_3$)$_3$CNH—.

"(Dialkyl)amino-" refers to an (alkyl)$_2$N— group, wherein the two alkyl groups are independently selected. Representative examples of di($C_1$-$C_6$ alkyl)amino include, but are not limited to (CH$_3$)$_2$N—, (CH$_3$CH$_2$)$_2$N—, (CH$_3$CH$_2$CH$_2$)$_2$N—, (CH$_3$)(CH$_2$CH$_3$)N—, (CH$_3$)(CH$_2$CH$_2$CH$_3$)N—, and (CH$_3$CH$_2$)(CH$_2$CH$_2$CH$_3$)N—.

"Alkylcarboxy-" refers to an alkyl group, defined above that is attached to the parent structure through the carbon atom of a carboxy (C(O)—O—) functionality. Examples of ($C_1$-$C_6$ alkyl)carboxy include acetoxy, propionoxy, propylcarboxy, and isopentylcarboxy.

"(Alkyl)carboxamido-" refers to a —NHC(O)-alkyl-group in which the carbonyl carbon atoms of the group is attached to an alkyl group. Representative examples of ($C_1$-$C_6$ alkyl)carboxamido include, but are not limited to, —NHC(O)CH$_3$, —N(CH$_3$)C(O)CH$_3$, —N(CH$_3$)C(O)CH$_2$CH$_3$, —N(CH$_3$)C(O)CH$_2$CH$_2$CH$_3$, —N(CH$_3$)C(O)CH$_2$CH$_2$CH$_2$CH$_3$, —N(CH$_2$CH$_3$)C(O)CH$_2$CH$_2$CH$_2$CH$_3$, N(CH$_2$CH$_3$)C(O)CH(CH$_3$)$_2$, —N(CH$_2$CH$_3$)C(O)CH$_2$CH(CH$_3$)$_2$, —N(CH$_2$CH$_3$)C(O)CH(CH$_3$)CH$_2$CH$_3$, and —N(CH$_2$CH$_3$)C(O)C(CH$_3$)$_3$.

"Optionally substituted phenyl" refers to a phenyl group that can be unsubstituted or substituted with one or more of optionally substituted alkyl, halogen, OH, NH$_2$, alkylamino-, di(alkyl)amino-, cyano, COOH, (alkoxy)carbonyl-, alkylcarboxy-, (alkyl)carboxamido-, alkylsulfonyl, —C(O)NH$_2$, (alkyl)amido-, di(alkyl)amido-, NO$_2$, or alkoxy.

"Halo" or "halogen" refers to F, Cl, Br and I.

"Heteroaryl" refers to a monocyclic 5-membered or 6-membered aromatic ring system containing at least one ring atom selected from the heteroatoms oxygen, sulfur and nitrogen. Examples of heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, and pyridone, including 2-pyridone.

"Optionally substituted heteroaryl" refers to a heteroaryl group, as defined above, that is unsubstituted or substituted with one or more of optionally substituted alkyl, F, Cl, OH, NH$_2$, alkylamino-, di(alkyl)amino-, cyano, COOH, (alkoxy)carbonyl-, alkylcarboxy-, (alkyl)carboxamido-, alkylsulfonyl, —C(O)NH$_2$, (alkyl)amido-, di(alkyl)amido-, NO$_2$, or alkoxy.

A "subject" is a mammal, e.g., a human, mouse, rat, guinea pig, dog, cat, horse, cow, pig, or non-human primate, such as a monkey, chimpanzee, baboon or gorilla.

Representative "pharmaceutically acceptable salts" include but are not limited to, e.g., water-soluble and water-insoluble salts, including salts of acids. Examples of acids which can form salts with the compounds discussed herein include, without limitation, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic.

In a further embodiment, a compound of the invention may be a solvate. As used herein, a solvate does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

In a further embodiment, a compound of the invention may be a prodrug of a compound of formula (I). Prodrugs of compounds of formula (I) may be prepared and used as a means to modulate the pharmacokinetic properties, using various methods known to those skilled in the art. See, e.g., Rautio, Nature Reviews Drug Discovery, 7:255-270 (2008) and Ettmayer, J. Med. Chem., 47:2393-2404 (2004), which are hereby incorporated by reference. In the case of drugs containing a hydroxy moiety, acetyl and other ester analogs are contemplated for use as prodrugs. See, e.g., Beaumont, Current Drug Metabolism, 4:461-485 (2003), which is hereby incorporated by reference. In the case of drugs containing an amine moiety, prodrugs containing amides and carbamates are contemplated. See, e.g., Simplício, Molecules, 13:519-547 (2008), which is hereby incorporated by reference. As specific examples, (alkoxycarbonyloxy)alkyl carbamates, (acyloxy)alkyl carbamates, and (oxodioxolenyl) alkyl carbamates may be utilized as effective prodrug strategies for amines. See, e.g., Li, Bioorg. Med. Chem. Lett., 7:2909-2912 (1997); Alexander, J. Med. Chem., 34:78-81 (1991); Alexander, J. Med. Chem., 31:318-322 (1988); and Alexander, J. Med. Chem., 39:480-486 (1996), all of which are incorporated by reference herein.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

Processes for Preparing the Compounds

Methods useful for making the compounds of formula (I) are set forth in the Examples below and generalized in the schemes. One of skill in the art will recognize that the schemes can be adapted to produce the other compounds of formula (I) and pharmaceutically acceptable salts or prodrugs of compounds of formula (I).

In the following reactions described to prepare compounds described herein, it can be necessary to protect reactive functional groups, for example OH, amino, imino, thio or carboxy groups, where these are desired in the final product, to avoid their unwanted participation in the reactions. Conventional protecting groups can be used in accordance with standard practices, for example, see T. W. Green and P. G. M. Wuts in "Protective Groups in Organic Chemistry", John Wiley &Sons, 1991.

The following methods outline the synthesis of the compounds of formula (I). The following examples are presented to illustrate certain embodiments of the present invention, but should not be construed as limiting the scope of the invention.

Scheme 1

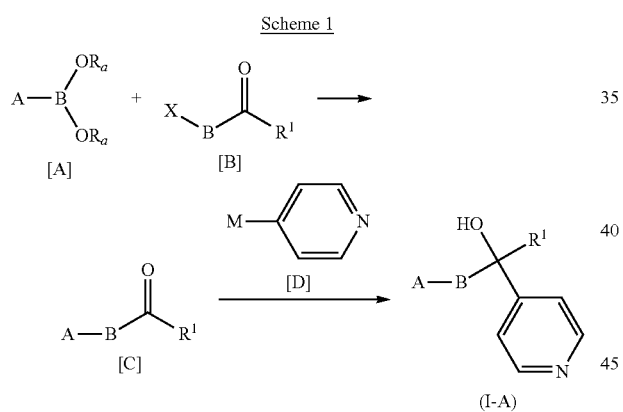

Scheme 1 depicts one synthesis method to prepare compounds of formula (I-A). In one embodiment, a boronic acid ($R_a$=H) or boronate ester ($R_a$=alkyl) derivative of fragment A [A] is first coupled to a heteroaryl halide [B], wherein X=halogen. In a further embodiment, [B] is a heteroaryl triflate, wherein X is trifluoromethylsulfonate. This reaction may be performed using, e.g., a boronic acid pinacol ester derivative [A], in the presence of a weak base and a palladium catalyst. In one embodiment, the weak base is KOAc or $Na_2CO_3$. In another embodiment, the palladium catalyst is Pd(PPh$_3$)$_4$, Pd(dppf)Cl$_2$.DCM or Pd(dppf)Cl$_2$. In a further embodiment, the reaction is performed in a solvent such as toluene/ethanol, 1,4-dioxane or DMF. In yet another embodiment, the reaction is performed at elevated temperatures up to the reflux temperature of the solvent. The intermediate [C] is then reacted with the 4-anion of pyridine, i.e., M-pyridine shown in Scheme 1, wherein M is a metal or metalloid moiety such as Li, Mg—Br or Mg—Cl. In one embodiment, the 4-anion of pyridine is pyridin-4-yl lithium, which may be generated from 4-iodopyridine or 4-bromo-pyridine upon treatment with an alkyl metal reagent such as n-butyl lithium.

Scheme 2

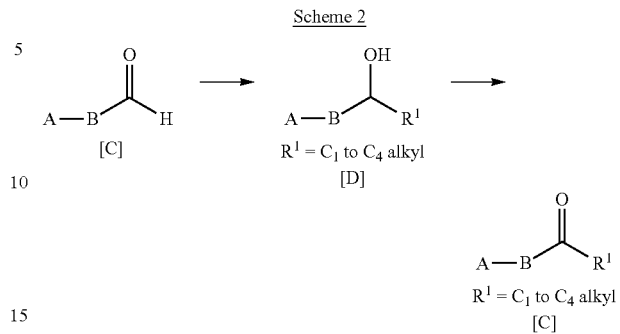

Scheme 2 provides a method wherein compounds of formula (I) can be prepared, by first preparing aldehyde intermediate [C] by the method indicated in Scheme 1, followed by a two-step conversion to an alkyl ketone [C] ($R^1$=C$_1$ to C$_4$ alkyl). Ketone [C] ($R^1$=C$_1$ to C$_4$ alkyl) is then converted to compounds of formula (I) by the method described in Scheme 1. In one embodiment, aldehyde [C] is reacted with an alkyl metal reagent to produce hydroxy intermediate [D]. In another embodiment, the alkyl metal reagent is an alkyl lithium or alkyl Grignard reagent (alkyl-MgX). Intermediate [D] is oxidized with an oxidizing agent to produce the alkyl ketone [C] ($R^1$=C$_1$ to C$_4$ alkyl). In one embodiment, the oxidizing agent is Dess-Martin periodinane. In a further embodiment, the oxidizing agent is MnO$_2$ or PCC (pyridinium chlorochromate). Ketone [C] (equivalent to intermediate [C] in Scheme 1) may then be converted to compounds of formula (I) by the method described herein such as in Scheme 1.

Scheme 2A

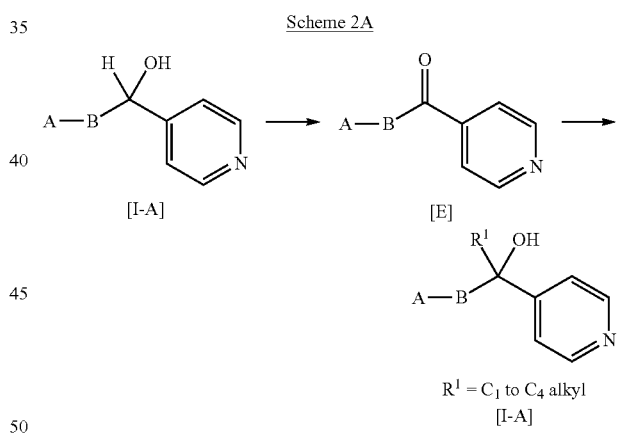

Scheme 2A applies the two-step methodology as described in Scheme 2 to convert compounds of Formula (I-A), where $R^1$=H, via the ketone intermediate [E], into compounds of formula (I), where $R^1$=C$_1$ to C$_4$ alkyl.

Scheme 3

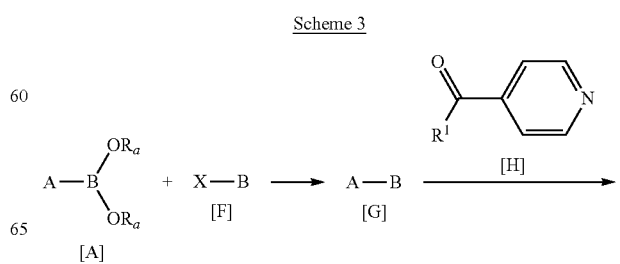

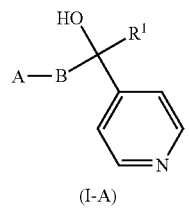

Scheme 3 depicts a further method for the preparation of compounds of formula (I-A). In one embodiment, a boronic acid ($R_a$=H) or boronate ester ($R_a$=alkyl) derivative of fragment A [A] is first coupled to a heteroaryl halide [F], where X=halogen, to produce intermediate [G]. In a further embodiment, [F] is a heteroaryl triflate, wherein X is trifluoromethylsulfonate. This coupling reaction may be performed using, e.g., a boronic acid pinacol ester derivative [A], a weak base, and a palladium catalyst. In one embodiment, the weak base is KOAc or $Na_2CO_3$. In another embodiment, the palladium catalyst is $Pd(PPh_3)_4$, $Pd(dppf)Cl_2 \cdot DCM$ or $Pd(dppf)Cl_2$. Desirably the reaction is performed in a solvent such as toluene/ethanol, 1,4-dioxane or DMF. The reaction may be performed at elevated temperatures up to the reflux temperature of the solvent. An anionic species of [G] is then generated from [G] by treatment with a strongly basic reagent. In one embodiment, the strongly basic reagent is n-butyl lithium or lithium diisopropylamide (LDA). This anionic species is then reacted with a pyridin-4-yl alkyl ketone [H] to form compounds of formula (I-A).

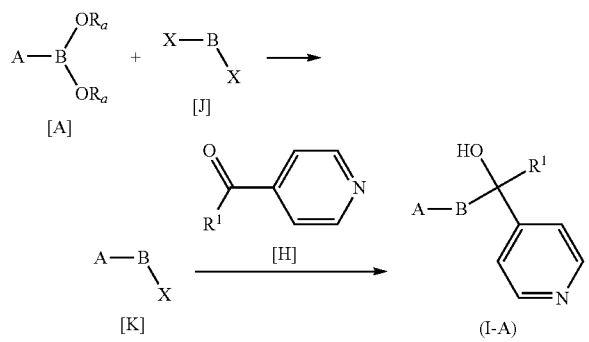

Scheme 4 describes a further method for the synthesis of compounds of formula (I-A). In this method, a boronic acid ($R_a$=H) or boronate ester ($R_a$=alkyl) derivative of fragment A [A] is first coupled to a heteroaryl di-halide [J], wherein X is, independently, halogen, to produce intermediate [K]. This coupling reaction may be performed by the method described for Scheme 1. In one embodiment, an anionic species of [K] is then generated from [K] by treatment with an alkyl metal reagent. In one embodiment, the alkyl metal reagent is n-butyl lithium. In a further embodiment, the anionic species of [K] is a Grignard reagent, generated from [K] by treatment with magnesium. The anionic species of [K] is then reacted with a pyridin-4-yl alkyl ketone [H] to form compounds of formula (I-A).

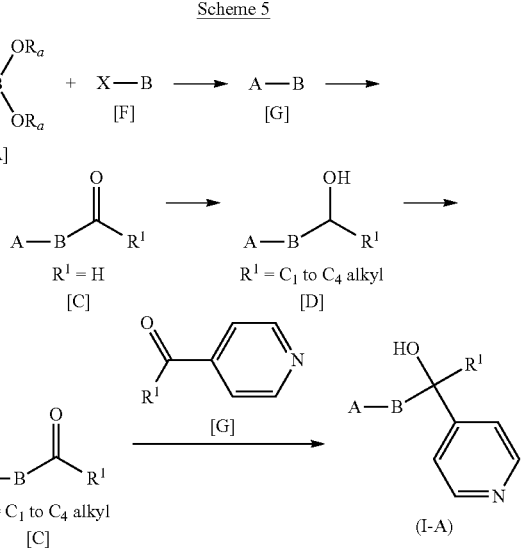

Scheme 5 depicts a further method for the preparation of compounds of formula (I-A). In this scheme, methods as described in Scheme 3 are used to prepare intermediate [G]. An anionic species of [G] is then generated from [G] by treatment with a strongly basic reagent. In one embodiment, the strongly basic reagent is n-butyl lithium or lithium diisopropylamide (LDA). This anionic species is then reacted with DMF to form aldehyde intermediate [C]. Aldehyde [C] is then converted in two steps to produce alkyl ketone [C] ($R^1$=$C_1$ to $C_4$ alkyl) by the method described in Scheme 2. Ketone [C] ($R^1$=$C_1$ to $C_4$ alkyl) is then converted to a compound of formula (I-A) by the method described in Scheme 1. Aldehyde intermediate [C] ($R^1$=H) may also be converted directly to a compound of formula (I-A) where $R^1$=H, by the methods described herein, such as Scheme 1.

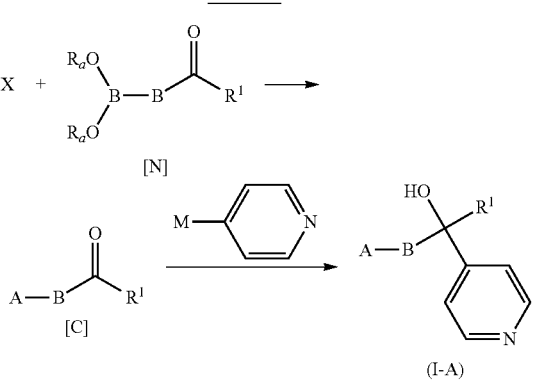

Scheme 6 depicts another method that is used for the synthesis of compounds of formula (I-A). In this scheme, a halide [L], wherein X is halogen, is coupled with a boronic acid ($R_a$=H) or boronate ester ($R_a$=alkyl) derivative of fragment B [N], using the methodology described herein, such as for Scheme 1. The intermediate [C] is then reacted with the 4-anion of pyridine, as described for Scheme 1, wherein M is a metal or metalloid moiety such as Li, Mg—Br or Mg—Cl. In one embodiment, the 4-anion of pyridine is pyridin-4-yl lithium.

Scheme 7

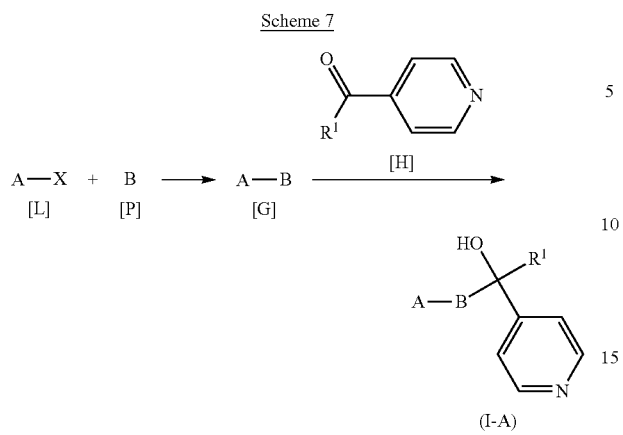

It will be apparent to those skilled in the art that there are a variety of other known coupling reaction methods that can be used to produce intermediates such as compound [G] in Schemes 1, 2, and 4. For example, as depicted in Scheme 7, a halide [L], where X is halogen, can be coupled with a heteroaryl species [P]. In one embodiment, the coupling is performed in the presence of CuI. In another embodiment, the coupling is performed in the presence of a palladium catalyst such as $Pd(OAc)_2$. In a further embodiment, the reaction is carried out at an elevated temperature such as 140° C. In still another embodiment, the reaction is performed in a solvent such as DMF. Alternatively, a halide [L] can be coupled with a heteroaryl species [P]. In one embodiment, this coupling is performed in the presence of AgF. In another embodiment, this coupling is performed in the presence of, $PPh_3$ and a palladium catalyst such as $Pd(PPh_3)_2Cl_2$. The intermediate [G] that is produced may be converted to compounds of formula (I-A) by the methods described herein, such as those for Scheme 3.

Scheme 8

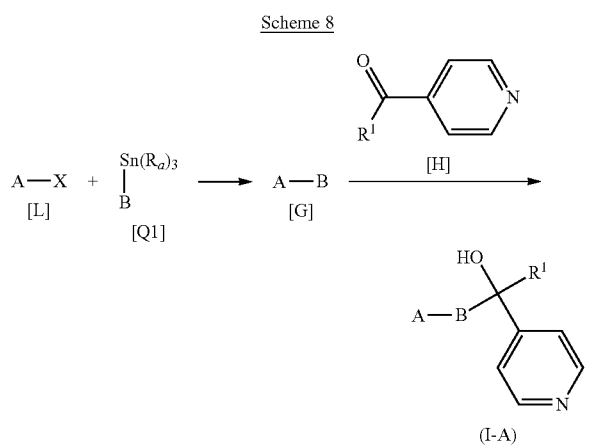

Scheme 8 describes a further coupling method that can be used in the preparation of compounds of formula (I-A). In this method, a halide [L], wherein X is halogen, is reacted with an activated derivative of B [Q1]. The intermediate [G] that is produced may be converted to compounds of Formula (I-A) including reaction with pyridine compound [H] and by the methods described above, such as Scheme 3.

Scheme 8A

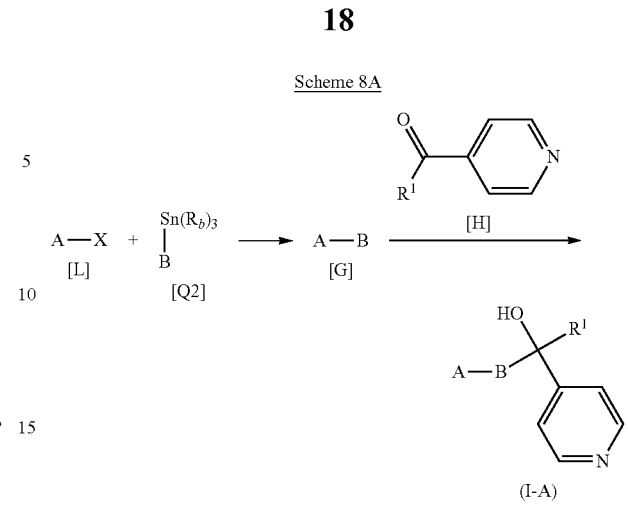

Scheme 8A describes one example of the general method of Scheme 8. In this embodiment, a halide [L], where X is halogen, is reacted with a tin derivative of B [Q2]. In one embodiment, the tin derivative is tributyl tin derivative ([Q2] where $R_b$=butyl). In another embodiment, the coupling reaction is carried out at elevated temperatures, such as 100° C. In a further embodiment, the coupling reaction is performed in a solvent, such as DMF. In still another embodiment, the coupling reaction is performed in the presence of a palladium catalyst, such as $Pd(PPh_3)_2Cl_2$. The intermediate [G] that is produced may be converted to compounds of Formula (I-A) by the methods described above, such as Scheme 3.

Scheme 8B

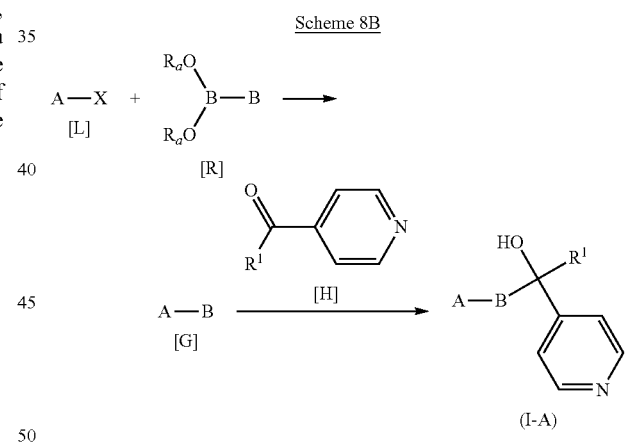

Scheme 8B describes a second example of the general method of Scheme 8. In this embodiment, a halide [L], wherein X is a halogen, is reacted with a boronic acid ($R_a$=H) or boronate ester ($R_a$=alkyl) derivative of fragment B [R]. This coupling reaction is carried out using various conditions, for example, as described for the related reaction step in Scheme 3. The intermediate [G] that is produced can be converted to compounds of Formula (I-A) by the methods described above, such as Scheme 3.

Scheme 8C

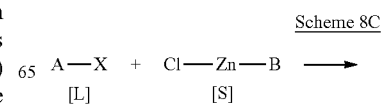

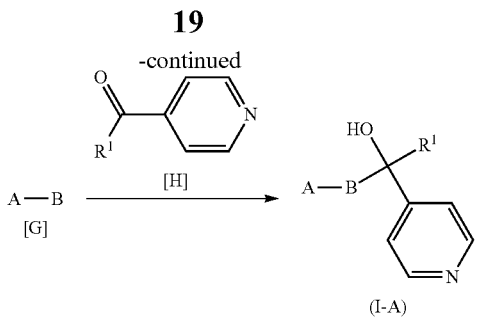

Scheme 8C describes a third example of the general method of Scheme 8. In this embodiment, a halide [L], wherein X is halogen, is reacted with a zinc derivative of fragment B [S]. The zinc derivative [S] may be prepared by treating fragment B with an alkyl lithium such as n-butyl lithium and zinc chloride, in THF at low temperatures such as −78° C. The coupling of [L] and [S] may be carried out in the presence of a nickel catalyst or a palladium catalyst, such as Pd(PPh$_3$)$_4$. The intermediate [G] that is produced may be converted to compounds of Formula (I-A) by the methods described above, such as Scheme 3.

cyclization reaction. See, Scheme 9. In this scheme, the 1,3,4-thiadiazole ring is prepared by reacting hydrazine carbothiamide with ethyloxalyl chloride in the presence of a cyclizing agent. In one embodiment, the cyclizing agent is POCl$_3$ or P$_2$O$_5$. In another embodiment, the cyclization is performed at elevated temperatures. The amine group bound to the thiadiazole ring of the intermediate is then replaced with a bromine substituent. In one embodiment, the reaction is performed using cupric bromide in the present of t-butyl nitrite. In another example, the reaction is performed at about 0° C. to about 60° C. in acetonitrile. The ester substituent is then reduced to the corresponding alcohol. In one embodiment, the reduction is performed using reducing agents known in the art such as sodium borohydride, lithium aluminum hydride, or diisobutyl aluminum hydride. The resultant alcohol is then coupled with the A substituent to provide intermediate [X]. In one embodiment, the coupling is performed using a boronic acid or boronate ester derivative of A, such as A-B(OH)$_2$. In another embodiment, the coupling is performed in the presence of a catalyst such as Pd(PPh$_3$)$_4$. Finally, intermediate [X] is oxidized to aldehyde [Y]. In one embodiment, the oxidation is performed using Dess-Martin periodinane. In a further embodiment, the oxidation is performed by using MnO$_2$ or PCC (pyridinium chlorochromate).

Scheme 9

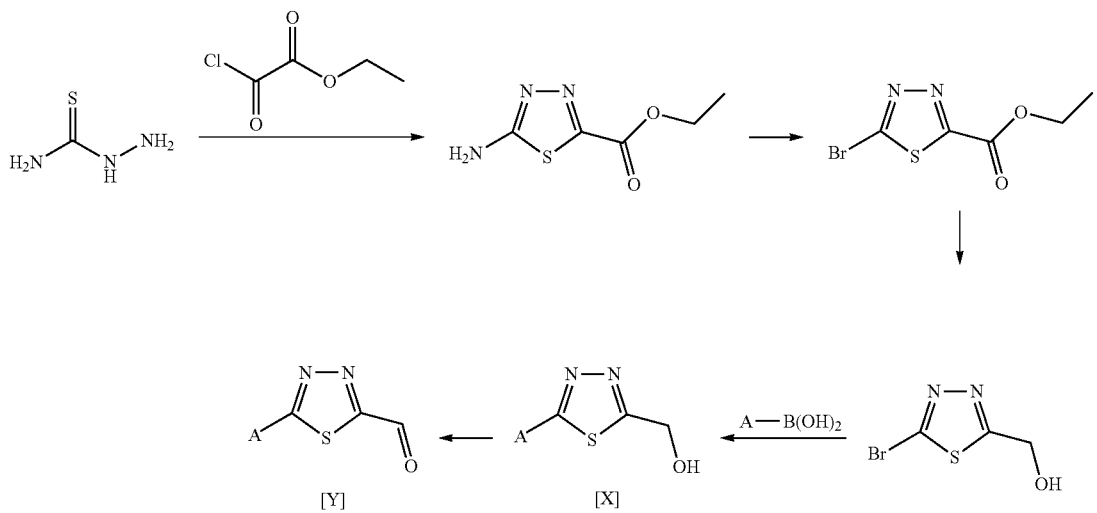

It will be recognized by those skilled in the art that various other methods can be used to prepare compounds of formula (I-A), in which either fragment A or B are produced by a The methodology described herein, such as Schemes 1 and 2, may then be applied to synthesize compounds of formula (I-A).

Scheme 9A

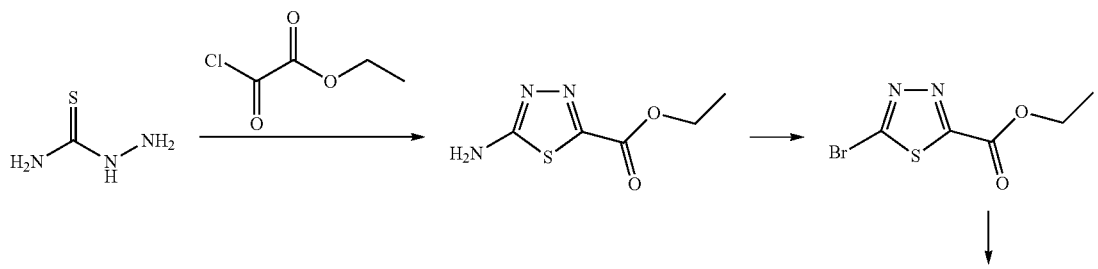

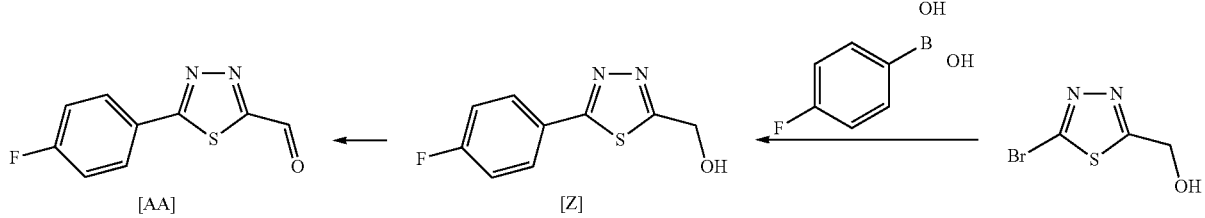

[AA]            [Z]

In another embodiment, compounds [Z] and [AA] may be prepared as depicted in Scheme 9A. In this scheme, the steps are similar to the steps of Scheme 9, with the exception that the "A" group of the boronic acid coupling reagent is a substituted phenyl group. In one embodiment, the "A" group of the boronic acid is 4-fluorophenyl and the product is 5-(4-fluorophenyl)-1,3,4-thiadiazole-2-carbaldehyde [AA].

about 100° C. for about 1 hour. (5-(4-Fluorophenyl)-1,3,4-thiadiazol-2-yl)methanol is then converted to 5-(4-fluorophenyl)-1,3,4-thiadiazole-2-carbaldehyde via reaction with Dess-Martin periodinane. In one embodiment, this reaction is performed in the presence of dichloromethane. In another embodiment, the reaction is performed at about room temperature of about 3 hours.

Scheme 9B

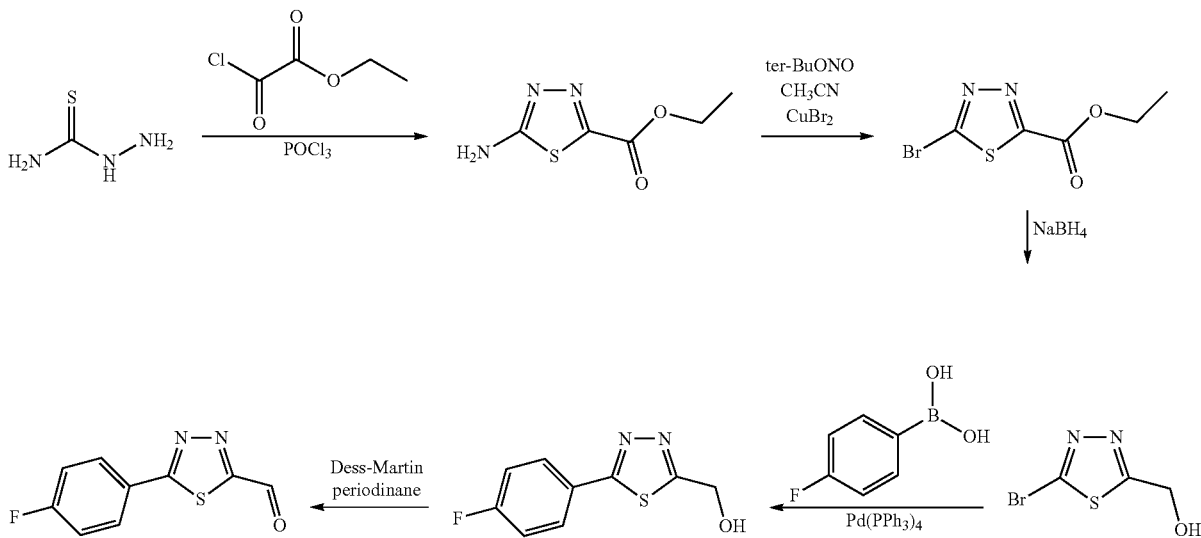

In a further embodiment, compounds of formula (I-A) may be prepared according to the transformations noted in Scheme 9B. In this scheme, the steps and transformations parallel those recited in Schemes 9 and 9A. Specifically, the 1,3,4-thiadiazole ring is synthesized by reacting hydrazine carbothiamide with ethyloxalyl chloride in the presence of POCl₃. In one embodiment, the cyclization is performed at elevated temperatures of about 70° C. for about 3 hours. The intermediate produced therefrom is then reacted with t-butyl nitrite in the presence of cupric bromide. In one embodiment, the reaction is performed in acetonitrile as solvent. In another embodiment, the reaction is performed at about room temperature to about 60° C. for about 1 hour. The resultant ethyl 5-bromo-1,3,4-thiadiazole-2-carboxylate is then reduced using sodium borohydride. In one embodiment, the reaction is performed in methanol at about room temperature for about 16 hours to provide 2-bromo-1,3,4-thiadiazolyl-5-methanol. This product is then coupled with 4-fluoro-phenyl boronic acid to provide (5-(4-fluorophenyl)-1,3,4-thiadiazol-2-yl)methanol [Z]. In one embodiment, the coupling is performed in the presence of Pd(PPh₃)₄. In another embodiment, the reaction is performed in toluene at an elevated temperature of Scheme 10

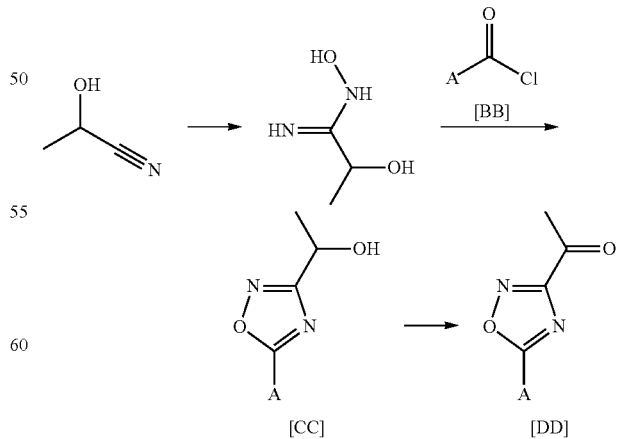

[CC]        [DD]

Scheme 10 provides a route to intermediate [CC] and/or [DD] via a cyclization reaction. In this case, a 1,2,4-oxadiazole ring is generated during the preparation of 1-(5-(4-fluorophenyl)-1,2,4-oxadiazol-3-yl)ethanol [CC]. Specifically, 2-hydroxy-propionitrile is converted to N,2-dihydroxypropanimidamide using hydroxylamine hydrochloride. The resultant compound is then coupled with the "A" substituent. In one embodiment, the resultant compound is reacted with an A-substituted acyl chloride [BB] to provide intermediate [CC]. Compound [CC] is then oxidized to provide ketone [DD]. In one embodiment, the oxidation is performed using Dess-Martin periodinane. In a further embodiment, the oxidation is performed by using MnO$_2$ or PCC (pyridinium chlorochromate). Intermediate [DD] may then be converted to a compound of formula (I-A) by the methods noted in the schemes, such as Scheme 1.

Scheme 10A

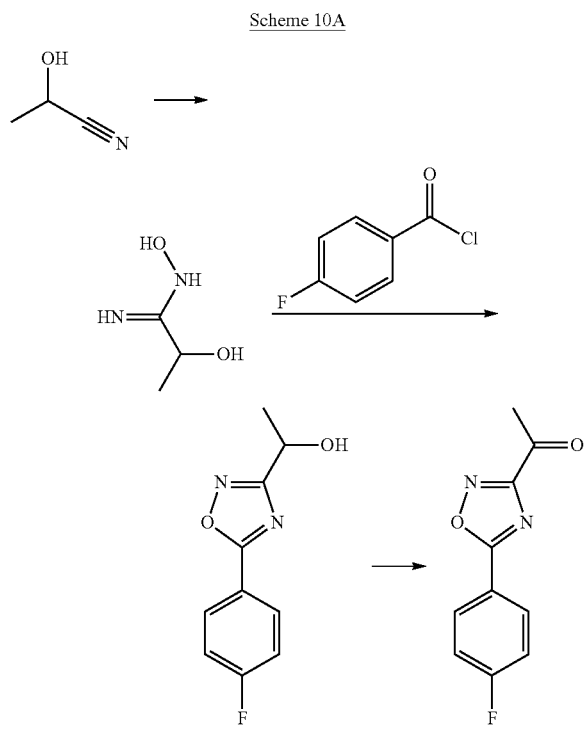

Scheme 10A provides the synthesis of a compound of formula (I-A), wherein B is a substituted phenyl group. The steps and transformations in this scheme parallel those described in Scheme 10, with the exception that "A" is 4-fluorophenyl. By doing so, intermediate [CC] is 1-(5-(4-fluorophenyl)-1,2,4-oxadiazol-3-yl)ethanol which may be oxidized to ketone [DD], i.e., 1-(5-(4-fluorophenyl)-1,2,4-oxadiazol-3-yOethanone, using the reagents and steps described in Scheme 10A. 1-(5-(4-fluorophenyl)-1,2,4-oxadiazol-3-yl)ethanone may then converted to a compound of formula (I-A) using the methods described above, such as Scheme 1.

Scheme 10B

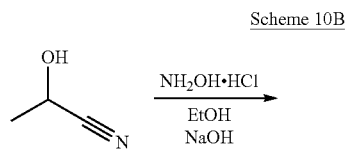

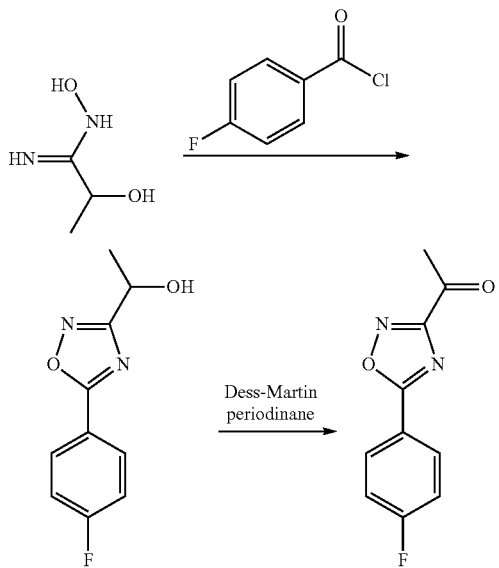

Scheme 10B describes the preparation of 1-(5-(4-fluorophenyl)-1,2,4-oxadiazon-3-yl)ethanone. In one embodiment, a 1,2,4-oxadiazole ring is generated during the preparation of 1-(5-(4-fluorophenyl)-1,2,4-oxadiazol-3-yl)ethanol by first reacting 2-hydroxy-propionitrile with hydroxylamine hydrochloride in the presence of ethanol or other lower alkyl alcohol as solvent, and sodium hydroxide or potassium hydroxide. In one embodiment, this reaction is performed at elevated temperatures such as the reflux temperature of the solvent. The resultant compound N,2-dihydroxypropanimidamide is then coupled with 4-fluoro-phenyl-chloroformate to provide intermediate 1-(5-(4-fluorophenyl)-1,2,4-oxadiazol-3-yl)ethanol. In one embodiment, the coupling is performed in ethanol. In another embodiment, the coupling is performed at a temperature of about 0 to about 85° C. 1-(5-(4-Fluorophenyl)-1,2,4-oxadiazol-3-yl)ethanol is then oxidized to the corresponding ketone using Dess-Martin periodinane. In one embodiment, the oxidation is performed in methylene chloride. In another embodiment, the oxidation is performed at about 0° C. to about room temperature.

Scheme 10C

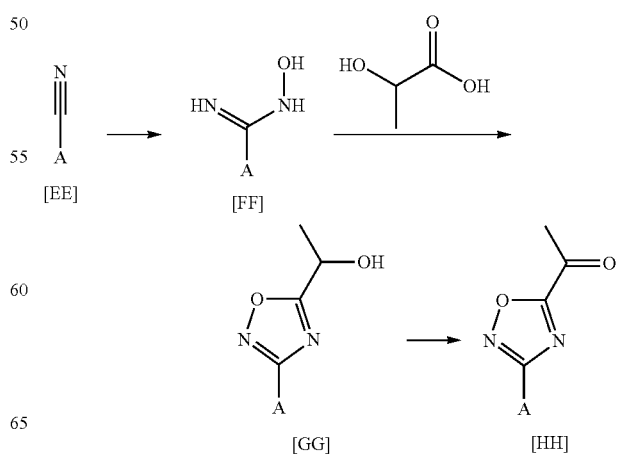

Intermediates [GG] and [HH] may also be prepared according to the methodology and reagents of Scheme 10C. A cyano-substituted "A" reagent [EE] is reacted with hydroxylamine hydrochloride to result in an N-hydroxy-imidamide derivative "A" of [FF]. This compound [FF] is then reacted with 2-hydroxy-propionic acid in the presence of a coupling agent to provide intermediate [GG]. In one embodiment, the coupling agent is dicyclohexylcarbodiimide (DCC) or N-ethyl-N'-dimethylaminoethyl-carbodiimide (EDCI). Compound [GG] is then oxidized to ketone intermediate [HH]. In one embodiment, the oxidation is performed using manganese dioxide, PCC (pyridinium chlorochromate) or Dess-Martin periodinane.

Scheme 10D

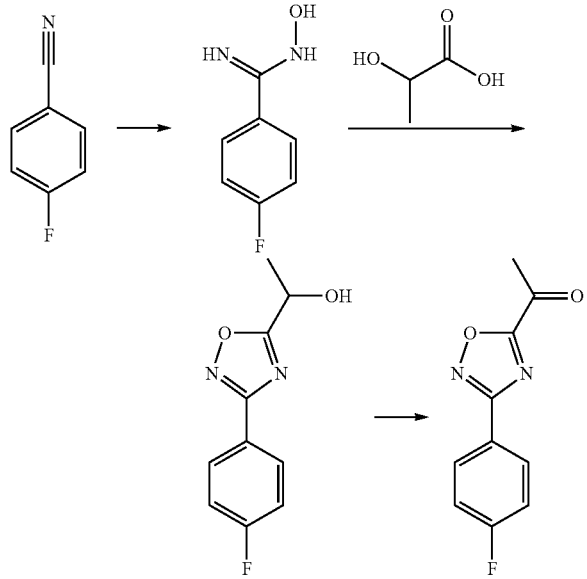

In another embodiment, intermediate compounds 1-(3-(4-fluorophenyl)-1,2,4-oxadiazol-5-yl)ethanol and 1-(3-(4-fluorophenyl)-1,2,4-oxadiazol-5-yl)ethanone may be prepared as described in Scheme 10D. In this route, 4-fluoro-benzonitrile is reacted with hydroxylamine hydrochloride to provide 4-fluoro-N-hydroxybenzimidamide. In one embodiment, the reaction is performed at refluxing temperatures. In another embodiment, the reaction is performed in the presence of a lower alkyl alcohol such as ethanol, and a base such as sodium hydroxide or potassium hydroxide. The resultant compound is then reacted with 2-hydroxy-propionic acid to provide 1-(3-(4-fluorophenyl)-1,2,4-oxadiazol-5-yl)ethanol. In one embodiment, the reaction is performed in the presence of DMSO, DCC, and HOBt. 1-(3-(4-Fluorophenyl)-1,2,4-oxadiazol-5-yl)ethanol is then oxidized to 1-(3-(4-fluorophenyl)-1,2,4-oxadiazol-5-yl)ethanone. In one embodiment, the oxidation is performed using manganese dioxide in dioxane.

Scheme 11

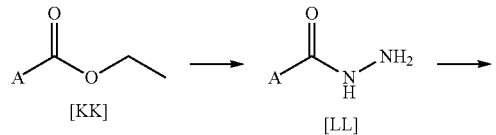

-continued

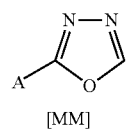

[MM]

A further example in which fragment B is produced by a cyclization reaction is provided in Scheme 11. In this case, a 1,3,4-oxadiazole ring, i.e., fragment B, is generated. Specifically, an A-substituted ethylformate [KK] is reacted with hydrazine hydrate to provide compound [LL]. Compound [LL] is then reacted with triethylorthoformate or boiling formic acid to provide intermediate [MM]. Compound [MM] may then be converted to a compound of formula (I-A) by the methods described in the schemes, such as Scheme 3.

Scheme 11A

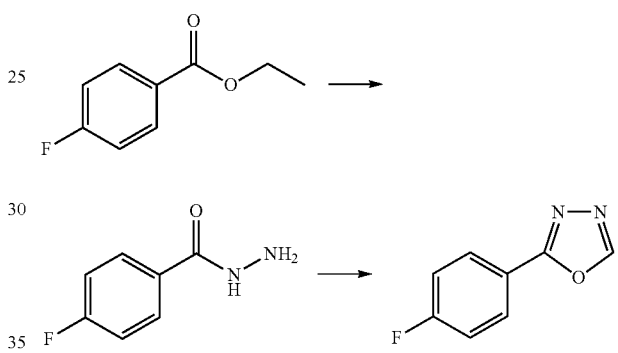

In one embodiment, 2-(4-fluorophenyl)-1,3,4-oxadiazole may be prepared as provided in Scheme 11A. In this case, 4-fluoro-phenyl-ethylformate is reacted with hydrazine hydrate to provide 4-fluorobenzohydrazide. This intermediate is then reacted with triethylorthoformate to provide 2-(4-fluorophenyl)-1,3,4-oxadiazole. 2-(4-Fluorophenyl)-1,3,4-oxadiazole may then be converted to a compound of formula (I-A) by the methods described herein.

Scheme 11B

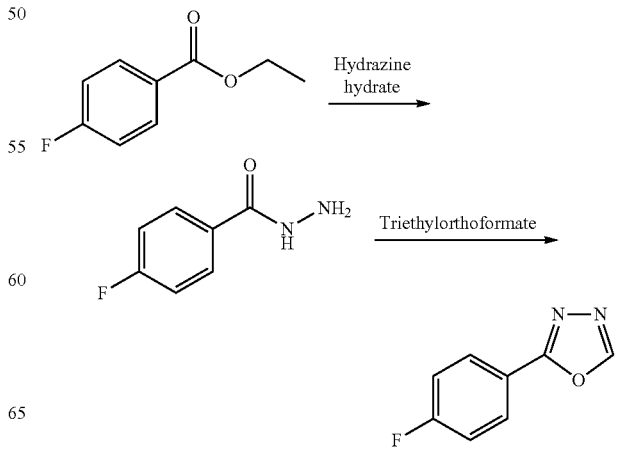

In another embodiment, 2-(4-fluorophenyl)-1,3,4-oxadiazole is prepared according to the methodology and reagents of Scheme 11B. In this embodiment, 4-fluoro-phenyl-ethylformate is reacted with hydrazine hydrate. In one embodiment, the reaction is performed in ethanol. In another embodiment, the reaction is performed at reflux temperatures for about 10 hours. The resultant compound 4-fluorobenzohydrazide is then reacted with triethylorthoformate to provide 2-(4-fluorophenyl)-1,3,4-oxadiazole. In one embodiment, this reaction is performed at about 140° C. for about 5 hours.

Scheme 12

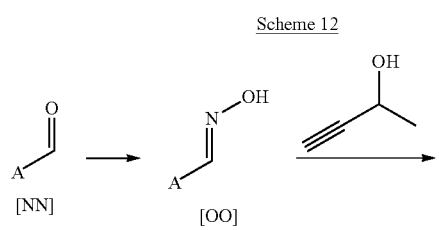

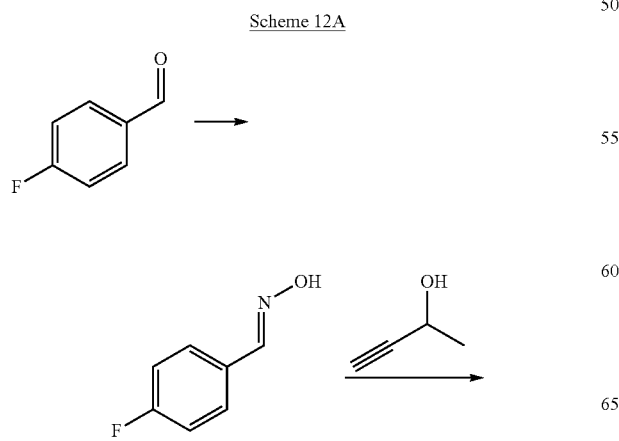

An additional example in which either intermediate [PP] or [QQ] are produced by a cyclization reaction is provided in Scheme 12. In this scheme, an A-substituted formaldehyde [NN] is reacted with hydroxylamine hydrochloride to provide an A-substituted oxime [OO]. Intermediate [OO] is then reacted with but-3-yn-2-ol and N-chlorosuccinimide (NCS) to provide intermediate [PP], which is then oxidized to the corresponding ketone [QQ]. In one embodiment, the oxidation is performed using Dess-Martin periodinane, manganese dioxide or PCC (pyridinium chlorochromate). Intermediate [QQ] may then be converted to a compound of formula (I-A) by the methods described in the schemes, such as Scheme 1.

Scheme 12A

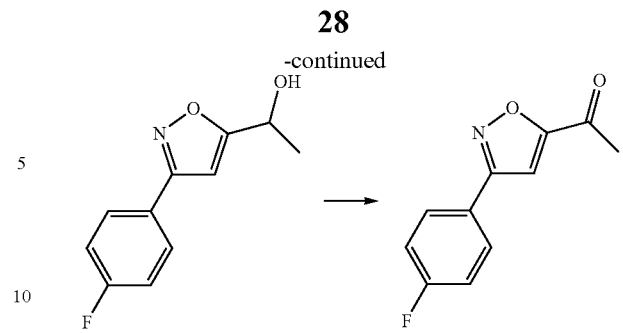

In another embodiment, 1-(3-(4-fluorophenyl)-isoxazol-5-yl)ethanol and 1-(3-(4-fluorophenyl)-isoxazol-5-yl)ethanone may be produced as described in Scheme 12A. 4-Fluoro-benzaldehyde is reacted with hydroxylamine hydrochloride to provide 4-fluorobenzaldehyde oxime. The isoxazole ring is then generated by reacting this intermediate with but-3-yn-2-ol and NCS to provide 1-(3-(4-fluorophenyl)isoxazol-5-yl)ethanol. 1-(3-(4-Fluorophenyl)isoxazol-5-yl)ethanol is then oxidized to the ketone, i.e., 1-(3-(4-fluorophenyl)-isoxazol-5-yl)ethanone, which may then be converted to a compound of formula (I-A) by the methods described herein.

Scheme 12B

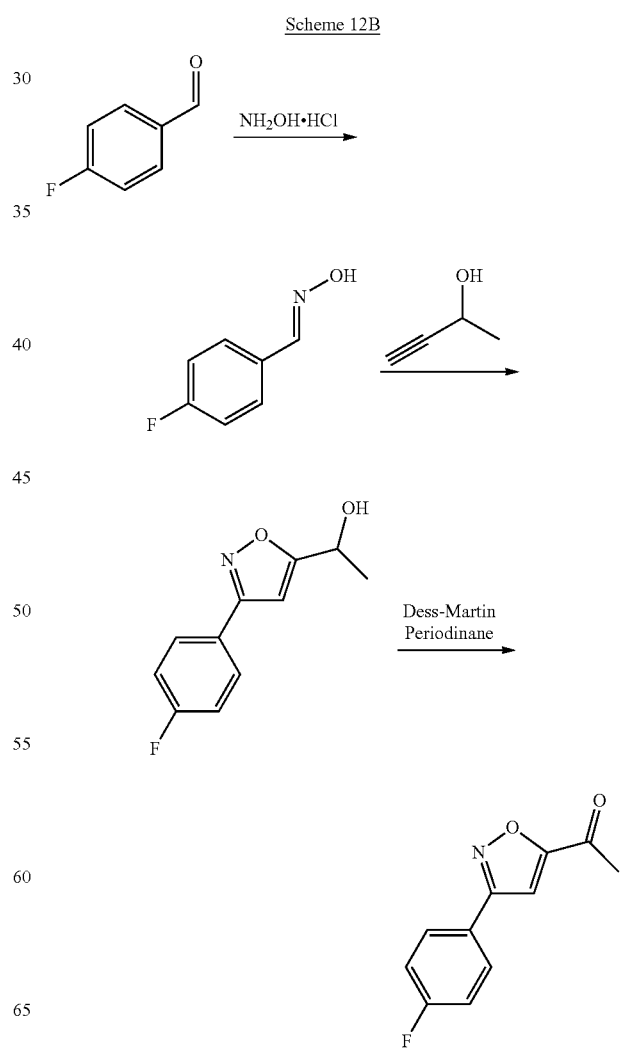

In a further embodiment, 1-(3-(4-fluorophenyl)-isoxazol-5-yl)ethanol and 1-(3-(4-fluorophenyl)-isoxazol-5-yl)ethanone are prepared according to the methodology and reagents of Scheme 12B. 4-Fluoro-benzaldehyde is reacted with hydroxylamine hydrochloride to provide 4-fluorobenzaldehyde oxime. In one embodiment, the reaction is performed in methanol and sodium carbonate. In another embodiment, the reaction is performed at about room temperature for about 4 hours. The isoxazole ring is then generated by reacting this intermediate with 3-hydroxy-butyne and NCS (about 1.2 equivalents) to provide 1-(3-(4-fluorophenyl)isoxazol-5-yl)ethanol. In one embodiment, this cyclization is performed in dichloromethane at about 40° C. 1-(3-(4-Fluorophenyl)isoxazol-5-yl)ethanol is then oxidized to 14344-fluorophenyl)-isoxazol-5-yl)ethanone using Dess-Martin periodinane. In one embodiment, the reaction is performed in dichloromethane. In another embodiment, the reaction is performed at room temperature for about 16 hours.

Scheme 13

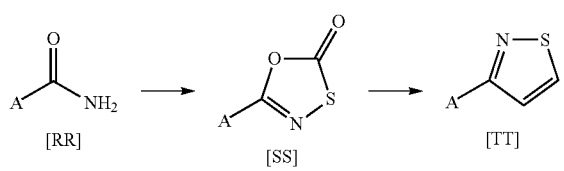

Scheme 13 provides another preparation of an intermediate useful herein, i.e., compound [TT]. In this embodiment, an amide-substituted "A" analog [RR] is converted to a 1,3,4-oxathiazol-2-one derivative [SS] by its reaction with chlorocarbonylsulfenyl chloride. Intermediate [SS] is then converted to intermediate [TT] by reaction with norbornadiene using microwave irradiation or at high temperature.

Scheme 13A

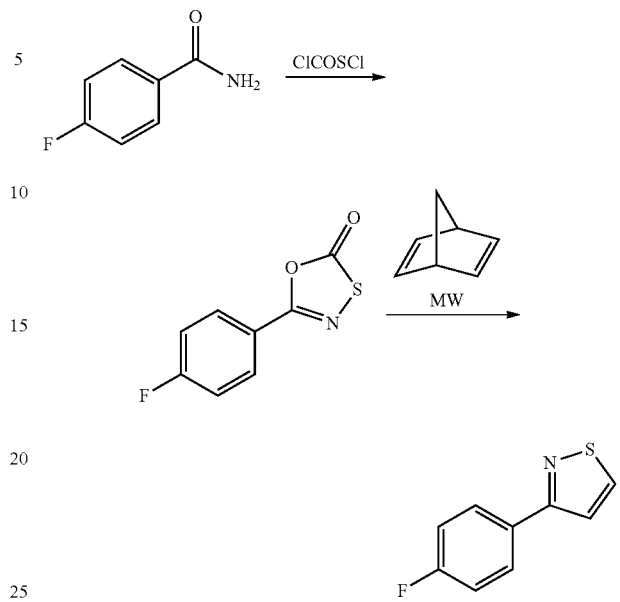

In an additional embodiment, the amide group of 4-fluorobenzamide is converted to a 1,3,4-oxathiazol-2-one group using chlorocarbonylsulfenyl chloride. In one embodiment, the reaction is performed in toluene at about room temperature. The resultant compound, i.e., 3-(4-fluoro-phenyl)-1,3,4-oxathiazol-5-one is then converted to an isothiazole ring using microwave (MW) irradiation in the presence of norbornadiene to provide 3-(4-fluorophenyl)isothiazole. In one embodiment, the microwave irradiation is applied at a temperature of about 170° C. for about thirty minutes. 3-(4-Fluorophenyl)isothiazole may then be converted to a compound of Formula (I) as described herein.

Scheme 14

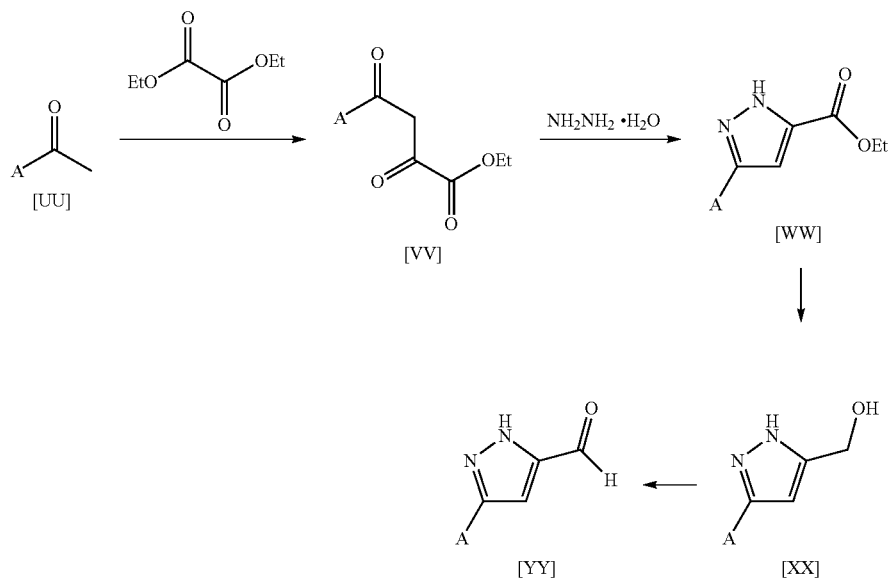

In another embodiment, intermediate [YY] may be prepared by a cyclization reaction as provided in Scheme 14. In this embodiment, compound [UU] is reacted with 1,2-diethoxy-1,2-ethanedione. The resultant intermediate [VV] is reacted with hydrazine hydrate to provide the A-substituted pyrazole ring intermediate [WW]. The ethyl acetate substituent of the pyrazole ring of compound [WW] is then reduced to provide compound [XX]. In one embodiment, the reduction is performed using lithium aluminum hydride, lithium borohydride or diisobutyl aluminum hydride. The resultant hydroxymethylene substituent of the pyrazole ring is then oxidized to a carbaldehyde substituent to provide compound [YY]. In one embodiment, the oxidation is performed using PCC and provides carbaldehyde [YY]. Compound [YY] may then be converted to a compound of Formula (I-A) using the methods described herein.

as potassium tert-butoxide. In another embodiment, this reaction is performed at about room temperature for about 24 hours. The pyrazole ring is then generated by reaction of ethyl 4-(4-fluorophenyl)-2,4-dioxobutanoate with hydrazine hydrate to provide ethyl 3-(4-fluorophenyl)-1H-pyrazole-5-carboxylate. In one embodiment, this reaction is performed in at elevated temperatures. In another embodiment, this reaction is performed in ethanol and glacial acetic acid for about 2 to 16 hours. Ethyl 3-(4-fluorophenyl)-1H-pyrazole-5-carboxylate is then reduced with lithium aluminum hydride to provide 3-(4-fluorophenyl)-1H-pyrazol-5-yl-methanol. In one embodiment, the reduction is performed in THF at a temperature of about 0° C. to about room temperature overnight. 3-(4-Fluorophenyl)-1H-pyrazole-5-carbaldehyde is then formed by oxidizing 3-(4-fluorophenyl)-1H-pyrazole-5-methanol. In one embodiment, the oxidation is performed Scheme 14A

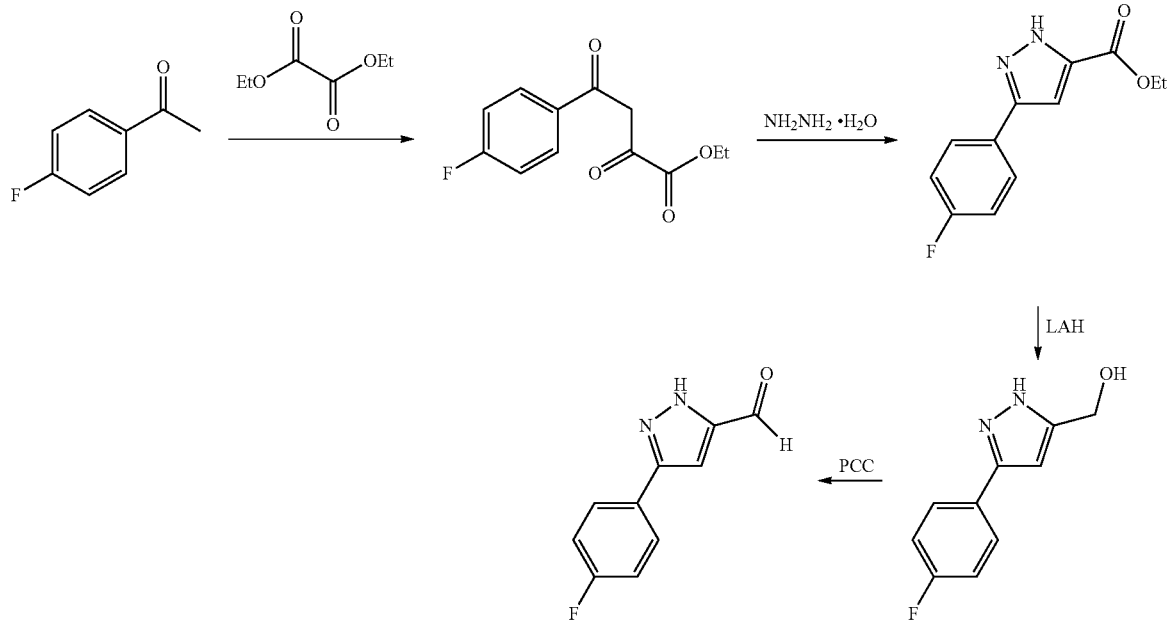

In a further embodiment, a pyrazole cyclization reaction is provided in Scheme 14A. In this embodiment, 1-(4-fluorophenyl)ethanone is reacted with diethyl oxalate to provide ethyl 4-(4-fluorophenyl)-2,4-dioxobutanoate. In one embodiment, this reaction is performed in the presence of a base such using PCC. In another embodiment, the oxidation is performed in dichloromethane at about room temperature overnight. 3-(4-Fluorophenyl)-1H-pyrazole-5-carbaldehyde may then converted to a compound of Formula (I-A) using the methods described herein.

Scheme 15

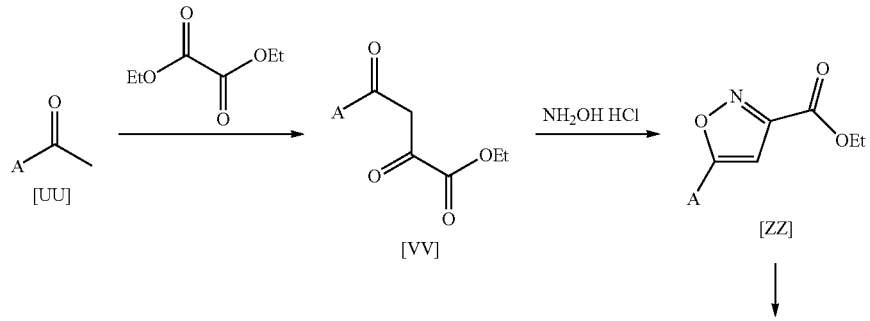

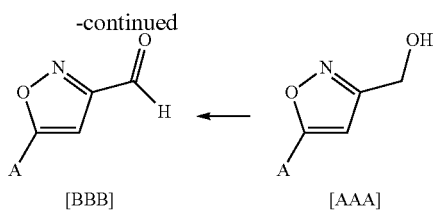

[BBB]  ←  [AAA]

Scheme 15 describes the preparation of compounds similar to those prepared in Scheme 14, but drawn to isoxazole rings. In this embodiment, compound [UU] is reacted with diethyl oxalate. The resultant intermediate [VV] is reacted with hydroxylamine hydrochloride to provide the A-substituted isoxazole ring intermediate [ZZ]. The ethyl acetate substituent of the isoxazole ring of [ZZ] is then reduced. In one embodiment, the reduction is performed using a reducing agent such as lithium aluminum hydride, lithium borohydride or diisobutyl aluminum hydride. The resultant hydroxymethylene substituent of the oxazole ring of [AAA] is then oxidized to a carbaldehyde substituent, i.e., compound [BBB]. In one embodiment, the oxidation is performed using an oxidizing agent such as PCC or MnO$_2$. Compound [BBB] is then converted to a compound of Formula (I-A) by the methods described herein.

isoxazole-3-carboxylate. In one embodiment, this reaction is performed in at elevated temperatures. In another embodiment, this reaction is performed in ethanol for about 2 hours. Ethyl 5-(4-fluorophenyl)-isoxazole-3-carboxylate is then reduced with lithium aluminum hydride to provide 5-(4-fluorophenyl)isoxazol-3-yl)methanol. In one embodiment, the reduction is performed in THF, at a temperature of about 0° C. to about room temperature overnight. 5-(4-Fluorophenyl) isoxazole-3-carbaldehyde is then formed by oxidizing (5-(4-fluorophenyl)isoxazol-3-yl)methanol. In one embodiment, the oxidation is performed using PCC. In another embodiment, the oxidation is performed in dichloromethane at about room temperature overnight. 5-(4-Fluorophenyl)isoxazole-3-carbaldehyde may then converted to a compound of Formula (I-A) using the methods described herein.

Scheme 15A

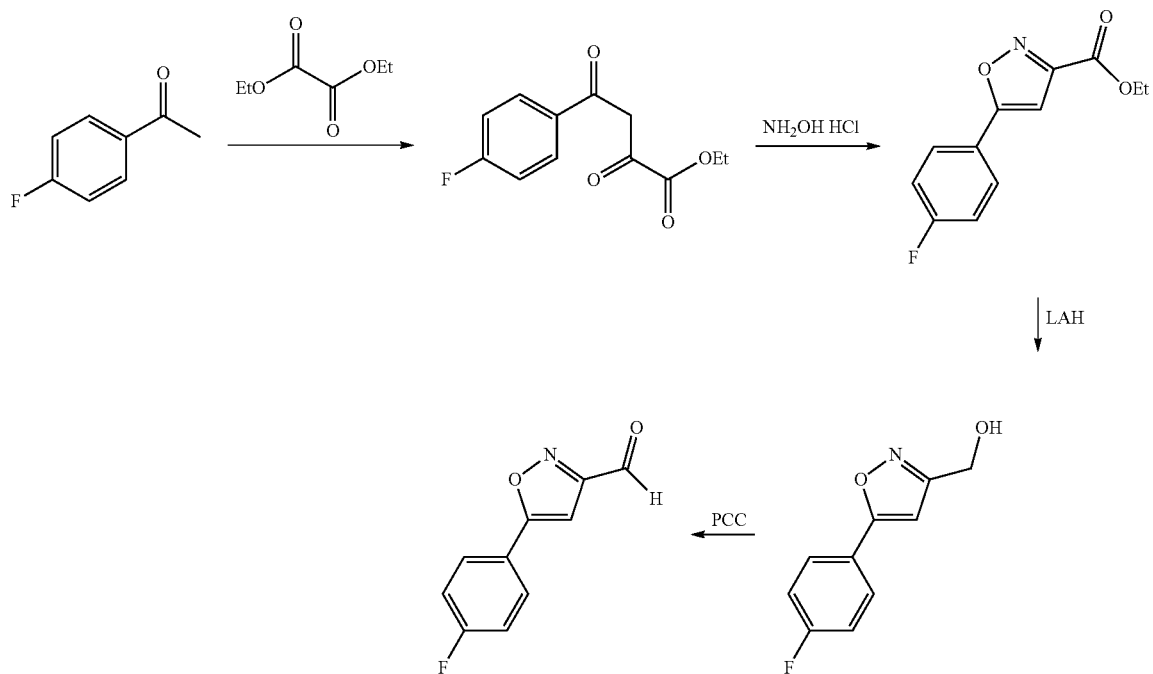

In a further embodiment, an isoxazole cyclization reaction is provided in Scheme 15A. In this embodiment, 1-(4-fluorophenyl)ethanone is reacted with diethyl oxalate to provide ethyl 4-(4-fluorophenyl)-2,4-dioxobutanoate. In one embodiment, this reaction is performed in the presence of a base such as potassium tert-butoxide. In another embodiment, this reaction is performed at about room temperature for about 24 hours. The isoxazole ring is then generated by reaction of ethyl 4-(4-fluorophenyl)-2,4-dioxobutanoate with hydroxylamine hydrochloride to provide ethyl 5-(4-fluorophenyl)

Scheme 16

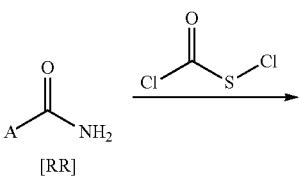

[RR]

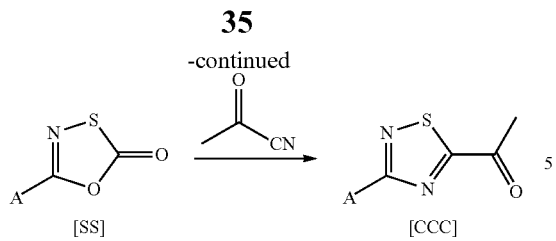

In yet another embodiment, intermediate [CCC] may be prepared according to the methodology and reagents described in Scheme 16. In this embodiment, an A-substituted amide [RR] is reacted with chlorocarbonylsulfenyl chloride to provide the A-substituted 1,3,4-oxathiazol-2-one ring [SS]. The 1,3,4-oxathiazol-2-one fragment is then converted to the corresponding 1,2,4-thiadiazole fragment via reaction with acetyl cyanide to provide the A-substituted 1-(1,2,4-thiadiazol-5-yl)ethanone intermediate [CCC]. Compound [CCC] may then be converted to a compound of Formula (I-A) by the methods described herein, such as Scheme 1.

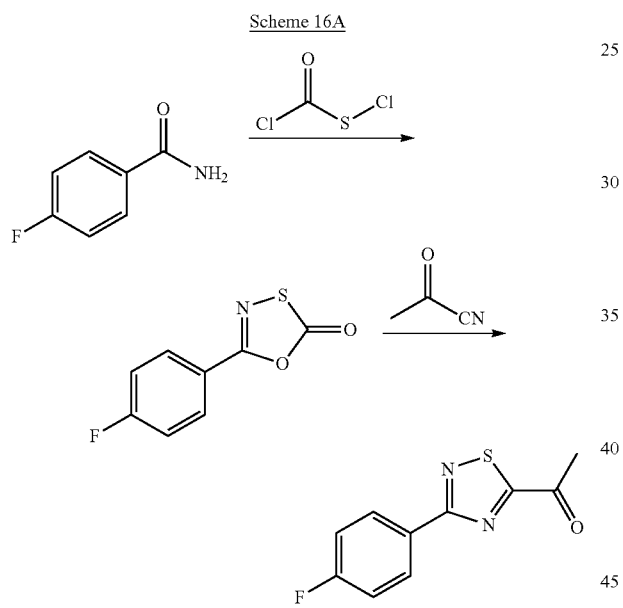

In still a further embodiment, 1-(3-(4-fluorophenyl)-1,2,4-thiadiazol-5-yl)ethanone may be prepared according to the methodology and reagents of Scheme 16A. In this embodiment, a 1,3,4-oxathiazol-2-one ring fragment is generated and subsequently converted to a 1,2,4-thiadiazole ring fragment during the preparation of 1-(3-(4-fluorophenyl)-1,2,4-thiadiazol-5-yl)ethanone. Specifically, 4-fluorobenzamide is reacted with chlorocarbonylsulfenyl chloride to provide 5-(4-fluoro-phenyl)-1,3,4-oxathiazol-2-one. In one embodiment, the reaction is performed in toluene. In another embodiment, the reaction is performed at elevated temperatures of about 80° C. for about 3 hours. 5-(4-Fluorophenyl)-1,3,4-oxathiazol-2-one is then reacted with acetyl cyanide to provide 1-(3-(4-fluorophenyl)-1,2,4-thiadiazol-5-yl)-ethanone. In one embodiment, this reaction is performed in 1,2-dichlorobenzene. In another embodiment, this reaction is performed at elevated temperatures of about 160° C. for about 20 hours. 1-(3-(4-Fluorophenyl)-1,2,4-thiadiazol-5-yl)ethanone is then converted to a compound of Formula (I-A) by the methods described herein, such as Scheme 1.

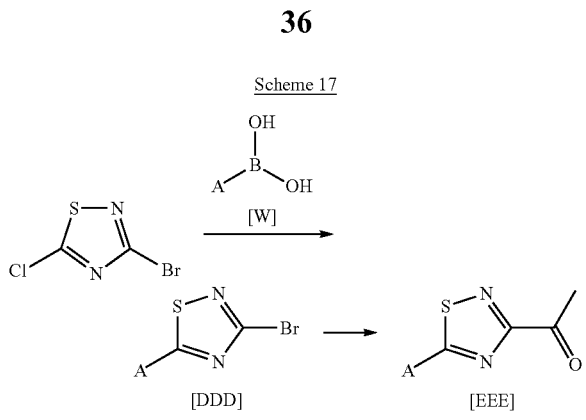

In a further embodiment, intermediate [EEE] may be prepared according to the methodology and reagents of Scheme 17. In this embodiment, the methods as described for Scheme 4 or Scheme 7, for example, may be used to prepare intermediate [DDD]. Intermediate [DDD] is then reacted with a tin reagent to convert the bromide in compound [DDD] to an acetyl group in intermediate [EEE]. In one embodiment, the tin reagent is tributyl(1-ethoxyvinyl)stannane. Compound [EEE] may then be converted to a compound of Formula (I-A) by the methods described herein, such as Scheme 1.

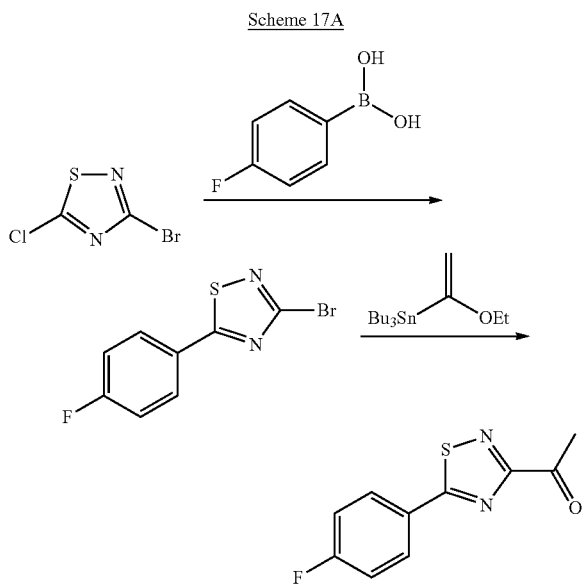

In another embodiment, 1-(5-(4-fluorophenyl)-1,2,4-thiadiazol-3-yl)ethanone is prepared according to the methodology and reagents of Scheme 17A. Specifically, 4-fluorophenyl boronic acid is reacted with 3-bromo-5-chloro-1,2,4-thiadiazole to provide 3-bromo-5-(4-fluorophenyl)-1,2,4-thiadiazole. 3-Bromo-5-(4-fluorophenyl)-1,2,4-thiadiazole is then reacted with a tin reagent such as tributyl(1-ethoxyvinyl)-stannane to convert the bromide moiety of 3-bromo-5-(4-fluorophenyl)-1,2,4-thiadiazole to an acetyl group. In one embodiment, this reaction is performed in the presence of a catalyst such as $PdCl_2(PPh_3)_4$. In another embodiment, the reaction is performed in DMF at elevated temperatures overnight. 1-(5-(4-Fluorophenyl)-1,2,4-thiadiazol-3-yl)-ethanone may then converted to a compound of Formula (I-A) by the methods described herein, such as Scheme 1.

Scheme 18

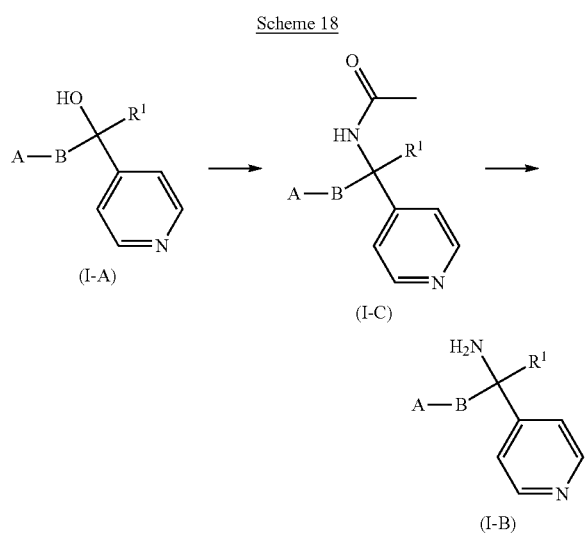

Scheme 19B

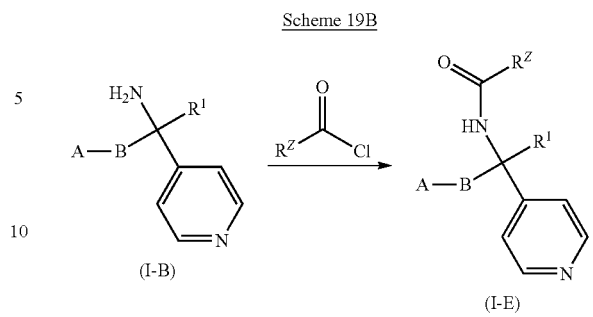

Compounds of Formula (I-B) may be prepared from compounds of Formula (I) where Q=O, by the method described in Scheme 18. In this method, a compound of Formula (I) where Q=O is first treated under acidic conditions to form the acetyl amide derivative [I-C]. In one embodiment, the reaction is carried out in acetonitrile. In another embodiment, the reaction is performed at elevated temperatures such as at 90° C. In a further embodiment, the reaction is performed, in the presence of a strong acid such as concentrated sulfuric acid. The amide intermediate [I-C] is then hydrolyzed to provide compounds of Formula (I-B). In one embodiment, the hydrolysis reaction is performed using a strong acid such as hydrochloric acid. In another embodiment, the hydrolysis is performed at elevated temperatures. In a further embodiment, the hydrolysis is performed by heating intermediate [I-C] in aqueous hydrochloric acid in a sealed tube at about 100° C. for several hours, such as 24 hours, to provide compounds of Formula (I-B).

Scheme 19A

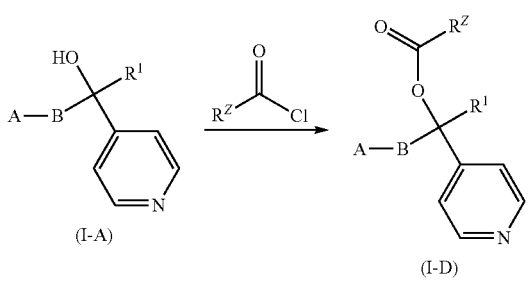

Acetyl and other ester prodrugs of compounds of Formula (I) where Q=O, i.e., compound (1-D), may be prepared using the methods described herein. In one embodiment, a compound of Formula (I) where Q=O may be reacted with a acyl chloride. In another embodiment, the acyl chloride may be $R^ZC(O)Cl$. In a further embodiment, the reaction may be performed in the presence of a base such as potassium tert-butoxide, to provide prodrug compound [I-D] as described in Scheme 19A.

Acetyl and other amide prodrugs of compounds of Formula (I) where Q=NH, i.e., compound (I-E), may be prepared by using the methods described herein. In one embodiment, compounds of Formula (I-B) are reacted with an acyl chloride. In another embodiment, the acyl chloride is $R^ZC(O)Cl$. In a further embodiment, the reaction may be performed in the presence of a base such as pyridine.

Scheme 19C

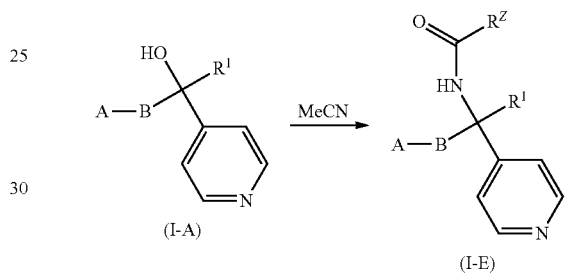

As well, acetyl amide prodrugs of compounds of Formula (I-E) may be prepared by reaction of a compound of Formula (I-A) where Q=O with acetonitrile. In one embodiment, the reaction is performed under acidic conditions to provide prodrug compound [I-E] as described in Scheme 19C.

Pharmaceutical compositions useful herein contain a compound of formula (I) in a pharmaceutically acceptable carrier optionally with other pharmaceutically inert or inactive ingredients. In another embodiment, a compound of formula (I) is present in a single composition. In a further embodiment, a compound of formula (I) is combined with one or more excipients and/or other therapeutic agents as described below.

The pharmaceutical compositions of the invention comprise an amount of a compound of formula (I) or a pharmaceutically acceptable salt or prodrug thereof that is effective for regulating CYP17 activity in a subject. Specifically, the dosage of the compound of formula (I) to achieve a therapeutic effect will depend on the formulation, age, weight and sex of the patient and route of delivery. It is also contemplated that the treatment and dosage of the compound of formula (I) may be administered in unit dosage form and that one skilled in the art would adjust the unit dosage form accordingly to reflect the relative level of activity. The decision as to the particular dosage to be employed, (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formula (I) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a pharmaceutically acceptable salt or prodrug thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers. A variety of suitable liquid carriers is known and may be readily selected by one of skill in the art. Such carriers may include, e.g., DMSO, saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition for which it has been selected.

The compounds of formula (I) may, be delivered orally, by injection, inhalation (including orally, intranasally and intratracheally), ocularly, transdermally, intravascularly, subcutaneously, intramuscularly, sublingually, intracranially, epidurally, intravesically, rectally, and vaginally, among others.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, e.g., tablet or caplet. In another embodiment, the composition may be added to unit dose form, e.g., a capsule. In a further embodiment, the composition may be formulated for administration as a powder. The solid carrier may perform a variety of functions, e.g., may perform the functions of two or more of the excipients described below. For example, solid carrier may also act as a flavoring agent, lubricant, solubilizer, suspending agent, filler, glidant, compression aid, binder, disintegrant, or encapsulating material. The composition may also be sub-divided to contain appropriate quantities of the compound of formula (I). For example, the unit dosage can be packaged compositions, e.g., packeted powders, vials, ampoules, prefilled syringes or sachets containing liquids.

Examples of excipients which may be combined with one or more compound of formula (I) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) which is delayed or otherwise controlled. Those of skill in the art know suitable sustained delivery devices. For use in such sustained delivery devices, the compound of formula (I) is formulated as described herein.

In addition to the components described above for use in the composition and the compound of formula (I), the compositions may contain one or more medications or therapeutic agents which are used to treat solid tumors. In one embodiment, the medication is a chemotherapeutic, including but not limited to cytotoxic/cytostatic agents and targeted agents such as include LHRH agonist/antagonists, androgen receptor antagonists, kinase or other enzyme inhibitors, and the like. Examples of chemotherapeutics include those recited in the "Physician's Desk Reference", $64^{th}$ Edition, Thomson Reuters, 2010, which is hereby incorporated by reference. In one embodiment, the compounds of formula (I) can be administered with other inhibitors of CYP17, such as abiraterone acetate, or with compounds that suppress testosterone production, such as LHRH agonists/antagonists. Therapeutically effective amounts of the additional medication(s) or therapeutic agents are well known to those skilled in the art. However, it is well within the attending physician to determine the amount of other medication to be delivered.

The compounds of formula (I) and/or other medication(s) or therapeutic agent(s) may be administered in a single composition. However, the present invention is not so limited. In other embodiments, the compounds of formula (I) may be administered in one or more separate formulations from other compounds of formula (I), chemotherapeutic agents, or other agents as is desired.

Also provided herein are kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability. A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhaler, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper or any such medically approved delivery means.

In one embodiment, a kit is provided and contains a compound of formula (I). The compound of formula (I) may be in the presence or absence of one or more of the carriers or excipients described above. The kit may optionally contain instructions for administering the medication and the compound of formula (I) to a subject having a disease associated with CPY17 activity.

In a further embodiment, a kit is provided and contains a compound of formula (I) in a second dosage unit, and one or more of the carriers or excipients described above in a third dosage unit. The kit may optionally contain instructions for administering the medication and the compound of formula (I) to a subject having a disease associated with CPY17 activity.

The compounds described herein are useful in treating conditions which are associated with CPY17 activity. In one embodiment, such a disease is associated with abnormal cellular proliferation, particularly the abnormal proliferation of cells which is sensitive to hormones such as testosterone or estrogen. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In one embodiment, the disease characterized by abnormal cellular proliferation is cancer of the prostate.

The term "regulation" or variations thereof as used herein refers to the ability of a compound of formula (I) to inhibit one or more components of a biological pathway. In one embodiment, "regulation" refers to inhibition of CPY17 activity.

In one embodiment, methods for inhibiting CPY17 activity are provided which comprise administering a therapeutically effective amount of a compound of formula (I) to a patient in need thereof.

In another embodiment, methods for treating a disease characterized by an abnormal cellular growth associated with CPY17 activity are provided which comprise administering of a therapeutically effective amount of a compound of formula (I) to a patient in need thereof.

In a further embodiment, methods for treating a condition treatable by inhibiting CPY17 activity are provided which comprise administering a therapeutically effective amount of a compound of formula (I) to a patient in need thereof.

In still another embodiment, methods for treating cancer are provided which comprise administering a therapeutically effective amount of a compound of formula (I) to a patient in need thereof.

In yet a further embodiment, methods for treating prostate cancer are provided which comprise administering a therapeutically effective amount of a compound of formula (I) to a patient in need thereof.

In a still further embodiment, methods of reducing testosterone production in a patient are provided which comprise administering a therapeutically effective amount of a compound of formula (I) in need thereof.

As described herein, a therapeutically effective amount of a compound when used for the treatment of cancer is an amount which may reduce the number of cancer cells (cytotoxic), allow the number of cancer cells to remain relatively constant (cytostatic), reduce tumor size, inhibit metastasis, inhibit tumor growth and/or ameliorate one or more of the symptoms of the cancer. For cancer therapy, efficacy can be measured for example, by assessing the time to disease progression, measuring tumor size and/or determining the patient response rate.

The following examples are illustrative only and are not intended to limit the present invention.

EXAMPLES

All reactions were carried out under dry nitrogen or argon atmosphere unless otherwise specified. Unless otherwise stated, all the raw starting materials, solvents and reagents were purchased from commercial sources (e.g., Avocado Research Chemicals, Apollo Scientific Limited, Bepharma Ltd., Combi-Blocks Inc., Sigma Aldrich Chemicals Pvt. Ltd., Ultra Labs, Toronto Research Chemicals Inc., Chemical House, RFCL Limited, Spectro Chem. Pvt. Ltd., Leonid Chemicals, Loba Chemie, Changzhou Yangyuan, NeoSynth., Rankem) and used as such without further purification, or reagents can be synthesized by procedures known in the art.

The following abbreviations are used and have the indicated definitions: MHz is megahertz (frequency), m is multiplet, t is triplet, d is doublet, s is singlet, br is broad, $CDCl_3$ is deutero chloroform, calcd is calculated, min is minutes, h is hours, g is grams, mmol is millimoles, mL is milliliters, N is Normal (concentration), M is molarity (concentration), μM is micromolar, ee is enantiomeric excess, ° C. is degree centigrade, HPLC is High Performance Liquid Chromatography, LC-MS is Liquid Chromatography-Mass Spectroscopy, NMR is Nuclear Magnetic Resonance, TLC is thin layer chromatography, THF is tetrahydrofuran, MeOH is methanol, DCM is dichloromethane, DEA is diethylamine, DMA is dimethylacetamide, DMF is N,N-dimethyl formamide, DMSO is dimethyl sulfoxide, EtOH is ethyl alcohol, EtOAc is ethyl acetate, MeOH is methanol, RT is room temperature, HCl is hydrogen chloride or hydrochloric acid, TFA is trifluoroacetic acid, EtMgBr is ethyl magnesium bromide, n-BuLi is n-butyl lithium, $NaHCO_3$ is sodium bicarbonate, $Na_2CO_3$ is sodium carbonate, $Na_2SO_4$ is sodium sulfate, DCC is N,N-dicyclohexylcarbodiimide, DIPA is diisopropylamine, LDA is lithium diisopropylamine, HOBt is N-hydroxy-benzotriazole, NCS is N-chlorosuccinimide, and TBAB is tetrabutyl ammonium bromide.

Biotage Isolera® One and CombiFlash® (Teledyne Isco) Automated Flash Purification System were used for the purification of crude products using the eluent combination mentioned in the respective procedures. Flash Chromatography was performed using silica gel (60-100, 100-200 and 230-400 mesh) from ChemLabs, with nitrogen and/or compressed air. Preparative thin-layer chromatography was carried out using silica gel (GF 1500 μM 20×20 cm and GF 2000 μM 20×20 cm Prep-scored plates from Analtech, Inc. Delaware, USA). Thin-layer chromatography was carried out using pre-coated silica gel sheets (Merck 60 $F_{254}$). Visual detection was performed with ultraviolet light, p-anisaldehyde stain, ninhydrin stain, dinitrophenyl hydrazine stain, potassium permanganate stain, or iodine. Reactions at lower temperature were performed by using cold baths, e.g., $H_2O$/ice at 0° C., and acetone/dry ice at –78° C. Melting points were determined by using a LabIndia visual melting range apparatus. $^1$H NMR spectra were recorded at 400 MHz with a Varian V400 spectrometer, Bruker 400 (unless otherwise noted) at ambient temperature, using tetramethylsilane as internal reference. The chemical shift values are quoted in δ (parts per million). Mass spectra of all the intermediates and final compounds were recorded using Acquity® UPLC-SQD (Waters) & Agilent 1290 Infinity® with 6150 SQD machines. HPLC spectra were recorded using Agilent 1290 Infinity® UHPLC and Alliance (Waters) systems. LCMS spectra were recorded using Agilent 1200® LCMS/Agilent 1290® UHPLC-SQD with diode array detector (DAD) detection LC-MS instruments using a BEH C18 column and Zorbax® HD C18 column (50 mm×2.1 mm×1.7μ) & (50 mm×2.1 mm×1.8μ), a mobile phase of 0.01% of acetic acid with acetonitrile and 0.01% of acetic acid with methanol, a flow rate of 0.3 mL/min, a temperature of 70 and 50° C., and a run time of 3.0 and/or 5 min. The purity of each of the final compounds was detected using Waters® PDA with SQD and Aglient® DAD with 6150 SQD instruments and the following conditions:

Condition 1: Column: BEH C18 (Waters); mobile phase: 0.01% acetic acid with acetonitrile & 0.01% acetic acid with methanol; gradient: (B/% T): 0/0, 1.2/100, 2.5/100, 2.8/0, 3.0/0; flow: 0.3 mL/min; temperature: 70° C.; run time: 3.0 min.

Condition 2: Column: Zorbax® HD C18; mobile phase: 0.01% acetic acid with acetonitrile & 0.01% acetic acid with methanol; gradient: (B/% T): 0/0, 2.5/100, 4.5/100, 4.8/0, 5.0/0; flow: 0.3 mL/min; temperature: 50° C.; run time: 5.0 min Example 1

1-(5-(4-Methoxyphenyl)pyridin-2-yl)-1-(pyridin-4-yl)ethanol (Synthetic Method of Scheme 1)

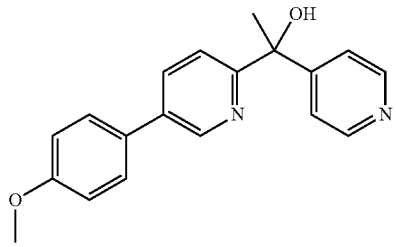 [SMILES: COc1ccc(-c2ccc(C(C)(O)c3ccncc3)nc2)cc1]

Step 1:
1-(5-(4-Methoxyphenyl)pyridin-2-yl)ethanone

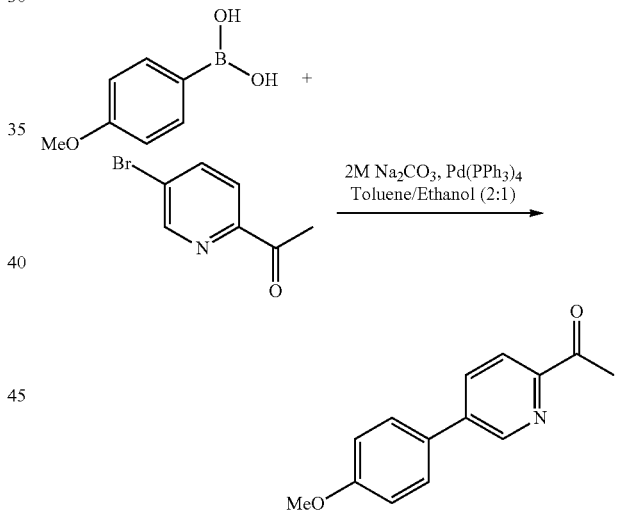

To a stirred solution of toluene and ethanol (9 mL, 2:1) of 1-(5-bromopyridin-2-yl)ethanone (200 mg, 1 mmol) was added (4-methoxyphenyl) boronic acid (304 mg, 2 mmol), 2M $Na_2CO_3$ (2.84 mL), and $Pd(PPh_3)_4$ (11 mg, 0.01 mmol) under argon atmosphere and heating was continued for 5 hours at 70° C. The reaction mixture was concentrated under vacuum and diluted with water (100 mL) and extracted with EtOAc (2×200 mL). The combined extracts were washed with brine solution (20 mL), and organic layer was dried over $Na_2SO_4$ and concentrated under vacuum to obtain crude product. This, on purification by flash chromatography (silica gel, 60-120μ) using 10% ethyl acetate in hexane eluent, afforded 1-(5-(4-methoxyphenyl)pyridin-2-yl)ethanone as off-white solid (200 mg, 88% yield). 1H NMR (400 MHz, DMSO-$d_6$): δ 8.99 (d, 1H), 8.20 (dd, 1H), 7.97 (d, 1H), 7.76 (d, 2H), 7.07 (d, 2H), 3.81 (s, 3H), 2.63 (s, 3H); LC-MS m/z calculated for $[M+H]^+$ 228.27. found 228.4.

Step 2: 1-(5-(4-Methoxyphenyl)pyridin-2-yl)-1-(pyridin-4-yl)ethanol

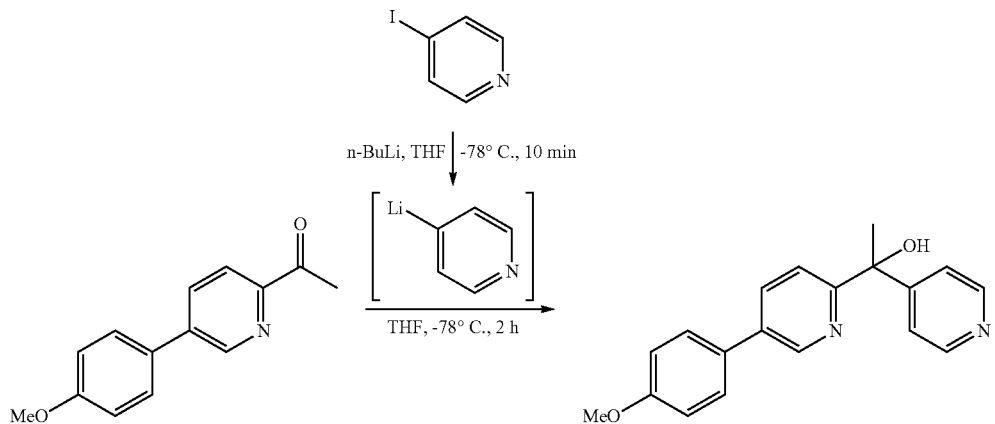

To cooled (−78° C.) 4-iodopyridine (270 mg, 1.3 mmol) [Albrecht, et al., US Patent Application Publication No. 2009/0318436] in THF (15 mL) was added slowly 1.6 M n-BuLi in hexane (1.65 mL, 2.6 mmol). Stirring was continued for an additional 30 minutes at the same temperature, followed by the addition of a THF (5 mL) solution of 1-(5-(4-methoxyphenyl)pyridin-2-yl)ethanone (300 mg, 1.3 mmol). After stirring for 2 hours at the same temperature, the reaction mixture was quenched with saturated aqueous NH$_4$Cl solution (10 mL). The aqueous layer was extracted with ethylacetate (2×150 mL). The combined organic layers were washed with brine (20 mL). Finally, the organic phase was dried over Na$_2$SO$_4$ and concentrated under reduced pressure to give crude product. The crude product was purified by flash chromatography (silica gel 60-120μ) using 20% ethyl acetate and hexane as eluent to afford racemic 1-(5-(4-methoxyphenyl)pyridin-2-yl)-1-(pyridin-4-yl)ethanol as an off-white solid (135 mg, 33% yield) in 99.6% HPLC purity. 1H NMR (400 MHz, DMSO-d$_6$): δ 8.74 (d, 1H), 8.45 (dd, 2H), 7.98 (dd, 1H), 7.68 (d, 1H), 7.62 (d, 2H), 7.48 (dd, 2H), 7.02 (d, 2H), 6.15 (s, 1H), 3.78 (s, 3H), 1.88 (s, 3H); LC-MS m/z calculated for [M+H]$^+$ 307.14. found 307.3.

Examples 2 & 3

Enantiomer #1 and Enantiomer #2 of 1-(5-(4-methoxyphenyl)-pyridin-2-yl)-1-(pyridin-4-yl)ethanol

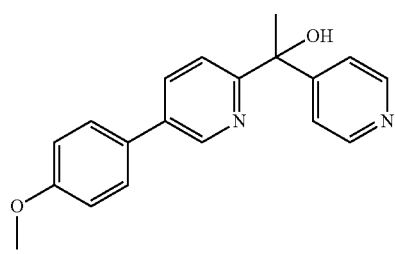 [SMILES: COc1ccc(-c2ccc(C(C)(O)c3ccncc3)nc2)cc1]

Racemic 1-(5-(4-methoxyphenyl)pyridin-2-yl)-1-(pyridin-4-yl)ethanol (100 mg) was subjected to chiral HPLC purification using a Chiralpak® IC [250 mm×4.6 mm×5μ column, mobile phase: n-heptane:ethanol with 0.01% DEA (50:50); flow rate: 1 mL/min] to afford 33 mg (66% recovery) of 1-(5-(4-methoxyphenyl)pyridin-2-yl)-1-(pyridin-4-yl)ethanol (Enantiomer #1) and 33 mg (66% recovery) of 1-(5-(4-methoxyphenyl)pyridin-2-yl)-1-(pyridin-4-yl)ethanol (Enantiomer #2), each with >99.5% ee. For each enantiomer: 1H NMR (400 MHz, DMSO-d$_6$): δ 8.74 (d, 1H), 8.45 (d, 2H), 7.98 (dd, 1H), 7.69 (d, 1H), 7.62 (d, 2H), 7.48 (d, 2H), 7.02 (d, 2H), 6.15 (s, 1H), 3.78 (s, 3H), 1.87 (s, 3H); LC-MS m/z calculated for [M+H]$^+$ 307.14. found 307.1.

Example 7

1-(2-(4-Fluorophenyl)thiazol-5-yl)-1-(pyridin-4-yl)ethanol

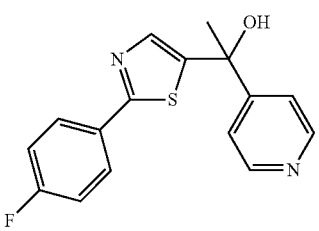 [SMILES: CC(O)(c1ccncc1)c1cnc(-c2ccc(F)cc2)s1]

A. Preparation A—According to the Synthetic Method of Schemes 1 and 2

Step 1: 2-(4-Fluorophenyl)thiazole-5-carbaldehyde

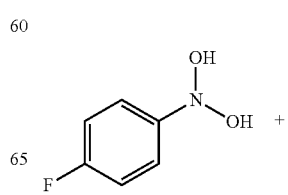

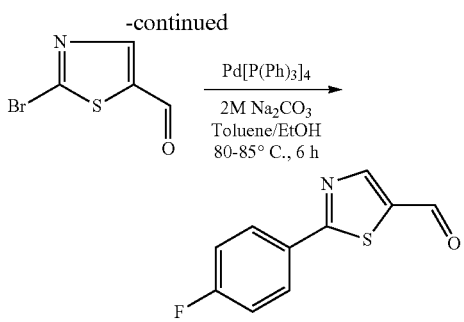

To a solution of 2-bromothiazole-5-carbaldehyde (5.0 g, 26.04 mmol) in toluene (150 mL) and ethanol (75 mL) was added (4-fluorophenyl)boronic acid (7.29 g, 52.08 mmol), 2M sodium carbonate solution (73.58 mL), Pd(PPh$_3$)$_4$ (1.5 g, 1.3 mmol) under argon atmosphere. The resulting mixture was heated at 85° C. for 6 h. The reaction mixture was concentrated under reduced pressure, the residue was diluted with water (150 mL), and extracted with ethyl acetate (5×500 mL). The organic layer was dried over Na$_2$SO$_4$, filtered and concentrated under reduced pressures to obtain crude product. The crude product was purified by Combiflash® chromatography (Mobile phase: 10% ethyl acetate in hexane) to give 2-(4-fluorophenyl)thiazole-5-carbaldehyde as off-white solid (200 mg, 88% yield). $^1$H NMR (400 MHz, DMSO-d$_6$): δ 10.06 (s, 1H), 8.74 (s, 1H), 8.14-8.11 (m, 2H), 7.39 (t, 2H); LC-MS m/z calculated for [M+H]$^+$ 208.02. found 207.9.

Step 2: 1-(2-(4-Fluorophenyl)thiazol-5-yl)ethanol

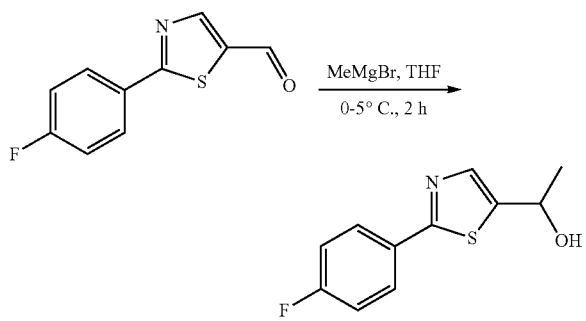

To a solution of 2-(4-fluorophenyl)thiazole-5-carbaldehyde (500 mg, 2.41 mmol) in THF (25 mL) was added 3M methyl magnesium bromide in ether (1.61 mL, 4.83 mmol) slowly at 0° C. The reaction mixture stirred for 1 hour at 0° C. and then at room temperature for about 1 hour. The reaction mixture was quenched with saturated NH$_4$Cl solution (25 mL), extracted with ethyl acetate (3×150 mL), the organic layer was dried over Na$_2$SO$_4$ and concentrated under reduced pressure to obtain crude product. The crude product was purified by flash chromatography (100-200μ; 30% ethyl acetate in hexane) to afford 1-(2-(4-fluorophenyl)thiazol-5-yl)ethanol as light yellow solid (420 mg, 78% yield). 1H NMR (400 MHz, DMSO-d$_6$): δ 7.93 (t, 2H), 7.67 (s, 1H), 7.30 (t, 2H), 5.71 (d, 1H), 5.01 (t, 1H), 1.45 (d, 3H); LC-MS m/z calculated for [M+H]$^+$ 224.05. found 224.4.

Step 3: 1-(2-(4-Fluorophenyl)thiazol-5-yl)ethanone

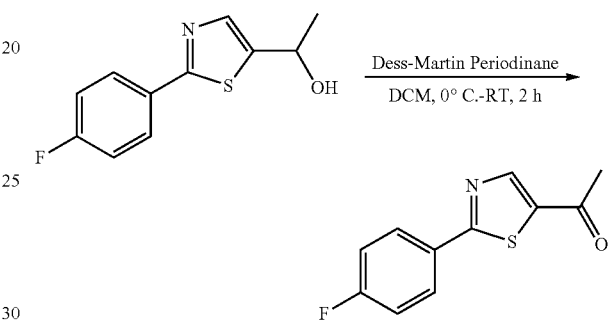

A solution of 1-(2-(4-fluorophenyl)thiazol-5-yl)ethanol (1.0 g, 4.4 mmol) in dichloromethane (40 mL) was cooled to 0° C. Dess-Martin periodinane (5.7 g, 13.4 mmol) was added slowly at 0° C. and the reaction mixture stirred at room temperature for 2 h. The reaction mixture was quenched with saturated NaHCO$_3$ solution (80 mL), sodium thiosulfate solution (20 mL), extracted with ether (2×1000 mL), the organic layer dried over Na$_2$SO$_4$, filtered and concentrated to obtain crude product. The crude product was purified by Combiflash® chromatography (40% ethyl acetate in hexane) to afford 1-(2-(4-fluorophenyl)thiazol-5-yl)ethanone as off-white solid (820 mg, 83% yield). 1H NMR (400 MHz, DMSO-d$_6$): δ 8.67 (s, 1H), 8.08 (t, 2H), 7.37 (t, 2H), 2.59 (s, 3H); LC-MS m/z calculated for [M+H]$^+$ 222.03. found 222.3.

Step 4: 1-(2-(4-Fluorophenyl)thiazol-5-yl)-1-(pyridin-4-yl)ethanol

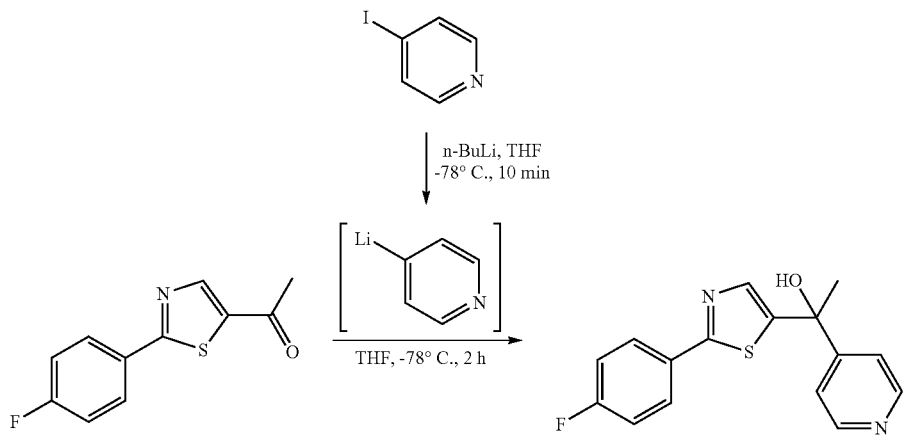

A solution 4-iodopyridine (1 g, 4.88 mmol) in THF (15 mL) was cooled to −78° C. under nitrogen, 1.6 M n-BuLi in hexane (0.565 mL, 8.14 mmol) was slowly added at −78° C. The reaction mixture was stirred for 10 min and 1-(2-(4-fluorophenyl)thiazol-5-yl)ethanone (900 mg, 4.07 mmol) in THF (25 mL) was added. The resulting mixture was stirred at −78° C. for 2 h. The reaction mixture was quenched with saturated NH$_4$Cl solution (160 mL), extracted with ethyl acetate (3×250 mL), the organic layer dried over Na$_2$SO$_4$, filtered and concentrated under reduced pressure to obtain crude product. The crude product was purified by flash chromatography (100-200μ; 70% ethyl acetate in hexane) to afford 1-(2-(4-fluorophenyl)thiazol-5-yl)-1-(pyridin-4-yl) ethanol as off-white solid (1.2 g, 35% yield) in 99.6% HPLC purity. 1H NMR (400 MHz, DMSO-d$_6$): δ 8.51 (d, 2H), 7.88-7.92 (m, 2H), 7.81 (s, 1H), 7.48 (d, 2H), 7.28 (t, 2H), 6.64 (s, 1H), 1.93 (s, 3H); LC-MS m/z calculated for [M+H]$^+$ 301.07. found 301.1.

B. Preparation B—According to the synthetic method of Scheme 3

Step 1: 2-(4-Fluorophenyl)thiazole

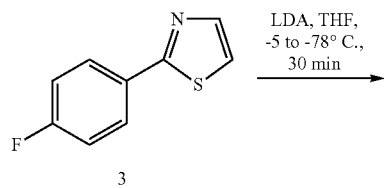

Using 2-bromothiazole (5.0 g, 30.482 mmol) and (4-fluorophenyl)boronic acid (8.528 g, 60.964 mmol) as reactants and following the procedure described in Example 7 step 1, the title compound was obtained after purification by flash chromatography (60-120μ; 4% ethyl acetate in hexane) as colorless liquid (5.0 g, 91% yield). 1H NMR (400 MHz, DMSO-d$_6$): δ 8.00-7.89 (m, 2H), 7.90 (d, 1H), 7.76 (d, 1H), 7.32 (t, 2H); LC-MS m/z calculated for [M+H]$^+$ 180.02. found 180.1.

Step 2: 1-(2-(4-Fluorophenyl)thiazol-5-yl)-1-(pyridin-4-yl)ethanol

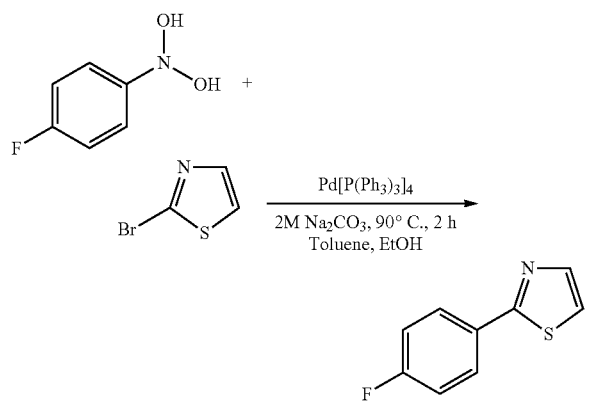

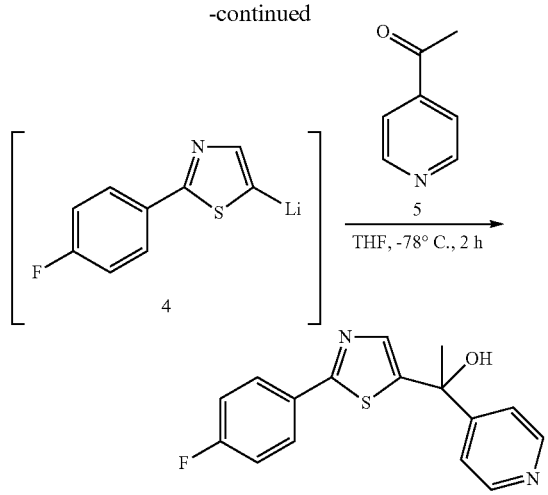

To a stirred solution of diisopropylamine (0.283 mL, 2.01 mmol) in THF (15 mL) at −78° C. under nitrogen atmosphere was added 1.6M n-BuLi in hexane (1.25 mL, 2.01 mmol) slowly. The reaction mixture was stirred for 30 min at −5° C., cooled to −78° C., 2-(4-fluorophenyl)thiazole (300 mg, 1.67 mmol) in THF (5 mL) added, and then 4-acetyl pyridine (300 mg, 1.67 mmol) in THF (5 mL) added. The resulting mixture was stirred at −78° C. for 2 h. The reaction mixture was quenched with saturated NH$_4$Cl solution (40 mL) and extracted with ethyl acetate (4×150 mL). The organic layer was dried over Na$_2$SO$_4$ and concentrated to obtain crude product. The crude product was purified by flash chromatography (100-200μ; 80% ethyl acetate in hexane) to afford 1-(2-(4-fluorophenyl)thiazol-5-yl)-1-(pyridin-4-yl)ethanol as off-white solid (285 mg, 57% yield), HPLC purity 99.9%, mp 229-232° C. 1H NMR (400 MHz, DMSO-d$_6$): δ 8.53 (d, 2H), 7.92 (t, 2H), 7.81 (s, 1H), 7.49 (d, 2H), 7.30 (t, 2H), 6.66 (s, 1H), 1.93 (s, 3H); LC-MS m/z calculated for [M+H]$^+$ 301.07. found 301.6.

HCl salt: To a suspension of 1-(2-(4-fluorophenyl)thiazol-5-yl)-1-(pyridin-4-yl)ethanol (2 g, 6.6 mmol) in ethanol (120 ml) was added 1,4-dioxane HCl (4 M, 1.66 mL, 6.6 mmol) slowly at 0° C., and then the mixture was stirred for 1 hour at room temperature. The solid that formed was filtered and washed with hexane (10 mL) to afford 4-(1-(1-(2-(4-fluorophenyl)thiazol-5-yl)-1-(pyridin-4-yl)ethanol hydrochloride as an off-white solid (1.6 g, 71% yield), HPLC purity 99.7%, mp 229-232° C. $^1$H NMR (400 MHz, DMSO-d$_6$): 8.81 (d, 2H), 8.04 (d, 2H), 7.92-7.89 (m, 3H), 7.29 (t, 2H), 7.13 (br s, 1H), 2.00 (s, 3H), LC-MS m/z calculated for [M+H]$^+$ 301.07. found 301.1.

4-Methylbenzenesulfonic acid salt: To a suspension of 1-(2-(4-fluorophenyl)-thiazol-5-yl)-1-(pyridin-4-yl)ethanol (2 g, 6.6 mmol) in ethanol (60 mL) was added 4-methylbenzenesulfonic acid (1.14 g, 6.6 mmol) slowly at 0° C., and then the mixture was stirred for 1 hour at room temperature. The solid that formed was filtered and washed with hexane (10 mL) to afford 4-(1-(1-(2-(4-fluorophenyl)thiazol-5-yl)-1-(pyridin-4-yl)ethanol 4-methylbenzenesulfonic acid salt as an off-white solid (1.9 g, 61% yield), HPLC purity 98.2%, mp 181-184° C. 1H NMR (400 MHz, DMSO-d$_6$): 8.84 (d, 2H), 8.08 (d, 2H), 7.91 (t, 3H), 7.46 (d, 2H), 7.30 (t, 2H), 7.09 (d, 2H), 2.26 (s, 3H), 2.01 (s, 3H); LC-MS m/z calculated for [M+H]$^+$ 301.07. found 301.1.

Benzenesulfonic acid salt: To a suspension of 1-(2-(4-fluorophenyl)thiazol-5-yl)-1-(pyridin-4-yl)ethanol (2 g, 6.6 mmol) in ethanol (60 mL) was added benzenesulfonic acid (1.05 g, 6.6 mmol) slowly at 0° C., and then the mixture was stirred for 1 hour at room temperature. The reaction mixture was concentrated, the solid obtained was washed with hexane (10 mL) to afford 4-(1-(1-(2-(4-fluorophenyl)thiazol-5-yl)-1-(pyridin-4-yl)ethanol benzenesulfonic acid salt as off-white solid (1.3 g, 43% yield), HPLC purity 99.6%, mp 165-167° C. 1H NMR (400 MHz, DMSO-d6): 8.81 (d, 2H), 8.04 (d, 2H), 7.93-7.89 (m, 3H), 7.57 (d, 2H), 7.33-7.28 (m, 5H), 7.09 (br s, 1H), 2.00 (s, 3H); LC-MS m/z calculated for [M+H]$^+$ 301.07. found 301.1.

Sulfuric acid salt: To a suspension of 1-(2-(4-fluorophenyl) thiazol-5-yl)-1-(pyridin-4-yl)ethanol (1 g, 3.3 mmol) in ethanol (25 mL) was added $H_2SO_4$ (0.18 mL, 3.3 mmol) slowly at 0° C., and then the mixture was stirred for 1 hour at room temperature. The solid that formed was filtered and washed with hexane (10 mL) to afford 4-(1-(2-(4-fluorophenyl)thiazol-5-yl)-1-hydroxyethyl)pyridin-1-ium hydrogen sulfate as an off-white solid (500 mg, 38% yield), HPLC purity 99.3%, mp 193-196° C. 1H NMR (400 MHz, DMSO-d$_6$): 8.82 (d, 2H), 8.05 (d, 2H), 7.93-7.89 (m, 3H), 7.29 (t, 2H), 7.13 (br s, 1H), 2.00 (s, 3H); LC-MS m/z calculated for [M+H]$^+$ 301.07. found 301.1.

Nitric acid salt: A suspension of 1-(2-(4-fluorophenyl)thiazol-5-yl)-1-(pyridin-4-yl)ethanol (2 g, 10 mmol) in ethanol (6 mL) and isopropyl alcohol (30 mL) was cooled to 0° C., and to this mixture was added 6N $HNO_3$ (6 mL) in 30 mL of isopropyl alcohol. The reaction mixture was stirred for 1 hour at room temperature. The solid formed was filtered and washed with hexane (10 mL) to afford 4-(1-(2-(4-fluorophenyl)thiazol-5-yl)-1-hydroxyethyl)pyridin-1-ium nitrate as an off-white solid (2.3 g, 63% yield), HPLC purity 99.8%, mp 188-191° C. 1H NMR (400 MHz, DMSO-d$_6$): 8.85 (d, 2H), 8.10 (d, 2H), 7.92 (t, 3H), 7.30 (t, 2H), 7.13 (br s, 1H), 2.01 (s, 3H); LC-MS m/z calculated for [M+H]$^+$ 301.07. found 301.1.

Example 11

1-(5-(4-Fluorophenyl)pyrazin-2-yl)-1-(pyridin-4-yl) ethanol (Synthetic Method of Scheme 4)

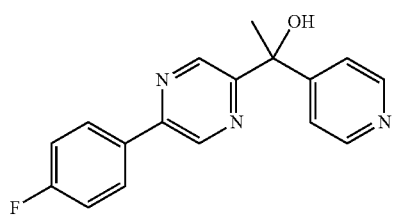 [SMILES: CC(O)(c1ccncc1)c1cnc(-c2ccc(F)cc2)cn1]

Step 1: 2-Bromo-5-(4-fluorophenyl)pyrazine

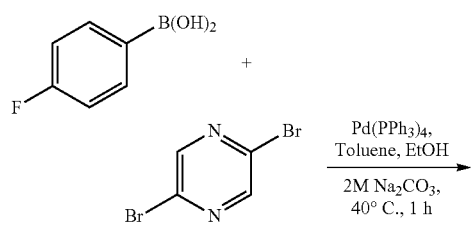

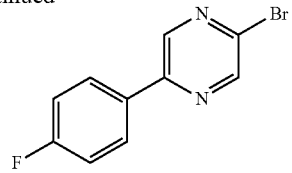

To a solution of 2,5-dibromopyrazine (100 mg, 0.4 mmol) in toluene (6 mL) and ethanol (3 mL) was added (4-fluorophenyl)boronic acid (29 mg, 0.2 mmol) and 2M sodium carbonate solution (2.84 mL). The solution was purged with argon for 15 min, Pd(PPh$_3$)$_4$ (4 mg, 0.004 mmol) was added, and the reaction mixture was purged with argon for 15 min. The resulting mixture was heated to 40° C. and stirred for 1 h. The reaction mixture was concentrated, diluted with water (20 mL), and extracted with ethyl acetate (2×100 mL). The combined extracts were washed with brine solution (10 mL), and dried over Na$_2$SO$_4$ and concentration in vacuo. The crude product was purified by flash chromatography (60-120µ, 5% ethyl acetate in hexane) to afford 2-bromo-5-(4-fluorophenyl)pyrazine as off-white solid (60 mg, 57% yield). 1H NMR (400 MHz, DMSO-d$_6$): δ 9.08 (s, 1H), 8.88 (s, 1H), 8.18-8.15 (m, 2H), 7.37 (dd, 2H); LC-MS m/z calculated for [M+H]$^+$ 252.97. found 253.0.

Step 2: 1-(5-(4-Fluorophenyl)pyrazin-2-yl)-1-(pyridin-4-yl)ethanol

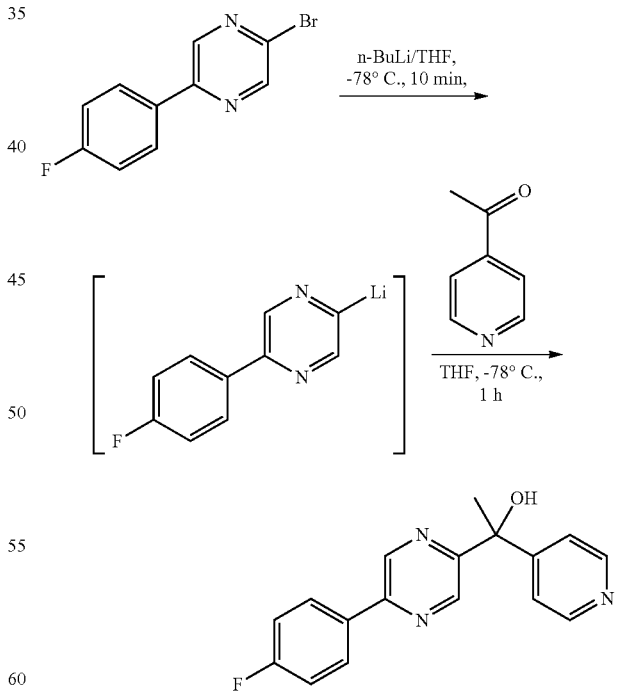

2-bromo-5-(4-fluorophenyl)pyrazine (115 mg, 0.4 mmol) in THF (10 mL) was cooled to −78° C., 1.6 M n-BuLi in hexane (0.56 mL, 0.8 mmol) added slowly at −78° C., the reaction mixture was stirred for 10 min at −78° C., and 1-(pyridin-4-yl)ethanone (54 mg, 0.4 mmol) in THF (3 mL) was added. The resulting mixture was stirred at −78° C. for 1 h. The reaction mixture was quenched with saturated NH₄Cl solution (10 mL) and extracted with ethyl acetate (2×200 mL). The combined extracts were washed with brine solution (20 mL), dried over Na₂SO₄, filtered and concentrated under vacuum to obtain crude product. The crude product was purified by preparative TLC (mobile phase: 60% ethyl acetate in hexane) to afford 1-(5-(4-fluorophenyl)pyrazin-2-yl)-1-(pyridin-4-yl)ethanol as off-white solid (32 mg, 24% yield) in 98.7% HPLC purity. 1H NMR (400 MHz, DMSO-d₆): δ 9.13 (s, 1H), 8.93 (s, 1H), 8.48 (d, 2H), 8.16-8.13 (m, 2H), 7.49 (d, 2H), 7.34 (t, 2H), 6.43 (s, 1H), 1.90 (s, 3H); LC-MS m/z calculated for [M+H]⁺ 296.11. found 296.1.

Example 12

6'-(1-Hydroxy-1-(pyridin-4-yl)ethyl)-[3,3'-bipyridine]-6-carbonitrile (Synthetic Method of Scheme 1)

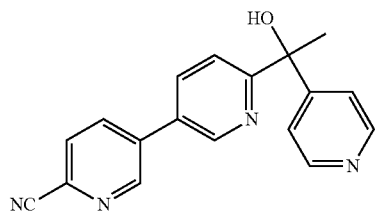 [SMILES: CC(O)(c1ccncc1)c1ccc(-c2ccc(C#N)nc2)cn1]

Step 1: 6'-Acetyl-[3,3'-bipyridine]-6-carbonitrile

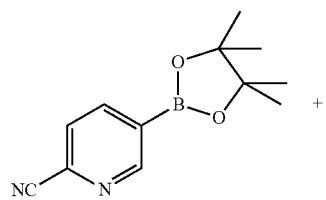 +

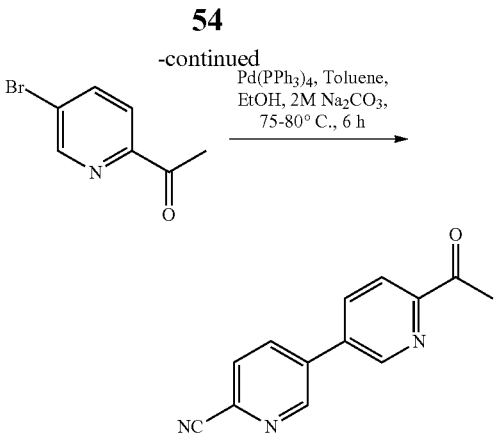

To a stirred solution of 1-(5-bromopyridin-2-yl)ethanone (0.2 g, 1 mmol) in toluene (10 mL) and ethanol (5 mL) was added 5-(4,4,5,5-tetramethyl-1,3,2-dioxaborolan-2-yl)picolinonitrile (0.46 g, 2 mmol) and Pd(PPh₃)₄ (0.057 g, 0.05 mmol). The reaction mixture was purged with argon for 5 min, 2M Na₂CO₃ solution (3.5 mL, 0.74 g, 7 mmol) was added, and the reaction mixture was stirred at 75-80° C. for 6 h. The reaction mixture was cooled to room temperature, quenched with saturated sodium bicarbonate solution (2×100 mL), and extracted into ethyl acetate (2×100 mL). The organic layer was washed with brine and ice-cold water (2×100 mL), dried over sodium sulfate, filtered and concentrated under reduced pressure to obtain crude product. The crude product was purified by column chromatography (100-200µ silica gel, using 15-16% ethyl acetate in hexane) to obtain 6'-acetyl-[3,3'-bipyridine]-6-carbonitrile as white solid (0.18 g, 80% yield). 1H NMR (400 MHz, DMSO-d₆): δ 9.24 (dd, 1H), 9.20 (dd, 1H), 8.54 (dd, 1H), 8.46 (dd, 1H), 8.23 (dd, 1H), 8.09 (dd, 1H), 2.68 (s, 3H); LC-MS m/z calculated for [M+H]⁺ 224.07. found 224.1.

Step 2: 6'-(1-Hydroxy-1-(pyridin-4-yl)ethyl)-[3,3'-bipyridine]-6-carbonitrile

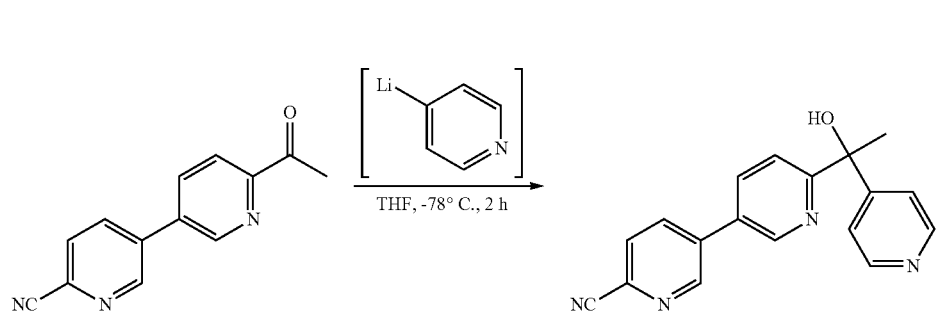

Using 4-iodo pyridine (0.22 g, 1.076 mmol), and 6'-acetyl-[3,3'-bipyridine]-6-carbonitrile (0.12 g, 0.54 mmol) and procedure described for example 7 and step 4, crude product was obtained. The crude product was purified by preparative TLC (5% methanol in ethyl acetate) to obtain 6'-(1-hydroxy-1-(pyridin-4-yl)ethyl)-[3,3'-bipyridine]-6-carbonitrile as off-white solid (30 mg, 18% yield) in 98% HPLC purity. 1H NMR (400 MHz, DMSO-$d_6$): δ 9.12 (s, 1H), 8.94 (s, 1H), 8.46 (d, 2H), 8.38 (dd, 1H), 8.23 (dd, 1H), 8.14 (d, 1H), 7.82 (d, 1H), 7.49 (d, 2H), 6.27 (s, 1H), 1.9 (s, 3H); LC-MS m/z calculated for [M+H]$^+$ 303.12. found 303.1.

Example 13

1-(5-(4-Fluorophenyl)thiazol-2-yl)-1-(pyridin-4-yl)propan-1-ol (Synthetic Method of Scheme 7)

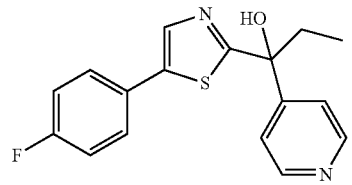 [SMILES: CCC(O)(c1ccncc1)c1ncc(-c2ccc(F)cc2)s1]

Step 1: 5-(4-Fluorophenyl)thiazole

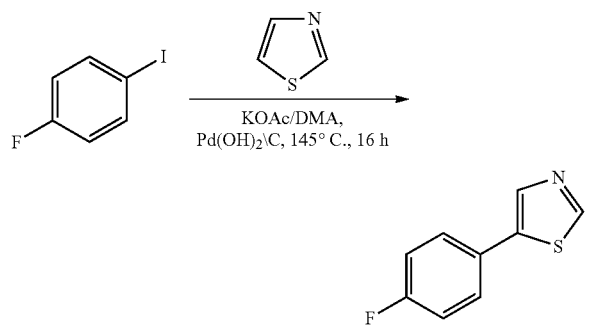

To a sealed tube containing a solution of thiazole (2 g, 23.53 mmol) in DMA (10 mL) was added potassium acetate (6.9 g, 70.58 mmol), 1-fluoro-4-iodobenzene (15.6 g, 70.58 mmol), and palladium hydroxide\C (0.53 g, 2.35 mmol) under nitrogen. The reaction mixture was heated to 145° C. and stirred for 16 h. The reaction mixture was cooled to room temperature and diluted with water (200 mL), filtered through Celite® reagent, and extracted with ethyl acetate (300 mL). The organic layer was dried over sodium sulfate, filtered and concentrated under reduced pressure to obtain crude product. The crude product was purified by column chromatography (100-200μ silica gel, eluting with 10% EtOAc and hexane) to afford 5-(4-fluorophenyl)thiazole (0.9 g, 22%). 1H NMR (400 MHz, CDCl$_3$): δ 8.74 (s, 1H), 8.01 (s, 1H), 7.55 (t, 2H), 7.11 (t, 2H).

Step 2: 5-(4-Fluorophenyl)thiazole-2-carbaldehyde

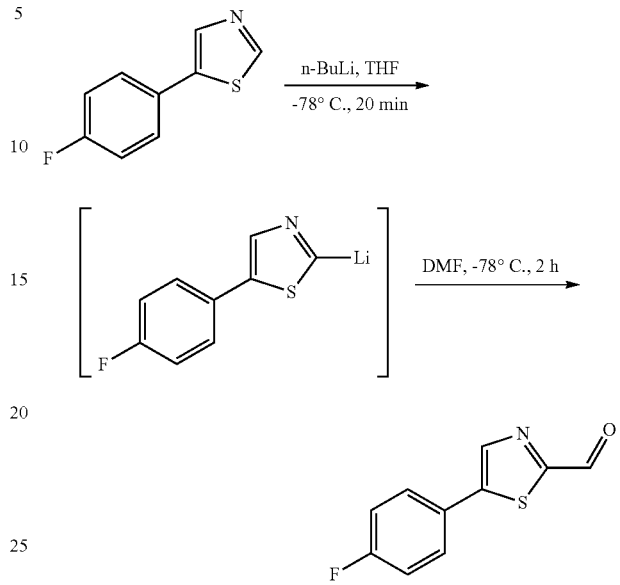

A solution of 5-(4-fluorophenyl)thiazole (0.5 g, 2.78 mmol) and THF (40 mL) was cooled to −78° C., 1.6 M n-BuLi in hexanes (0.7 mL, 8.36 mmol) was slowly added, the solution was stirred for 20 min and DMF in THF (20 mL) was added. The reaction mixture was stirred at −78° C. for 2 h, quenched with saturated ammonium chloride solution and diluted with ethyl acetate (150 mL). The organic layer was separated, washed with ammonium chloride (3×150 mL) and followed by brine solution (2×100 mL). The organic layer was dried over sodium sulfate, filtered and concentrated under reduced pressure to obtain crude product. The crude product was purified by column chromatography (100-200μ silica gel and 18% ethyl acetate in hexane) to obtain 5-(4-fluorophenyl)thiazole-2-carbaldehyde as off-white solid (0.4 g, 69% yield). 1H NMR (400 MHz, DMSO-$d_6$): δ 9.91 (s, 1H), 8.63 (s, 1H), 7.88-7.91 (m, 2H), 7.35 (t, 2H), LC-MS m/z calculated for [M+H]$^+$ 208.02 found 208.1.

Step 3: 1-(5-(4-Fluorophenyl)thiazol-2-yl)propan-1-ol

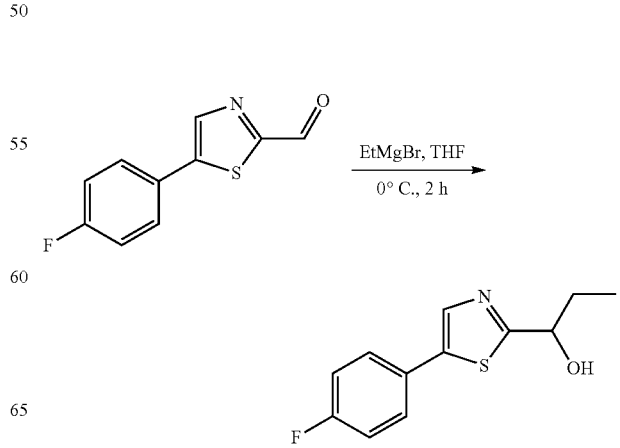

Using 5-(4-fluorophenyl)thiazole-2-carbaldehyde (0.12 g, 0.58 mmol) and EtMgBr (0.577 mL, 1.73 mmol) and following the procedure described for example 7 and step 2, the crude compound was obtained and further purified by column chromatography (using 100-200μ silica gel and 38% ethyl acetate and hexane) to give 1-(5-(4-fluorophenyl)thiazol-2-yl)propan-1-ol as pale yellow liquid (0.1 g, 73% yield). 1H NMR (400 MHz, DMSO-d$_6$): δ 8.01 (s, 1H), 7.68-7.65 (m, 2H), 7.25 (t, 2H), 6.11 (d, 1H), 4.72-4.67 (m, 1H), 1.84 (m, 1H), 1.88-1.67 (m, 1H), 0.91 (t, 3H); LC-MS m/z calculated for [M+H]$^+$ 238.06. found 238.5.

Step 4: 1-(5-(4-Fluorophenyl)thiazol-2-yl)propan-1-one

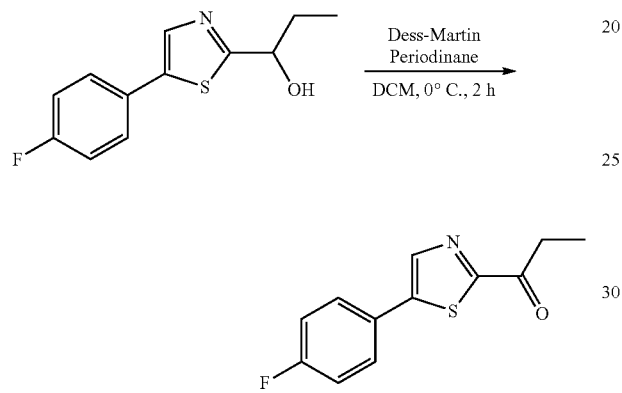

1-(5-(4-fluorophenyl)thiazol-2-yl)propan-1-ol (0.05 g, 0.21 mmol) was oxidized using the procedure described for example 7 and step 3 to provide 1-(5-(4-fluorophenyl)thiazol-2-yl)propan-1-one after column chromatography purification (100-200μ silica gel and 15% ethyl acetate in hexane) as off-white solid (40 mg, 81% yield). 1H NMR (400 MHz, DMSO-d$_6$): δ 8.49 (s, 1H), 7.89-7.85 (m, 2H), 7.35 (t, 2H), 3.13 (q, 2H), 1.13 (t, 3H); LC-MS m/z calculated for [M+H]$^+$ 236.05. found 236.1.

Step 5: 1-(5-(4-Fluorophenyl)thiazol-2-yl)-1-(pyridin-4-yl)propan-1-ol

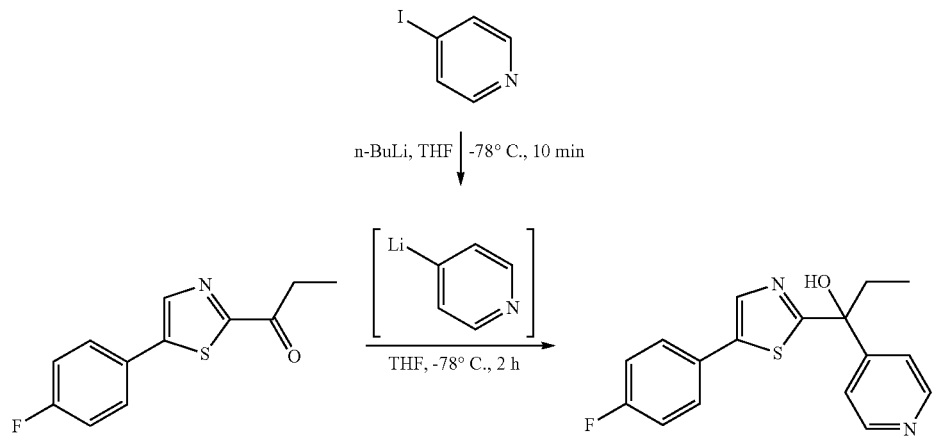

Using 1-(5-(4-fluorophenyl)thiazol-2-yl)-1-(pyridin-4-yl)propan-1-ol (0.04 g, 0.17 mmol) and 4-iodopyridine (0.069 g, 0.34 mmol) and following the procedure described for example 7 and step 4, crude compound was obtained and was further purified by preparative TLC (5% methanol in dichloromethane) to give 1-(5-(4-fluorophenyl)thiazol-2-yl)-1-(pyridin-4-yl)propan-1-ol (14 mg, 10% yield) in 95% HPLC purity. 1H NMR (400 MHz, DMSO-d$_6$): δ 8.52-8.49 (m, 2H), 8.05 (s, 1H), 7.65-7.62 (m, 2H), 7.56 (d, 2H), 7.23 (t, 2H), 6.81 (br s, 1H), 2.34-2.24 (m, 2H), 0.77 (t, 3H); LC-MS m/z calculated for [M+H]$^+$ 315.09. found 315.1.

Example 14

1-(5-(4-Fluorophenyl)thiazol-2-yl)-1-(pyridin-4-yl)ethanol (Synthetic Method of Scheme 3)

Step 1: 5-(4-Fluorophenyl)thiazole

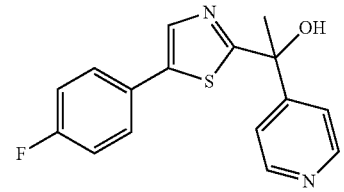 [SMILES: CC(O)(c1ccncc1)c1ncc(-c2ccc(F)cc2)s1]

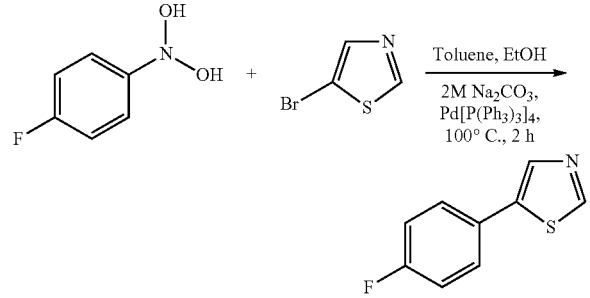

Using 5-bromothiazole (1.0 g, 6.09 mmol) and (4-fluorophenyl)boronic acid (1.0 g, 7.31 mmol) and following the procedure described in example 7 step 1, the title compound was obtained after purification by purified by Biotage IsoleraOne® column (10% ethyl acetate in hexane) as yellow viscous liquid (0.4 g, 36% yield). 1H NMR (400 MHz, DMSO-$d_6$): δ 9.05 (s, 1H), 8.25 (s, 1H), 7.73-7.69 (m, 2H), 7.27 (t, 2H); LC-MS m/z calculated for [M+H]$^+$ 180.02. found 180.1.

Step 2: 1-(5-(4-Fluorophenyl)thiazol-2-yl)-1-(pyridin-4-yl)ethanol

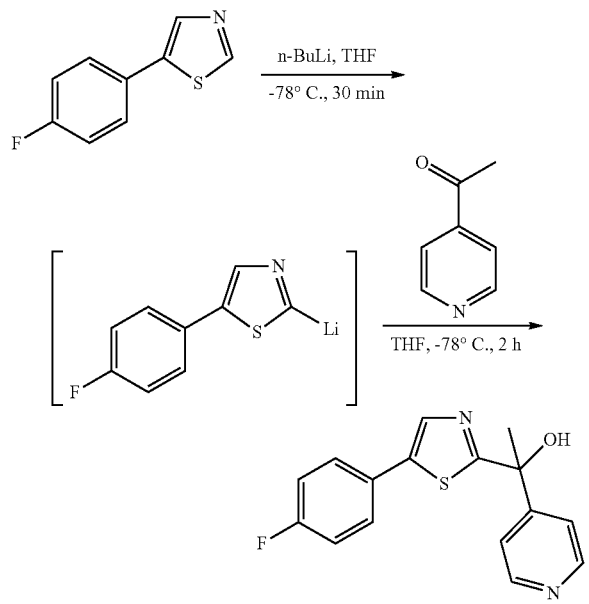

To a solution of 5-(4-fluorophenyl)thiazole (0.1 g, 0.558 mmol) in dry THF (8 mL) at −78° C., was slowly added n-1.6 M BuLi in hexanes (0.7 mL, 1.117 mmol), the reaction mixture was stirred for 30 minutes and 1-(pyridin-4-yl)ethanone (0.13 mL, 1.117 mmol) in THF (8 mL) was added. The reaction mixture was stirred for 2 hours at −78° C., the reaction mixture quenched with saturated NH$_4$Cl solution (50 mL), extracted with EtOAc (2×50 mL), the organic layer washed with water (50 mL), dried over Na$_2$SO$_4$ and concentrated under reduced pressure to obtain crude product. The crude product was purified by preparative TLC (5% methanol in dichloromethane) to give 1-(5-(4-fluorophenyl)thiazol-2-yl)-1-(pyridin-4-yl)ethanol as off-white solid (35 mg, 22% yield) in 99.6% HPLC purity. 1H NMR (400 MHz, DMSO-$d_6$): δ 8.50 (br s, 1H), 8.03 (s, 1H), 7.66-7.63 (m, 2H), 7.53 (br s, 2H), 7.24 (t, 2H), 6.99 (s, 1H), 1.89 (s, 3H); LC-MS m/z calculated for [M+H]$^+$ 301.07. found 301.4.

Example 15

5-(5-(1-Hydroxy-1-(pyridin-4-yl)ethyl)thiophen-2-yl)-1-methylpyridin-2(1H)-one (Synthetic Method of Scheme 6)

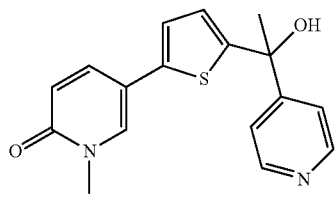 [SMILES: Cn1cc(-c2ccc(C(C)(O)c3ccncc3)s2)ccc1=O]

Step 1: 5-Bromo-2-methoxypyridine

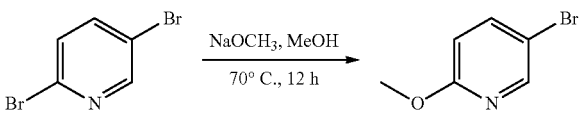

A mixture of 2,5-dibromopyridine (5.5 g, 23.2 mmol) and NaOMe (3.76 g, 69.6 mmol) in MeOH (60 mL) was heated at 70° C. for 1 hour and then allowed to cool to room temperature. The reaction mixture was diluted with water (50 mL) and extracted with EtOAc (2×100 mL). The combined organic layers were dried over Na$_2$SO$_4$ and concentrated under reduced pressure to give a pale yellow volatile oil (2.5 g, 58% yield). 1H NMR (400 MHz, DMSO-$d_6$): δ 8.26 (s, 1H), 7.87 (dd, 1H), 6.81 (d, 1H), 3.82 (s, 3H).

Step 2: 5-Bromopyridin-2(1H)-one

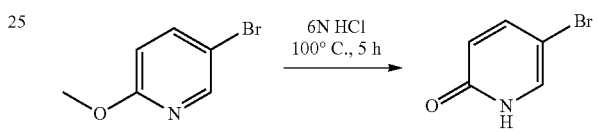

5-bromo-2-methoxypyridine (2.5 g, 13.29 mmol) was dissolved in 6N HCl (30 mL). The solution was heated at 100° C. and stirred for 5 h. The reaction mixture was cooled to 5° C. and the pH of the reaction mixture was adjusted to 6.5 with 10% aqueous NaOH. The precipitate was collected by filtration, washed with water (100 mL), and dried under vacuum to obtain 5-bromopyridin-2(1H)-one (1.5 g, 65% yield). 1H NMR (400 MHz, CDCl$_3$): δ 10.2-8.2 (br s, 1H) 7.52-7.49 (m, 2H), 6.51 (d, 1H); LC-MS m/z calculated for [M+H]$^+$ 173.95. found 173.8.

Step 3: 5-Bromo-1-methylpyridin-2(1H)-one

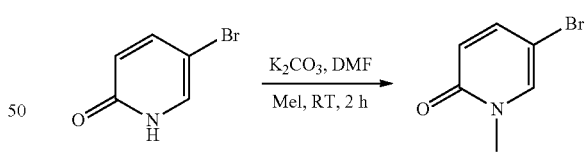

To a solution of 5-bromopyridin-2(1H)-one (0.18 g, 1.03 mmol) in DMF (5 mL) was added iodomethane (0.2 mL, 3.1 mmol) and potassium carbonate (0.8 g, 6.2 mmol). The reaction mixture was stirred at room temperature for 2 h. The reaction mixture was then concentrated under reduced pressure, the residue dissolved in ethyl acetate (200 mL), washed with water (50 mL) and brine solution. The organic layers were combined and dried over sodium sulfate, filtered and concentrated under vacuum to afford 5-bromo-1-methylpyridin-2(1H)-one [Albrecht, US Patent Application Publication No. 2009/0318436] as yellow solid (40 mg, 21%). 1H NMR (DMSO-$d_6$): δ 8.01 (d, 1H), 7.49 (dd, 1H), 6.34 (d, 1H), 3.38 (s, 3H); LC-MS m/z calculated for [M+H]$^+$ 187.96. found 188.2.

Step 4: 5-(5-Acetylthiophen-2-yl)-1-methylpyridin-2(1H)-one

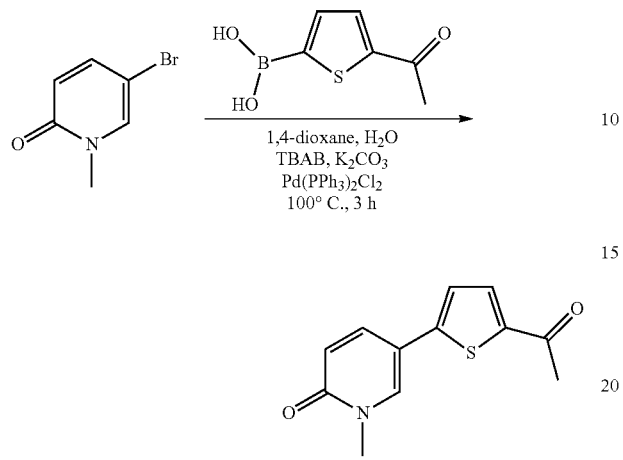

To a solution of 5-bromo-1-methylpyridin-2(1H)-one (0.2 g, 1.06 mmol) in 1,4-dioxane (5 mL) and water (2 mL), (5-acetylthiophen-2-yl)boronic acid (0.2 g, 1.27 mmol), tetrabutyl ammonium bromide (0.034 g, 0.16 mmol), $K_2CO_3$ (0.4 mL, 3.19 mmol) and $Pd(PPh_3)_2Cl_2$ (0.18 g, 1.59 mmol) were added under argon. The mixture was purged with argon for 10 min and heated to 100° C. for 1 h. The reaction mixture was filtered through Celite® reagent, the filtrate concentrated, the residue extracted with EtOAc (2×100 mL), and washed with water (100 mL). The organic layer was dried over $Na_2SO_4$, filtered and concentrated under reduced pressure to obtain crude product. The crude product was purified by Biotage IsoleraOne® column purifier (80% ethyl acetate in hexane) and obtained as yellow viscous liquid (0.15 g, 62% yield). 1H NMR (400 MHz, $CDCl_3$): δ 7.69-7.58 (m, 3H), 7.08 (d, 1H), 6.65 (d, 1H), 3.61 (s, 3H), 2.54 (s, 3H); LC-MS m/z calculated for $M+H^+$ 234.05. found 234.1.

Step 5: 5-(5-(1-Hydroxy-1-(pyridin-4-yl)ethyl)thiophen-2-yl)-1-methylpyridin-2(1H)-one

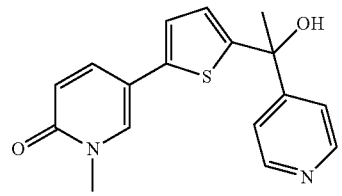

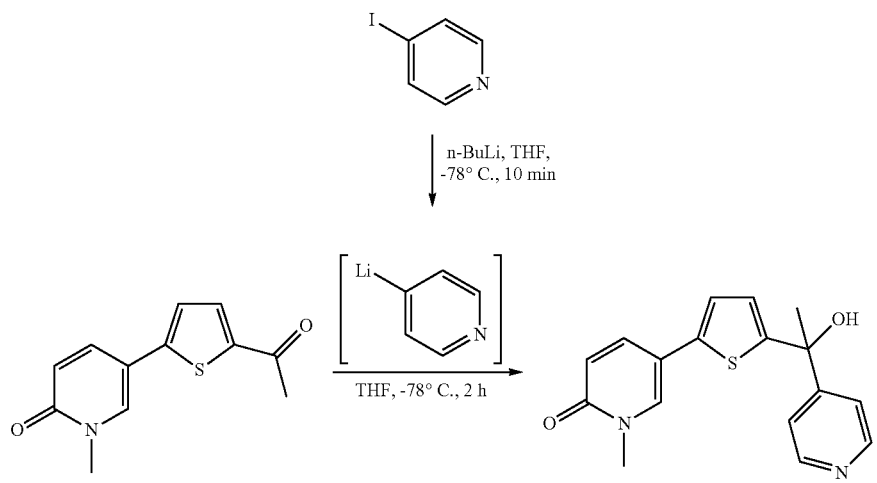

Using 5-(5-acetylthiophen-2-yl)-1-methylpyridin-2(1H)-one (0.07 g, 0.3 mmol), 4-iodopyridine (0.12 g, 0.6 mmol), and the procedure described for example 7 and step 4, crude compound was obtained and further purified by preparative TLC (5% methanol in dichloromethane) to give 5-(5-(1-hydroxy-1-(pyridin-4-yl)ethyl)thiophen-2-yl)-1-methylpyridin-2(1H)-one as off-white solid (0.02 g, 21% yield) in 99.8% HPLC purity. 1H NMR (400 MHz, DMSO-$d_6$): δ 8.48 (d, 2H), 7.97 (d, 1H), 7.65 (dd, 1H), 7.45-7.44 (t, 2H), 7.07 (d, 1H), 6.94 (d, 1H), 6.41-6.38 (m, 2H), 3.42 (s, 3H), 1.85 (s, 3H); LC-MS m/z calculated for $[M+H]^+$ 313.09. found 313.1.

Examples 16 & 17

Enantiomer #1 and Enantiomer #2 of 5-(5-(1-hydroxy-1-(pyridin-4-yl)ethyl)thiophen-2-yl)-1-methylpyridin-2(1H)-one Racemic 5-(5-(1-hydroxy-1-(pyridin-4-yl)ethyl)thiophen-2-yl)-1-methylyridin-2(1H)-one (530 mg) was subjected to chiral HPLC purification using Chiralpak® IC [250 mm×4.6 mm×5 µm column, mobile phase: n-heptane:ethanol with 0.1% DEA (50:50); flow rate: 1 mL/min] to afford about 150 mg (56% recovery) (+)-5-(5-(1-hydroxy-1-(pyridin-4-yl)ethyl)thiophen-2-yl)-1-methylpyridin-2(1H)-one (Enantiomer #1; $[α]_D^{25}$+ 68.8 (c 1.0, MeOH)) and 150 mg (56% recovery) of (−)-5-(5-(1-hydroxy-1-(pyridin-4-yl)ethyl)thiophen-2-yl)-1-methylpyridin-2(1H)-one (Enantiomer #2; $[α]_D^{25}$−65.7 (c 1.0, MeOH)), each enantiomer isolated with 99.9% ee. For each enantiomer: 1H NMR (400 MHz, DMSO-$d_6$): δ 8.48 (d, 2H), 7.98 (d, 1H), 7.66 (dd, 1H), 7.45 (d, 2H), 7.07 (d, 1H), 6.95 (d, 1H), 6.41 (s, 1H), 6.39 (s, 1H), 3.42 (s, 3H), 1.86 (s, 3H); LC-MS m/z calculated for $[M+H]^+$ 313.09. found 313.6.

Example 18

1-(2-(1H-Pyrazol-4-yl)thiazol-5-yl)-1-(pyridin-4-yl)propan-1-ol

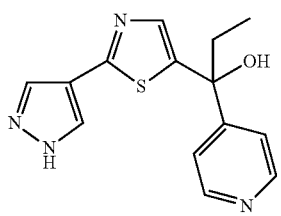 [SMILES: CCC(O)(c1ccncc1)c1cnc(-c2cn[nH]c2)s1]

A. Preparation A—According to the Synthetic Method of Schemes 1 and 2

Step 1: 2-(1H-Pyrazol-4-yl)thiazole-5-carbaldehyde

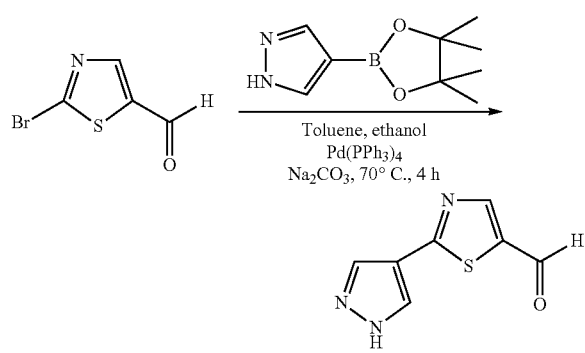

To a solution of 2-bromothiazole-5-carbaldehyde (500 mg, 2.6 mmol) in toluene (15 mL) and ethanol (7 mL) was added 4-(4,4,5,5-tetramethyl-1,3,2-dioxaborolan-2-yl)-1H-pyrazole (606 mg, 3.1 mmol), 2M sodium carbonate solution (7.3 mL) and Pd(PPh$_3$)$_4$ (30 mg, 0.02 mmol). The reaction mixture was purged with argon for 15 min and the resulting mixture was heated at 70° C. for 4 h. The reaction mixture was concentrated, diluted with water (100 mL), and extracted with ethyl acetate (2×200 mL). The combined extracts were washed with brine solution (20 mL), dried over Na$_2$SO$_4$, filtered and concentrated to under vacuum to obtain crude product. The crude product was purified by flash chromatography (60-120μ; 50% ethyl acetate in hexane) to afford 2-(1H-pyrazol-4-yl)thiazole-5-carbaldehyde as yellow solid (250 mg, 54% yield). 1H NMR (400 MHz, DMSO-d$_6$): δ 13.49 (br s, 1H), 10.00 (s, 1H), 8.61 (s, 1H), 8.55 (s, 1H), 8.09 (s, 1H); LC-MS m/z calculated for [M+H]$^+$ 180.02. found 180.1.

Step 2: 1-(2-(1H-Pyrazol-4-yl)thiazol-5-yl)propan-1-ol

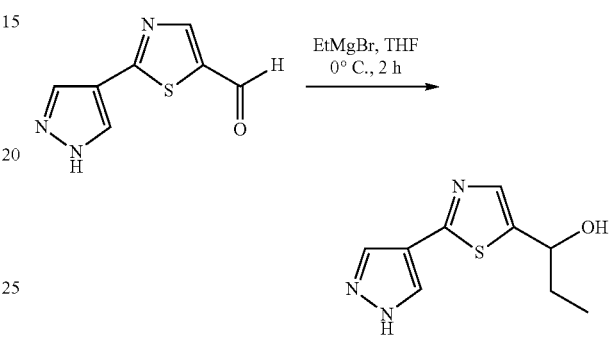

A solution of 2-(1H-pyrazol-4-yl)thiazole-5-carbaldehyde (245 mg, 1.3 mmol) in THF (15 mL) was cooled to 0° C., a 3M solution of ethyl magnesium bromide in diethyl ether (0.9 mL, 2.7 mmol) slowly added at 0° C., and the reaction mixture stirred for 2 hours at 0° C. The reaction mixture was quenched with saturated NH$_4$Cl solution (10 mL) and extracted with ethyl acetate (2×200 mL). The combined extracts were washed with brine solution (20 mL), dried over Na$_2$SO$_4$, filtered and the organic solvent was concentrated under reduced pressure to obtain crude product. The crude product was purified by flash chromatography (60-120μ; 3% methanol in dichloromethane) to afford 1-(2-(1H-pyrazol-4-yl)thiazol-5-yl)propan-1-ol as pale yellow liquid (180 mg, 63% yield). 1H NMR (400 MHz, DMSO-d$_6$): δ 13.19 (br s, 1H), 8.25 (s, 1H), 7.88 (s, 1H), 7.51 (s, 1H), 5.59 (d, 1H), 4.71 (q, 1H), 1.97-1.64 (m, 2H), 0.86 (t, 3H); LC-MS m/z calculated for [M+H]$^+$ 210.06. found 210.1.

Step 3: 1-(2-(1H-Pyrazol-4-yl)thiazol-5-yl)-1-(pyridin-4-yl)propan-1-ol

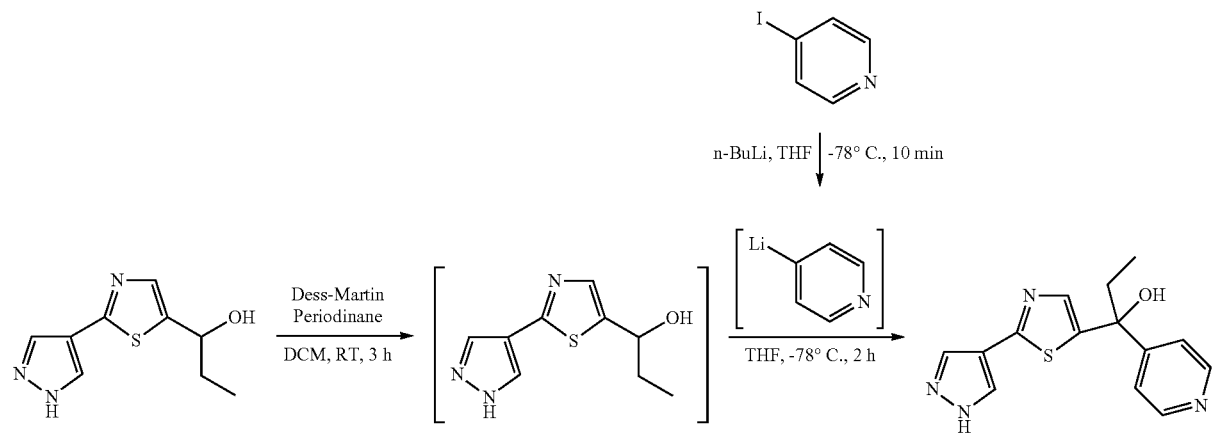

A solution of 1-(2-(1H-pyrazol-4-yl)thiazol-5-yl)propan-1-ol (175 mg, 0.83 mmol) in dichloromethane (15 mL) was cooled to 0° C. add DessMartin Periodinane (1.06 g, 2.51 mmol) was slowly added at 0° C. The reaction mixture was allowed to stir at room temperature for about 3 h, quenched with saturated NaHCO₃ solution (10 mL), followed by sodium thiosulfate solution (5 mL), and extracted with dichloromethane (2×200 mL). The combined extracts were washed with brine solution (10 mL), the organic layer was dried over Na₂SO₄, filtered and concentrated under reduced pressure. The residue was subjected to a small filter column, the product 1-(2-(1H-pyrazol-4-yl)thiazol-5-yl)propan-1-one (140 mg) confirmed by LC-MS and then used for the next step. LC-MS m/z calculated for [M+H]⁺ 208.05. found 208.1.

A solution of 4-iodopyridine (133 mg, 0.65 mmol) in THF (15 mL) was cooled to −78° C., 1.6 M n-BuLi in hexane (0.81 mL, 1.3 mmol) slowly added at −78° C., the reaction mixture stirred for 20 min at −78° C., and 1-(2-(1H-pyrazol-4-yl)thiazol-5-yl)propan-1-one (135 mg, 0.65 mmol) in THF (5 mL) added. The resulting mixture was stirred at −78° C. for 2 h. The reaction mixture was quenched with saturated NH₄Cl solution (10 mL) and extracted with ethyl acetate (2×250 mL). The combined extracts were washed with brine solution (10 mL), dried over Na₂SO₄, filtered and concentrated under reduced pressure to obtain crude product. The crude product was purified by preparative TLC (mobile phase: 5% methanol in dichloromethane) to afford 1-(2-(1H-pyrazol-4-yl)thiazol-5-yl)-1-(pyridin-4-yl)propan-1-ol as pale yellow liquid (13 mg, 5% yield) in 99.4% HPLC purity. 1H NMR (400 MHz, DMSO-d₆): δ 13.19 (br s, 1H), 8.51 (d, 2H), 8.24 (br s, 1H), 7.87 (br s, 1H), 7.65 (s, 1H), 7.45 (d, 2H), 6.29 (s, 1H), 2.32-2.23 (m, 2H), 0.77 (t, 3H); LC-MS m/z calculated for [M+H]⁺ 287.09. found 287.1.

B. Preparation B—According to the Synthetic Method of Scheme 3

Step 1: 2-(1H-Pyrazol-4-yl)thiazole

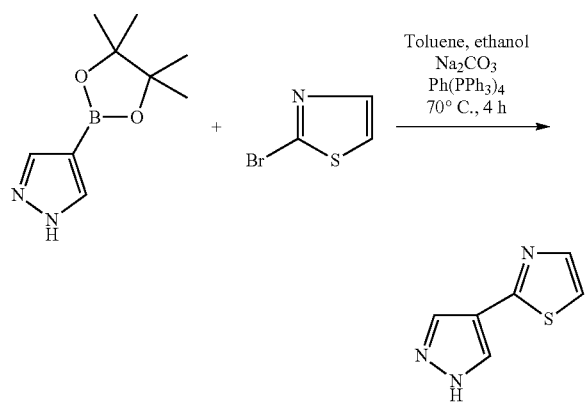

To a solution of 2-bromothiazole (1 g, 6 mmol) in toluene (20 mL) and ethanol (10 mL) was added 4-(4,4,5,5-tetramethyl-1,3,2-dioxaborolan-2-yl)-1H-Pyrazole (1.41 g, 7.3 mmol), 2 M sodium carbonate solution (17.3 mL) and Pd(PPh₃)₄ (7 mg, 0.06 mmol). The reaction mixture was purged with argon for 15 min. The resulting mixture was heated at 70° C. for 4 h. The reaction mixture was concentrated and diluted with water (100 mL), extracted with ethyl acetate (2×200 mL). The combined extracts were washed with brine solution (20 mL), the organic solvent was dried over Na₂SO₄, filtered and concentrated under reduced pressure to obtain crude product. The crude product was purified by flash chromatography (60-120μ; 50% ethyl acetate in hexane) to afford racemic 2-(1H-pyrazol-4-yl)thiazole as brown liquid (520 mg, 56% yield). 1H NMR (400 MHz, DMSO-d₆): δ 13.22 (br s, 1H), 8.30 (s, 1H), 7.93 (s, 1H), 7.73 (s, 1H), 7.55 (d, 1H); LC-MS m/z calculated for [M+H]⁺ 152.02. found 152.1.

Step 2: 1-(2-(1H-Pyrazol-4-yl)thiazol-5-yl)-1-(pyridin-4-yl)propan-1-ol

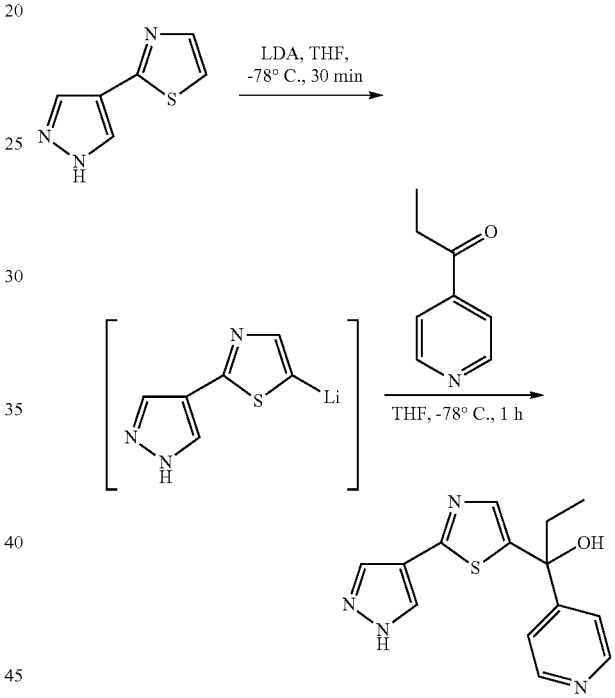

To a stirred solution of diisopropylamine (0.28 mL, 1.9 mmol) in THF (10 mL) at −60° C. was added n-BuLi (1.6 M, 2.48 mL) slowly. The reaction mixture was stirred for 30 min at −10° C., cooled to −78° C., and a solution 2-(1H-pyrazol-4-yl)thiazole (200 mg, 1.3 mmol) in THF (5 mL) added dropwise for 30 minutes. 4-Acetyl pyridine (0.07 mL, 0.000674 mmol) in THF (2 mL) was then added and the reaction mixture stirred for additional 1 hour at −78° C. The work up was done as described in Example 23, Step 2, to obtain crude product. The crude product was purified by preparative TLC (mobile phase: 70% ethyl acetate in hexane) to give racemic 1-(2-(1H-pyrazol-4-yl)thiazol-5-yl)-1-(pyridin-4-yl)propan-1-ol as pale yellow solid (134 mg, 35% yield) in 99% HPLC purity. 1H NMR (400 MHz, DMSO-d₆): δ 13.18 (br s, 1H), 8.50 (d, 2H), 8.22 (br s, 1H), 7.85 (br s, 1H), 7.63 (s, 1H), 7.43 (d, 2H), 6.28 (s, 1H), 2.32-2.24 (m, 2H), 0.75 (t, 3H); LC-MS m/z calculated for [M+H]⁺ 287.09. found 287.1.

Examples 19 and 20

Enantiomer #1 and Enantiomer #2 of 1-(2-(1H-Pyrazol-4-yl)thiazol-5-yl)-1-(pyridin-4-yl)propan-1-ol

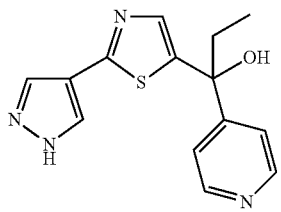 [SMILES: CCC(O)(c1ccncc1)c1cnc(-c2cn[nH]c2)s1]

Racemic 1-(2-(1H-pyrazol-4-yl)thiazol-5-yl)-1-(pyridin-4-yl)propan-1-ol (150 mg) was subjected to chiral HPLC purification using Chiralpak® IC [250 mm×4.6 mm×5μ column, mobile phase: n-heptane:ethanol with 0.1% DEA (50:50); flow rate: 1 mL/min] to afford 63 mg (84% recovery) of (−)-1-(2-(1H-pyrazol-4-yl)thiazol-5-yl)-1-(pyridin-4-yl)propan-1-ol (Enantiomer #1; $[\alpha]_D^{25}$−15.5 (c 1.0, MeOH)) and 63 mg (84% recovery) of (+)-1-(2-(1H-pyrazol-4-yl)thiazol-5-yl)-1-(pyridin-4-yl)propan-1-ol (Enantiomer #2; $[\alpha]_D^{25}$+15.7 (c 1.0, MeOH)), each enantiomer isolated with >99% ee. For each enantiomer: 1H NMR (400 MHz, DMSO-$d_6$): δ 13.17 (br s, 1H), 8.50 (d, 2H), 8.22 (br s, 1H), 7.85 (br s, 1H), 7.63 (s, 1H), 7.43 (d, 2H), 6.27 (s, 1H), 2.30-2.22 (m, 2H), 0.75 (t, 3H); LC-MS m/z calculated for [M+H]$^+$ 287.09. found 287.1.

Example 21

1-(5-(4-fluorophenyl)-1,3,4-thiadiazol-2-yl)-1-(pyridin-4-yl)propan-1-ol (Synthetic Method of Schemes 9, 2, and 1)

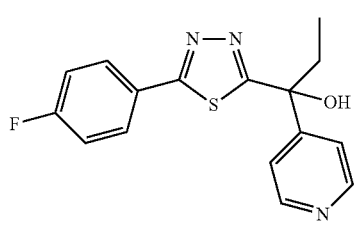 [SMILES: CCC(O)(c1ccncc1)c1nnc(-c2ccc(F)cc2)s1]

Step 1: (5-bromo-1,3,4-thiadiazol-2-yl)methanol

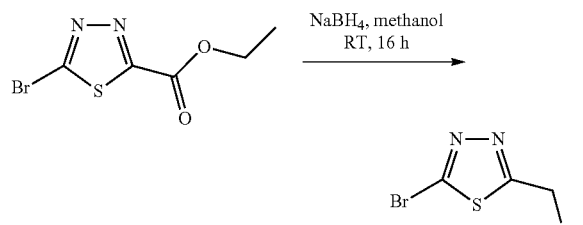

A solution of ethyl 5-bromo-1,3,4-thiadiazole-2-carboxylate (3.0 g, 12.65 mmol) [prepared as described in Jean-Philippe, International Patent Publication No. WO-2011/011872] in methanol (50 mL) was cooled to 0° C. and sodium borohydride (1.405 g, 37.97 mmol) slowly added and the reaction mixture was allowed to stir for 16 hours at room temperature. The reaction mixture was quenched with acetic acid (3 mL), extracted with ethyl acetate (200 mL), and the organic layer washed with sodium bicarbonate solution (20 mL) and then brine solution (10 mL). The organic layer was separated, dried over sodium sulfate and evaporated under reduced pressure to obtain crude product. The crude product was purified by Biotage IsoleraOne® column (using 25% ethyl acetate and hexane) to give (5-bromo-1,3,4-thiadiazol-2-yl)methanol as white solid (1.8 g, 73% Yield). 1H NMR (400 MHz, DMSO-$d_6$): δ 6.31 (t, 3H), 4.85 (d, 2H); LC-MS m/z calculated for [M+H]$^+$ 194.9. found 195.0.

Step 2: (5-(4-fluorophenyl)-1,3,4-thiadiazol-2-yl)methanol

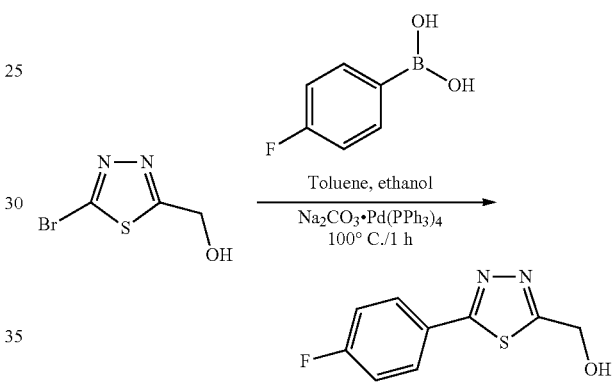

To a solution of (5-bromo-1,3,4-thiadiazol-2-yl)methanol (1.2 g, 6.153 mmol) in toluene (40 mL) and ethanol (40 mL) was added 4-fluorophenyl boronic acid (1.026 g, 7.384 mmol) and 2 M solution of aqueous Na$_2$CO$_3$. The reaction mixture was degassed with argon, Pd(PPh$_3$)$_4$ (0.354 g, 0.355 mmol) was added, the reaction mixture again degassed with argon for 10 min, and the mixture heated to 100° C. for 2 h. The reaction mixture was evaporated under vacuum to remove the ethanol, diluted with water (50 mL), extracted with ethyl acetate (200 mL), dried over sodium sulfate, filtered and evaporated under reduced pressure to obtain crude product. The crude product was purified by Biotage IsoleraOne® column (using 30% ethyl acetate and hexane) to give (5-(4-fluorophenyl)-1,3,4-thiadiazol-2-yl)methanol as pale yellow solid (0.85 g, 65% yield); LC-MS m/z calculated for [M+H]$^+$ 211.03. found 211.1.

Step 3: 5-(4-fluorophenyl)-1,3,4-thiadiazole-2-carbaldehyde

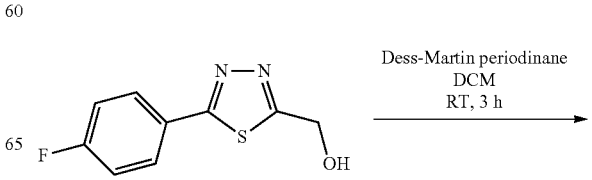

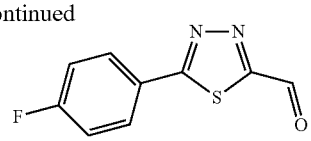

To a solution of 5-(4-fluorophenyl)-1,3,4-thiadiazole-2-yl) methanol (0.85 g, 4.0476 mmol) in dichloromethane (30 mL) at 0° C. was added DessMartin Periodinane (3.4 g, 8.095 mmol) slowly. The reaction mixture was allowed to warm to room temperature for 3 hours and saturated sodium bicarbonate solution (20 mL) and sodium thiosulfate (2 g) were added. The reaction mixture was extracted with ethyl acetate (200 mL), dried over sodium sulfate, filtered and evaporated under reduced pressure to obtain crude product. The crude compound was purified by flash column chromatography (using 20% ethyl acetate in hexane) to obtain 5-(4-fluorophenyl)-1,3,4-thiadiazole-2-carbaldehyde as white solid (0.45 g, 53% yield). 1H NMR (400 MHz, DMSO-$d_6$): δ 10.17 (s, 1H), 8.19 (q, 2H), 7.45 (t, 2H); LC-MS m/z calculated for [M+H]$^+$ 209.01. found 209.1.

Step 4: 1-(5-(4-fluorophenyl)-1,3,4-thiadiazol-2-yl) propan-1-ol

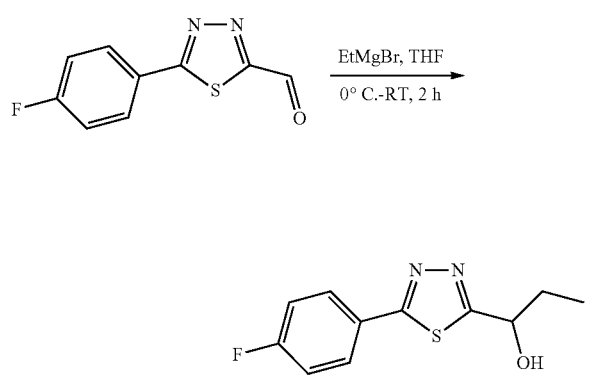

To a solution of 5-(4-fluorophenyl)-1,3,4-thiadiazole-2-carbaldehyde (0.2 g, 0.961 g mmol) in THF (8 mL) was added ethyl magnesium bromide in diethyl ether (3.0 M; 0.96 mL, 2.88 mmol) at 0° C., the reaction mixture was allowed to warm to room temperature and the mixture then stirred for 2 h. The reaction mixture was quenched with saturated ammonium chloride solution (15 mL) and water (15 mL), extracted with ethyl acetate (100 mL), dried over sodium sulfate and concentrated under reduced pressure to afford 1-(5-(4-fluorophenyl)-1,3,4-thiadiazol-2-yl)propan-1-ol as yellow solid (0.1 g, 45% yield). 1H NMR (400 MHz, DMSO-$d_6$): δ 8.0-8.03 (m, 1H), 7.39-7.35 (m, 2H), 6.36 (d, 1H), 4.92-4.89 (m, 1H), 1.89-1.78 (m, 2H), 0.95 (t, 3H); LC-MS m/z calculated for [M+H]$^+$ 239.06. found 239.1.

Step 5: 1-(5-(4-fluorophenyl-1,3,4-thiadizol-2-yl) propan-1-one

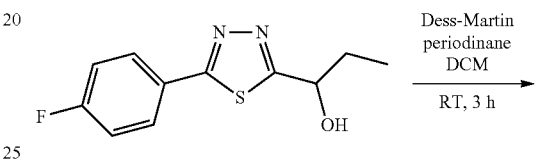

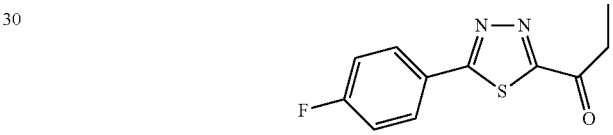

1-(5-(4-fluorophenyl)-1,3,4-thiadiazole-2-yl)propan-1-ol (0.210 g, 0.882 mmol) was oxidized using Dess-Martin Periodinane using the procedure described in step 3 to provide 1-(5-(4-fluorophenyl)-1,3,4-thiadizol-2-yl)propan-1-one as yellow solid (0.1 g, 50% yield). 1H NMR (400 MHz, DMSO-$d_6$): δ 8.04 (m, 2H), 7.25-7.19 (m, 2H), 3.30 (q, 2H), 1.31-1.29 (t, 3H); LC-MS m/z calculated for [M+H]$^+$ 237.04. found 237.1.

Step 6: 1-(5-(4-fluorophenyl)-1,3,4-thiadiazol-2-yl)-1-(pyridin-4-yl)propan-1-ol

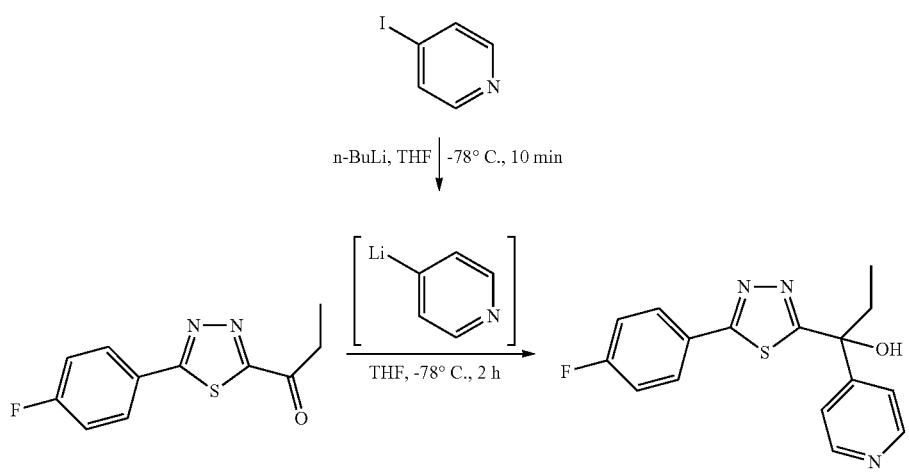

To a solution of 4-iodo pyridine (0.142 g, 0.635 mmol) in THF (12 mL) at −78° C. was added n-BuLi in hexane (1.6 M, 0.582 mL, 0.8474 mmol) and the mixture stirred for 30 min A solution of 1-(5-(4-fluorophenyl)-1,3,4-thiadiazol-2-yl)propan-1-one (0.1 g, 0.4237 mmol) in THF (8 mL) was added to above solution at −78° C. and the mixture stirred for 1 hour at −78° C. The reaction mixture was quenched with saturated ammonium chloride solution (20 mL) and diluted with water (25 mL). The reaction mixture was extracted with ethyl acetate (200 mL), dried over sodium sulfate and concentrated under reduced pressure to obtain crude product. The crude compound was purified by preparative TLC (using 5% methanol and dichloromethane) to afford 1-(5-(4-fluorophenyl)-1,3,4-thiadiazol-2-yl)-1-(pyridin-4-yl)propan-1-ol as white solid (22 mg, 17% yield). 1H NMR (400 MHz, DMSO-$d_6$): δ 8.55 (d, 2H), 8.0-7.96 (m, 2H), 7.56 (d, 2H), 7.35 (t, 2H), 7.06 (s, 1H), 2.40-2.30 (m, 2H), 0.80 (t, 3H); LC-MS m/z calculated for [M+H]$^+$ 316.08. found 316.1.

Example 22

1-(2-(6-Fluoropyridin-3-yl)thiazol-5-yl)-1-(pyridin-4-yl)ethanol (Synthetic Method of Scheme 6)

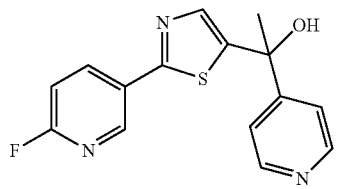 [SMILES: CC(O)(c1ccncc1)c1cnc(-c2ccc(F)nc2)s1]

Step 1: 2-(6-Fluoropyridin-3-yl)thiazole

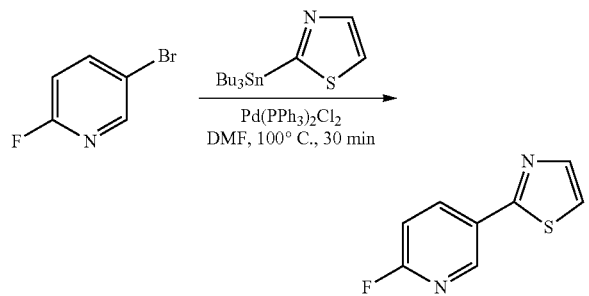

To a solution of 5-bromo-2-fluoropyridine (0.5 g, 2.857 mmol) in DMF (6 mL), 2-(tributylstannyl)thiazole (1.3 mL, 4.285 mmol) and Pd(PPh$_3$)$_2$Cl$_2$ (0.2 mg, 0.2857 mmol) were added under argon. The mixture was degassed with argon for 10 min and heated to 100° C. for 30 min. The reaction mixture was filtered through Celite® reagent and the filtrate was diluted with EtOAc (2×100 mL) and water (100 mL). The organic layer was separated, dried over Na$_2$SO$_4$, filtered and concentrated under reduced pressure to obtain crude product. The crude product was purified by Biotage IsoleraOne® column (5% ethyl acetate in hexane) to obtain 2-(6-fluoropyridin-3-yl)thiazole as off-white solid (0.4 g, 80% yield). 1H NMR (400 MHz, DMSO-$d_6$): δ 8.80 (s, 1H), 8.52-8.47 (m, 1H), 7.98 (d, 1H), 7.87 (d, 1H), 7.33 (dd, 1H); LC-MS m/z calculated for [M+H]$^+$ 181.02. found 180.8.

Step 2: 1-(2-(6-Fluoropyridin-3-yl)thiazol-5-yl)-1-(pyridin-4-yl)ethanol

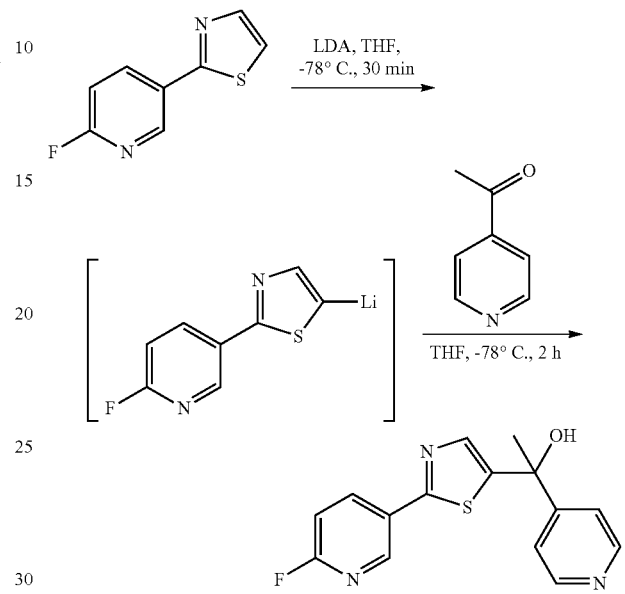

To a solution of diisopropylamine (0.12 mL, 0.833 mmol) in dry THF (5 mL) was added n-BuLi in hexanes (1.6M, 0.7 mL, 1.111 mmol) slowly at −78° C. The mixture was stirred for 30 min, 2-(6-fluoropyridin-3-yl)thiazole (0.1 g, 0.555 mmol) in THF (5.0 mL) at −78° C. added, and the mixture stirred for 30 min A solution of 1-(pyridin-4-yl)ethanone (0.09 mL, 0.833 mmol) in THF (5.0 mL) was added to reaction mixture, stirred for 2 hours at −78° C. The reaction mixture was quenched with saturated NH$_4$Cl (50 mL) solution and extracted with EtOAc (3×50 mL). The organic layer was washed with water (2×50 mL), dried over Na$_2$SO$_4$, filtered and concentrated under reduced pressure to obtain crude product. The crude product was purified by preparative TLC (3% methanol in dichloromethane) to obtain 1-(2-(6-fluoropyridin-3-yl)thiazol-5-yl)-1-(pyridin-4-yl)ethanol as off-white solid (0.035 g, 22% yield) in 99.7% HPLC purity. 1H NMR (400 MHz, DMSO-$d_6$): δ 8.31 (s, 1H), 8.21 (d, 2H), 7.79 (d, 1H), 7.71 (d, 1H), 7.67 (s, 1H), 7.11 (s, 1H), 6.91 (d 2H), 1.83 (s, 3H); LC-MS m/z calculated for [M+H]$^+$ 302.07. found 302.1.

Example 23

1-(2-(4-Fluorophenyl)oxazol-5-yl)-1-(pyridin-4-yl)ethanol (synthetic method of Scheme 7)

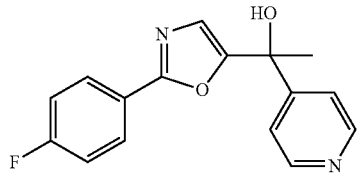 [SMILES: CC(O)(c1ccncc1)c1cnc(-c2ccc(F)cc2)o1]

Step 1: 2-(4-Fluorophenyl)oxazole

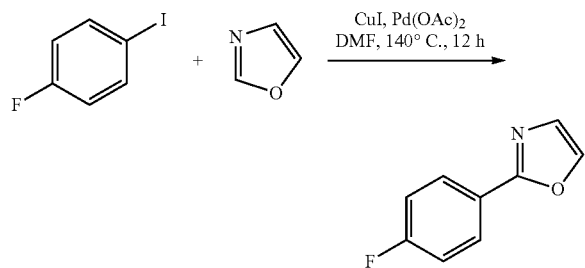

A solution of 1-fluoro-4-iodobenzene (1 g, 0.0144 mmol) in DMF (15 mL) was purged with argon, and oxazole (6.4 g/3.3 mL, 0.02898 mmol), copper iodide (5.5 g, 0.02898 mmol) and palladium (II) acetate (0.15 g, 0.000724 mmol) was added. The reaction mixture was purged with argon for 5 min and refluxed under argon for 12 h. The solution was cooled to room temperature and diluted with ice cold water (100 mL). The reaction mixture was extracted with ethyl acetate (200 mL) and filtered through Celite® reagent. The organic solvent was dried with sodium sulfate, filtered and the solvent was removed under reduced pressure to obtain crude product. The crude product was purified by Biotage Isolera-One® column using a 25 g column (7% ethyl acetate in hexane) to give 2-(4-fluorophenyl)oxazole (0.6 g, 26%) as yellow liquid. 1H NMR (400 MHz, DMSO-$d_6$): δ 8.19 (s, 1H), 8.03-7.99 (m, 2H), 7.34 (t, 3H); LC-MS m/z calculated for [M+H]$^+$ 164.05. found 164.1.

Step 2: 1-(2-(4-Fluorophenyl)oxazol-5-yl)-1-(pyridin-4-yl)ethanol

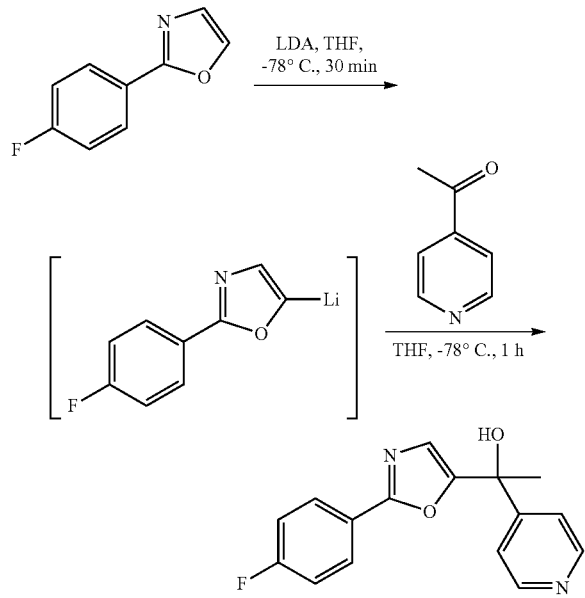

To a stirred solution of DIPA (0.13 mL, 0.00092 mmol) in THF (7 mL) at −78° C. was added n-BuLi (0.76 mL, 0.001226 mmol). The mixture was allowed to stir at 0° C. for 30 min, was again cooled to −78° C., and then a solution of 2-(4-fluorophenyl)oxazole (0.1 g, 0.000613 mmol) in THF (2 mL) was added dropwise during 30 min. 4-Acetyl pyridine (0.07 mL, 0.000674 mmol) in THF (2 mL) was then added, the reaction mixture was stirred for an additional 1 hour at −78° C., quenched with saturated ammonium chloride (2 mL), diluted with water (10 mL), and extracted with ethyl acetate (20 mL). The organic layer was dried with sodium sulfate, filtered and the solvent was concentrated under reduced pressure to obtain crude product. The crude product was purified by silica gel chromatography (200-400 mesh, 2% of methanol in dichloromethane) to give 1-(2-(4-fluorophenyl)oxazol-5-yl)-1-(pyridin-4-yl)ethanol (0.14 g, 82%) as white solid in 98.5% HPLC purity. 1H NMR (400 MHz, DMSO-$d_6$): δ 8.53 (d, 2H), 7.95-7.91 (m, 2H), 7.45 (d, 2H), 7.32 (t, 2H), 7.14 (d, 1H), 6.38 (s, 1H), 1.81 (s, 3H); LC-MS m/z calculated for [M+H]$^+$ 285.10. found 285.1.

Example 24

1-(2-(4-Fluorophenyl)thiazol-5-yl)-2-methyl-1-(pyridin-4-yl)propan-1-ol (Synthetic Method of Scheme 3)

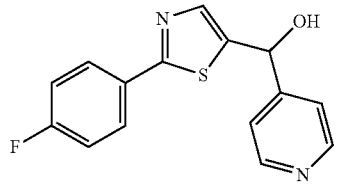 [SMILES: OC(c1ccncc1)c1cnc(-c2ccc(F)cc2)s1]

Step 1: 2-(4-Fluorophenyl)thiazole

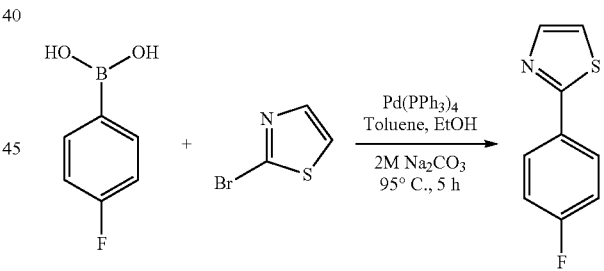

To a stirred solution of (4-fluorophenyl)boronic acid (10 g, 60.9 mmol) in toluene (70 mL) and ethanol (200 mL) was added 2-bromothiazole (12.7 g, 91.4 mmol) and Na$_2$CO$_3$ (2M, 100 mL, 19.39 g). The reaction mixture was purged with argon for 45 min, Pd(PPh$_3$)$_4$ (3.5 g, 3.04 mmol) added, and the mixture stirred at 95° C. for 5 h. The reaction mixture was cooled to room temperature, quenched with saturated sodium bicarbonate solution (2×100 mL), and extracted with ethyl acetate (2×100 mL). The combined organic layers were washed with ice-cold water (2×100 mL), followed by brine solution (50 mL). The organic layer was dried over sodium sulfate, filtered and concentrated under reduced pressure to obtain crude product. The crude product was purified by column chromatography (100-200 mesh silica gel; using 10% ethyl acetate in hexane) to obtain 2-(4-fluorophenyl)thiazole as white solid (9.0 g, 82% yield). 1H NMR (400 MHz, DMSO-d$_6$): δ 7.98 (dd, 2H), 7.88 (d, 1H); 7.91 (d, 1H), 7.88 (d, 1H), 7.31 (t, 2H); LC-MS m/z calculated for [M+H]$^+$ 180.02 found 179.91.

Step 2: (2-(4-Fluorophenyl)thiazol-5-yl)(pyridin-4-yl)methanol

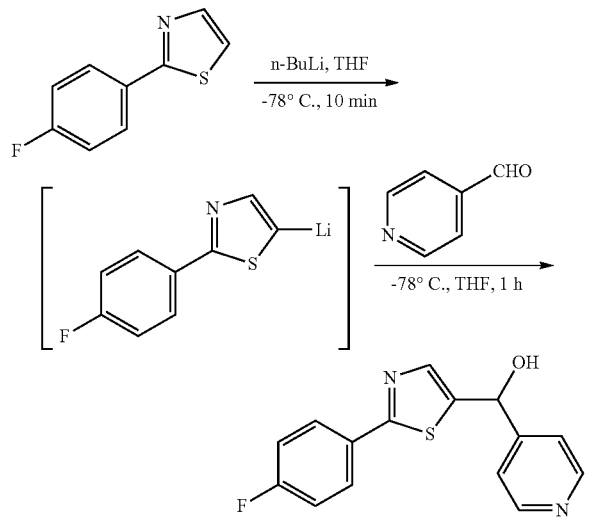

To a solution of diisopropylamine (0.55 mL, 3.9 mmol) in dry THF (10 mL) at −78° C. was added n-BuLi (2.4 mL, 3.9 mmol) dropwise, and then the mixture was stirred for 30 min to produce LDA. A solution of 2-(4-fluorophenyl)thiazole (0.5 g, 2.79 mmol) in dry THF (10 mL) at −78° C. was added dropwise to the above LDA solution, and the mixture was stirred for 30 min. To this reaction mixture was added isonicotinaldehyde (0.298 g, 2.79 mmol) dropwise and the mixture was stirred for 1 hour at −78° C. The reaction was quenched with ammonium chloride solution (10 mL), extracted with ethyl acetate (2×20 mL), washed with brine solution (20 mL), dried over sodium sulfate, concentrated under reduced pressure and purified by silica gel column chromatography (100-200 mesh silica gel; using 10% MeOH in DCM to obtain 2-(4-fluorophenyl)thiazol-5-yl)(pyridin-4-yl)methanol (0.6 g, 75% yield). $^1$H NMR (400 MHz, DMSO-d$_6$): δ 8.56 (d, 2H), 7.91 (dd, 2H), 7.79 (s, 1H), 7.44 (d, 2H), 7.28 (ds, 2H), 6.71 (d, 1H), 6.12 (d, 1H); LC-MS m/z calculated for [M+H]$^+$ 287.06 found 287.02.

Example 25

5-(2-(4-fluorophenyl)thiazol-5-yl)-5,6,7,8-tetrahydroisoquinolin-5-ol (Synthetic Method of Scheme 3)

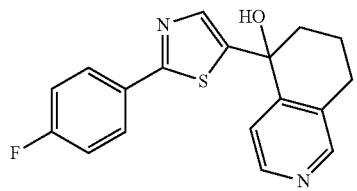 [SMILES: OC1(c2cnc(-c3ccc(F)cc3)s2)CCCc2cnccc21]

Step 1: 2-(4-fluorophenyl)thiazole

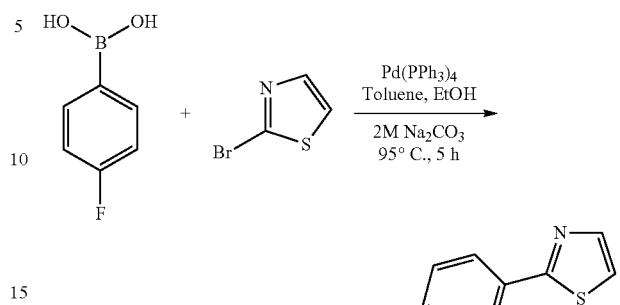

To a stirred solution of (4-fluorophenyl)boronic acid (10 g, 60.9 mmol) in toluene (70 mL) and ethanol (200 mL) was added 2-bromothiazole (12.7 g, 91.4 mmol), followed by Pd(PPh$_3$)$_4$ (3.5 g, 3.04 mmol). The reaction mixture was purged with argon for 20 min, Na$_2$CO$_3$ solution (2M, 100 mL, 19.39 g) added, and the reaction mixture stirred at 95° C. for 5 h. The reaction mixture was cooled to room temperature, quenched with saturated sodium bicarbonate solution (2×100 mL), and extracted with ethyl acetate (2×100 mL). The combined organic layer was washed with ice-cold water (2×100 mL) followed by brine solution, dried over sodium sulfate, filtered and concentrated under reduced pressure to obtained crude product. The crude product was purified by column chromatography (100-200 mesh silica gel) using 10% ethyl acetate in hexane to obtain 2-(4-fluorophenyl)thiazole as white solid (9.0 g, 82% yield). 1H NMR (400 MHz, DMSO): 7.98 (dd, 2H, J=6.8 & 14.0 Hz), 7.88 (d, 1H, J=4.8 Hz), 7.91 (d, 1H, J=2.8 Hz), 7.88 (d, 1H, J=4.8 Hz), 7.31 (t, 2H, J=8.8 & 17.2 Hz).

Step 2: 5-(2-(4-fluorophenyl)thiazol-5-yl)-5,6,7,8-tetrahydroisoquinolin-5-ol

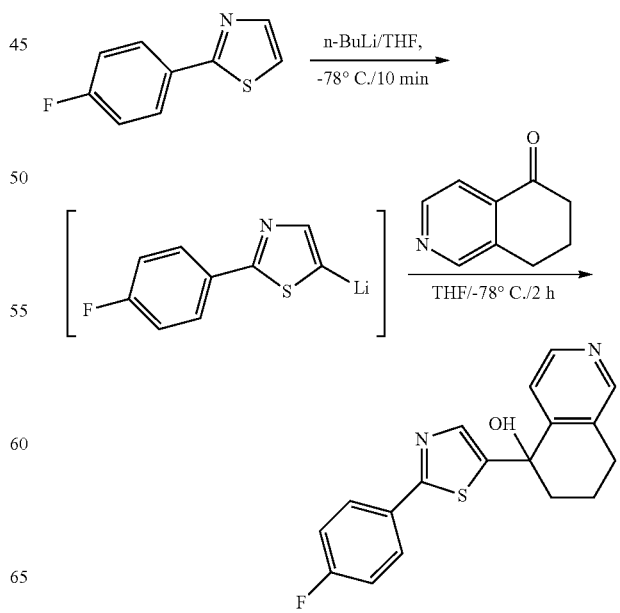

To a solution of DIPA (0.424 g, 4.2 mmol) in dry THF at −78° C. was added n-BuLi (0.268 g, 4.2 mmol) dropwise at −78° C., and the mixture was stirred for 30 min to produce LDA. A solution of 2-(4-fluorophenyl)thiazole (0.510 g, 2.8 mmol) in dry THF at −78° C. was then added to the above LDA solution. 7,8-Dihydroisoquinolin-5(6H)-one (0.419 g, 2.8 mmol) [prepared as described in Vanotti, International Patent Publication No. WO-2008/065054] was added dropwise to the reaction mixture, which was then stirred for 20 min at −78° C. After completion of the reaction, the reaction was quenched with saturated ammonium chloride, extracted with ethyl acetate (3×30 mL), washed with water followed by brine, dried over sodium sulfate, and concentrated under reduced pressure. The crude solid was purified by washing with the mixture of MeOH and ether, followed by filtering resulted in 5-(2-(4-fluorophenyl)thiazol-5-yl)-5,6,7,8-tetrahydroisoquinolin-5-ol (0.42 g, 45% yield). $^1$H NMR (400 MHz, DMSO-$d_6$): δ 1.67 (m, 1H), 1.97 (m, 1H), 2.16 (t, 2H), 2.80 (t, 2H), 6.50 (s, 1H), 7.26 (s, 1H), 7.29 (m, 3H), 7.92 (m, 2H), 8.36 (m, 1H), 8.41 (s, 1H); LC-MS m/z calculated for [M+H]$^+$ 327.09. found 327.1.

Example 26

1-(Pyridin-4-yl)-1-(2-(4-(trifluoromethyl)phenyl) thiazol-5-yl)ethanol (Synthetic Method of Scheme 3)

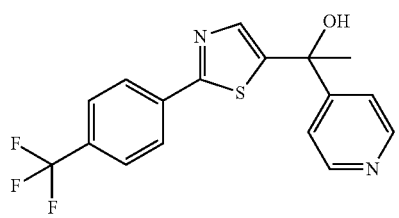 [SMILES: CC(O)(c1ccncc1)c1cnc(-c2ccc(C(F)(F)F)cc2)s1]

Step 1: 2-(4-(Trifluoromethyl)phenyl)thiazole

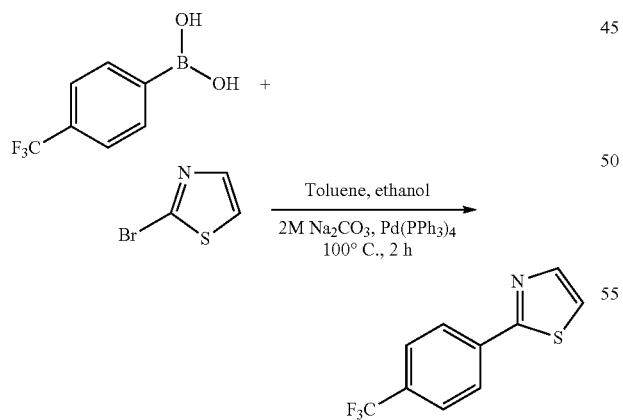

Using (4-(trifluoromethyl)phenyl)boronic acid (0.5 g, 3.06 mmol) and 2-bromo thiazole (1.1 g, 61.3 mmol) and following the procedure described in Example 7, Step 1, the title compound was obtained after purification by flash chromatography (60-120 mesh, 2% ethyl acetate in hexane) as white solid (0.5 g, 83% Yield). 1H NMR (400 MHz, DMSO-$d_6$): δ 8.15 (d, 2H), 8.00 (d, 1H), 7.90 (d, 1H), 7.85 (d, 2H); LC-MS m/z calculated for [M+H]$^+$ 230.02. found 230.1.

Step 2: 1-(Pyridin-4-yl)-1-(2-(4-(trifluoromethyl) phenyl)thiazol-5-yl)ethanol

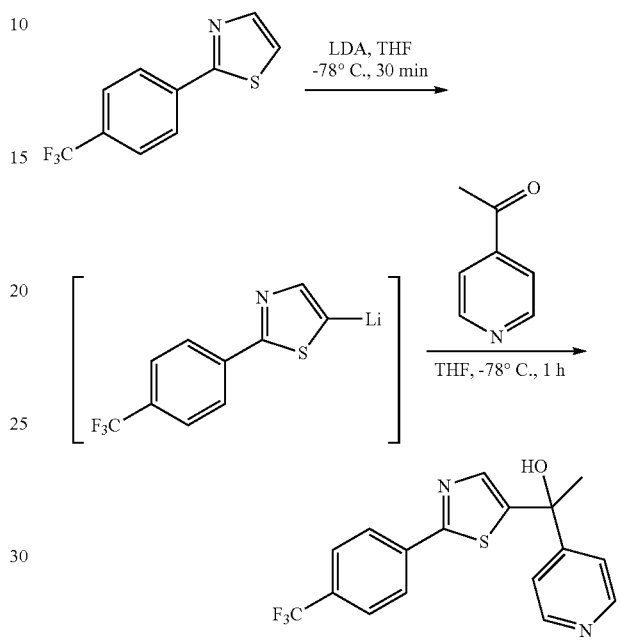

To a stirred solution of DIPA (0.09 mL, 0.000655 mmol) in THF (7 mL) at −78° C. was added n-BuLi (0.54 mL, 0.000873 mmol) and the mixture stirred at 0° C. for 30 min. After the reaction mixture was cooled to −78° C., a solution of 2-(4-(trifluoromethyl)phenyl)thiazole (0.1 g, 0.000436 mmol) in THF (2 mL) was added dropwise over 30 min 1-(Pyridin-4-yl)ethanone (0.05 mL, 0.000480 mmol) in THF (2 mL) was then added and the reaction mixture was stirred for an additional 1 hour at −78° C. The work up and purification was done as described in Example 23, Step 2, to provide 1-(pyridin-4-yl)-1-(2-(4-(trifluoromethyl)phenyl)thiazol-5-yl)ethanol (0.12 g, 80%) as off-white solid in 99% HPLC purity. 1H NMR (400 MHz, DMSO-$d_6$): δ 8.52 (dd, 2H), 8.07 (d, 2H), 7.90 (s, 1H), 7.80 (d, 2H), 7.50 (dd, 2H), 6.71 (s, 1H), 1.94 (s, 3H); LC-MS m/z calculated for [M+H]$^+$ 351.07. found 351.1.

Example 28

1-(2-(4-Chlorophenyl)thiazol-5-yl)-1-(pyridin-4-yl) ethanol (Synthetic Method of Scheme 3)

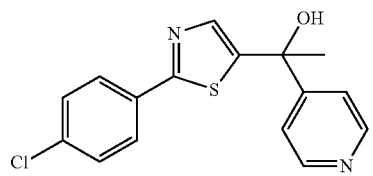

Step 1: 2-(4-Chlorophenyl)thiazole

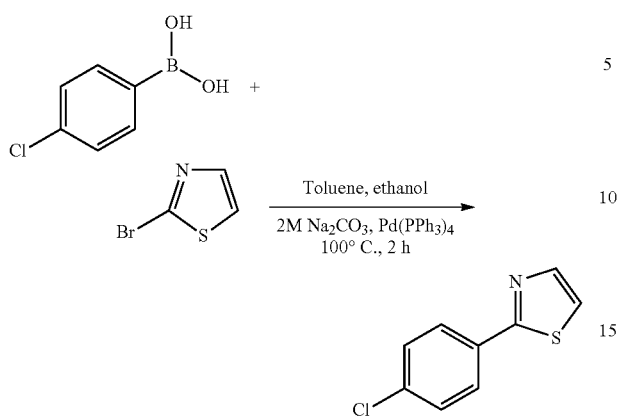

Using 2-bromothiazole (0.5 g, 3.05 mmol) and (4-chlorophenyl)boronic acid (0.57 g, 3.65 mmol) and following the procedure described in Example 7, Step 1, the title compound was obtained after purification by column chromatography (15% ethyl acetate in hexane) as colorless viscous liquid (0.5 g, 80% yield). 1H NMR (400 MHz, DMSO-$d_6$): δ 7.95 (d, 2H), 7.92 (d, 1H), 7.80 (d, 1H), 7.55 (d, 2H); LC-MS m/z calculated for [M+H]$^+$ 195.99. found 195.9.

Step 2: 1-(2-(4-Chlorophenyl)thiazol-5-yl)-1-(pyridin-4-yl)ethanol

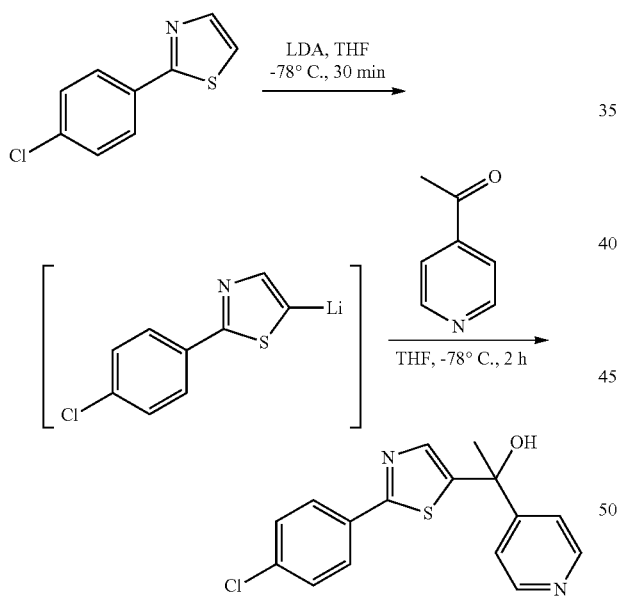

To a solution of diisopropylamine (0.2 mL, 1.538 mmol) in dry THF (5 mL), was added 1.6M n-BuLi in hexanes (0.96 mL, 1.538 mmol) slowly at −78° C. The reaction mixture was stirred for 30 min, 2-(4-chlorophenyl)thiazole (0.2 g, 1.025 mmol) in THF (10.0 mL) added, the mixture stirred for 30 min, a solution of 1-(pyridin-4-yl)ethanone (0.17 mL, 1.538 mmol) in THF (5.0 mL) added, and the mixture was stirred for 2 hours at −78° C. The reaction mixture was quenched with saturated NH$_4$Cl (50 mL) solution and extracted with EtOAc (2×100 mL). The organic layer was washed with water (2×50 mL), dried over Na$_2$SO$_4$, filtered and concentrated under reduced pressure to obtain crude product. The crude product was purified by column chromatography (1% methanol in dichloromethane) to obtain 1-(2-(4-chlorophenyl)thiazol-5-yl)-1-(pyridin-4-yl)ethanol as off-white solid (0.1 g, 31% yield) in 99.9% HPLC purity. 1H NMR (400 MHz, DMSO-$d_6$): δ 8.51 (d, 2H), 7.87 (d, 2H), 7.82 (s, 1H), 7.51-7.47 (m, 4H), 6.66 (s, 1H), 1.92 (s, 3H); LC-MS m/z calculated for [M+H]$^+$ 317.04. found 317.4.

Example 29

1-(5-(4-Fluorophenyl)-1,2,4-oxadiazol-3-yl)-1-(pyridin-4-yl)ethanol (Synthetic Method of Schemes 10A and 1)

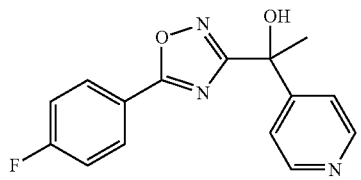 [SMILES: CC(O)(c1ccncc1)c1noc(-c2ccc(F)cc2)n1]

Step 1: N,2-dihydroxyacetimidamide

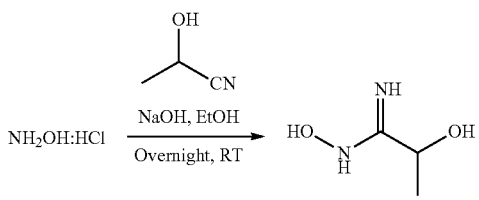

To a solution of hydroxylamine hydrochloride (5 g, 72.4 mmol) in ethanol (70 mL) was added NaOH (3 g, 76.0 mmol) and the reaction stirred overnight at room temperature. The reaction was filtered, 2-hydroxypropionitrile was added to the filtrate and the reaction stirred for 3 hours at room temperature. After completion, the reaction was concentrated under reduced pressure to obtain N,2-dihydroxyacetimidamide as white solid (2.7 g, 36% yield). LC-MS m/z calculated for [M+H]$^+$ 105.06. found 105.0.

Step 2: 1-(5-(4-Fluorophenyl)-1,2,4-oxadiazol-3-yl) ethanol

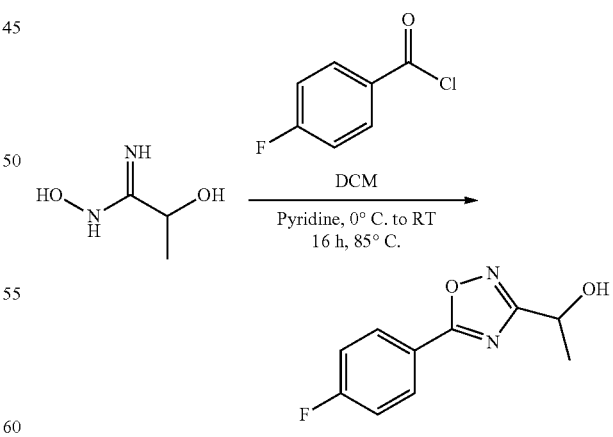

To a solution of N,2-dihydroxyacetimidamide (2.7 g, 26.4 mmol) in pyridine (20 mL) was added dropwise 4-fluorobenzoyl chloride (3 g, 18.9 mmol) in DCM (30 mL) at 0° C. to 10° C. The reaction was stirred for 6 hours at room temperature and the solid was filtered and washed with DCM (50 mL). The solid was dissolved in ethanol and the solution refluxed for 16 hours at 85° C. The mixture was evaporated under reduced pressure. The crude product was purified by silica gel column chromatography (100-200 mesh; using 10% ethyl acetate in hexane) to obtain 1-(5-(4-fluorophenyl)-1,2,4-oxadiazol-3-yl)ethanol as white solid (0.35 g, 9% yield). 1H NMR (400 MHz, CDCl$_3$): δ 8.14 (dd, 1H), 7.20 (dd, 1H), 5.06 (q, 1H), 1.66 (d, 3H).

Step 3: 1-(5-(4-Fluorophenyl)-1,2,4-oxadiazol-3-yl)ethanone

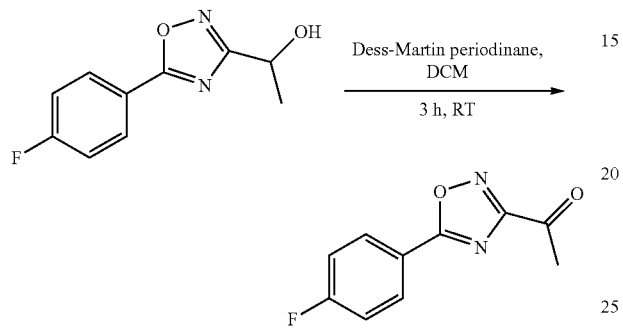

To a stirred solution of 1-(5-(4-fluorophenyl)-1,2,4-oxadiazol-3-yl)ethanol (0.34 g, 1.92 mmol) in DCM (40 mL) was added Dess-Martin periodinane (2.7 g, 6.5 mmol) at room temperature and the mixture stirred for 3 h. The reaction mixture was filtered and washed with DCM (15 mL). To the filtrate was added NaHCO$_3$ solution (10 mL) and DCM (30 mL). The organic layer was separated, washed with water (20 mL) followed by brine solution (20 mL), dried over anhydrous sodium sulfate and concentrated under reduced pressure to get crude compound. The crude compound was purified by silica gel column chromatography (100-200 mesh; using 10% methanol in DCM) to obtain 1-(5-(4-fluorophenyl)-1,2,4-oxadiazol-3-yl)ethanone as off-white solid (0.25 g, 72% yield). 1H NMR (400 MHz, CDCl$_3$): δ 2.76 (s, 3H), 7.23 (t, 2H), 7.23 (dd, 2H), LC-MS m/z calculated for [M+H]$^+$ 207.17. found 206.87.

Step 4: 1-(5-(4-Fluorophenyl)-1,2,4-oxadiazol-3-yl)-1-(pyridin-4-yl)ethanol

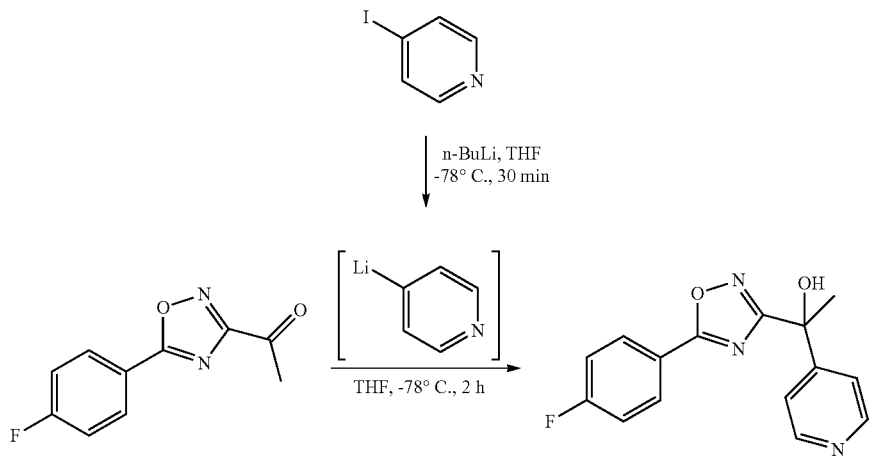

To a stirred solution of 4-iodopyridine (0.29 g, 0.463 mmol) in THF (30 mL) at −78° C. was added n-BuLi (2.4 mL, 3.9 mmol) and the mixture was stirred for 10 min. 1-(5-(4-Fluorophenyl)-1,2,4-oxadiazol-3-yl)ethanone (0.5 g, 2.79 mmol) in THF (5 mL) was then added to reaction, which was then stirred at −78° C. for 2 h. The reaction was then quenched with saturated ammonium chloride solution (10 mL) and diluted with ethyl acetate (50 mL). The organic layer was separated, washed with ammonium chloride solution (3×150 mL) followed by brine solution (2×20 mL), dried over sodium sulfate, filtered and concentrated under reduced pressure to obtain crude product. The crude product was purified by column chromatography (100-200μ silica gel and 30% ethyl acetate in hexane) to obtain 3-(4-fluorophenyl)-5-(1-(pyridin-4-yl)ethyl)isoxazole as off-white solid (0.06 g, 29% yield). 1H NMR (400 MHz, CDCl$_3$): δ 8.60 (d, 2H), 8.11 (dd, 2H), 7.48 (d, 2H), 7.19 (t, 2H), 3.40 (s, 1H), 1.99 (s, 3H); LC-MS m/z calculated for [M+H]$^+$ 286.09. found 286.2.

Example 30

4-(5-(1-Hydroxy-1-(pyridin-4-yl)ethyl)thiazol-2-yl)-2-(trifluoro-methyl)benzonitrile (Synthetic Method of Scheme 8)

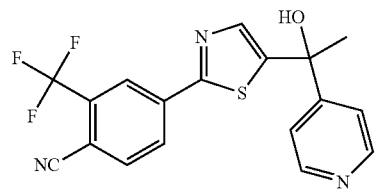 [SMILES: CC(O)(c1ccncc1)c1cnc(-c2ccc(C#N)c(C(F)(F)F)c2)s1]

Step 1:
4-(Thiazol-2-yl)-2-(trifluoromethyl)benzonitrile

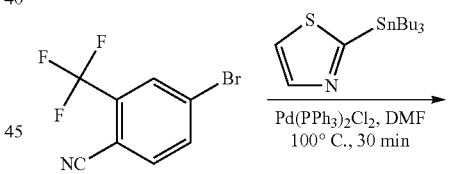

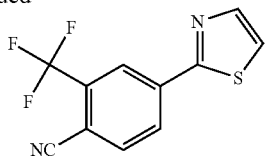

A solution of 4-bromo-2-(trifluoromethyl)benzonitrile (0.5 g, 2 mmol) in DMF (5 mL) was purged with argon and 2-(tributylstannyl)thiazole (1.12 g/0.9 mL, 3 mmol) and 1,1'-bis(diphenylphosphino)ferrocene-palladium(II)dichloride (0.14 g, 0.2 mmol) added. The reaction mixture was purged with argon for 5 min and retained in microwave for 30 min at 100° C. The reaction mixture was diluted with ice cold water (10 mL) and extracted with ethyl acetate (200 mL). The organic solvent was dried over sodium sulfate, filtered and the solvent was evaporated under reduced pressure to obtain crude product. The crude product was purified by silica gel chromatography (100-200 mesh; 8% ethyl acetate in hexane) to give 4-(thiazol-2-yl)-2-(trifluoromethyl)benzonitrile (0.42 g, 84% yield) as pale yellow solid. 1H NMR (400 MHz, DMSO-$d_6$): δ 8.42-8.39 (m, 2H), 8.27 (d, 1H), 8.08 (d, 1H), 8.03 (d, 1H). LC-MS m/z calculated for [M+H]$^+$ 255.01. found 255.0.

Step 2: 4-(5-(1-Hydroxy-1-(pyridin-4-yl)ethyl)thiazol-2-yl)-2-(trifluoromethyl)-benzonitrile

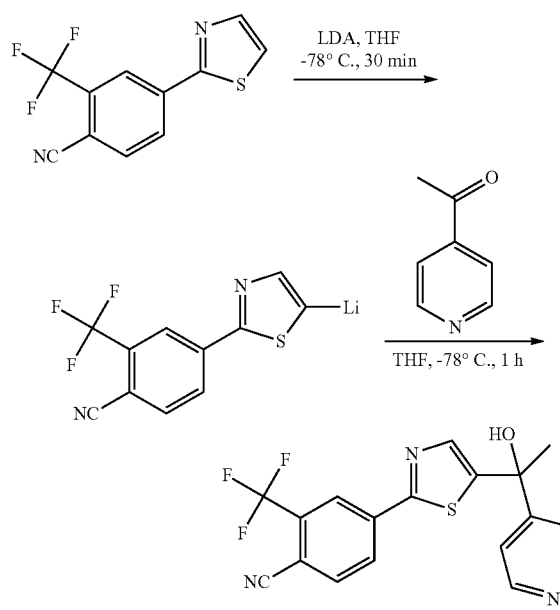

A solution of diisopropylamine (0.08 mL, 0.59 mmol) in THF (7 mL) was cooled to −78° C., and 1.6M n-BuLi in hexanes (0.49 mL, 0.78 mmol) added. The reaction mixture was allowed to stir at 0° C. for 30 min, again cooled to −78° C. and a solution of 4-(thiazol-2-yl)-2-(trifluoromethyl)benzonitrile (0.1 g, 0.39 mmol) in THF (2 mL) added dropwise at −78° C. for 30 min. 4-Acetyl pyridine (0.048 mL, 0.43 mmol) in THF (2 mL) at −78° C. was then slowly added, the reaction was stirred for 1 hour and quenched with saturated ammonium chloride (2 mL), and water (10 mL). The reaction mixture was extracted with ethyl acetate (20 mL), the organic layer was dried over sodium sulfate, filtered and the solvent was evaporated under reduced pressure to obtain crude product. The crude product was product purified by Prep TLC (5% methanol in dichloromethane) to give 4-(5-(1-hydroxy-1-(pyridin-4-yl)ethyl)thiazol-2-yl)-2-(trifluoromethyl)benzonitrile (30 mg, 21%) as pale yellow solid in 99.1% HPLC purity. 1H NMR (400 MHz, DMSO-$d_6$): δ 8.54 (d, 2H), 8.36-8.32 (m, 2H), 8.24 (d, 1H), 8.03 (s, 1H), 7.52-7.51 (m, 2H), 6.81 (s, 1H), 1.97 (s, 3H). LC-MS m/z calculated for [M+H]$^+$ 376.07. found 375.7.

Example 31

1-(5-(4-Fluorophenyl)-1,3,4-oxadiazol-2-yl)-1-(pyridin-4-yl)ethanol (Synthetic Method of Schemes 11 and 3)

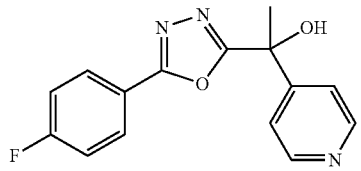 [SMILES: CC(O)(c1ccncc1)c1nnc(-c2ccc(F)cc2)o1]

Step 1: 4-fluorobenzohydrazide

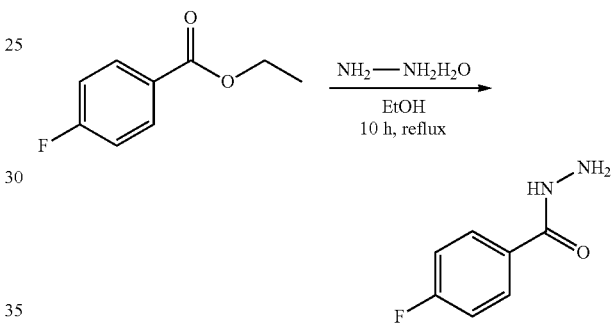

To a stirred solution of 4-fluoroethylbenzoate (4.5 g, 26.7 mmol) in EtOH (30 mL) was added NH$_2$NH$_2$.H$_2$O (6.67 g, 133.5 mmol) at room temperature and the solution refluxed at 85° C. for 10 h. The reaction was cooled to room temperature, concentrated under reduced pressure, and the solid washed with n-hexane (50 mL) and then dried to obtain 4-fluorobenzohydrazide as a solid (4.2 g, quantitative yield). 1H NMR (400 MHz, DMSO-$d_6$): δ 9.85 (s, 1H), 7.86 (dd, 2H), 7.25 (t, 3H), 4.46 (s, 1H), 3.47 (br s, 1H).

Step 2: 2-(4-Fluorophenyl)-1,3,4-oxadiazole

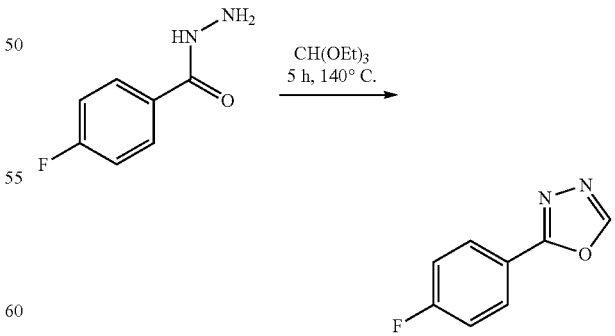

A stirred solution of 4-fluorobenzohydrazide (4.2 g, 27.2 mmol) in triethylorthoformate (27 mL) was heated at 140° C. for 5 h. The reaction was evaporated under reduced pressure. The crude was purified by silica gel column chromatography (100-200 mesh; using 12% ethyl acetate in hexane) to afford 2-(4-fluorophenyl)-1,3,4-oxadiazole [Polshettiwar, Tetrahedron Letters, 49:879-883 (2008)] as off-white solid (2.5 g, 57% yield). 1H NMR (400 MHz, DMSO-$d_6$): δ 8.46 (s, 1H), 8.08 (dd, 2H), 7.19 (dd, 2H); LC-MS m/z calculated for [M+H]$^+$ 165.04. found 165.00.

Step 3: 1-(5-(4-Fluorophenyl)-1,3,4-oxadiazol-2-yl)-1-(pyridin-4-yl)ethanol

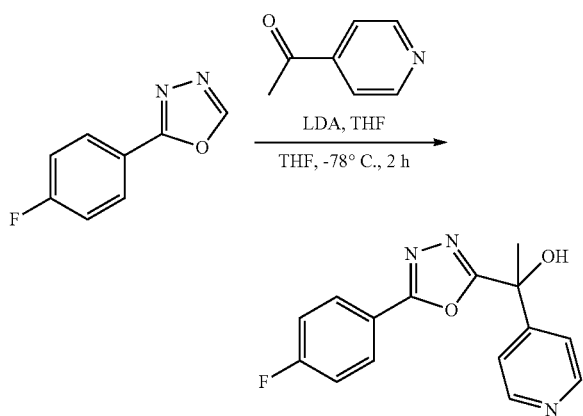

To a stirred solution of 2-(4-fluorophenyl)-1,3,4-oxadiazole (0.8 g, 2.4 mmol) in THF (10 mL) was added LDA (2.9 mmol) at −78° C. (0.308 g, 2.9 mmol) and mixture was stirred for 20 min A solution of 4-acetyl pyridine (0.377 g, 3.1 mmol) in THF (10 mL) was added at −78° C. and stirred for 2 h. The reaction mixture was quenched with saturated NH$_4$Cl solution (50 mL), extracted with ethyl acetate (3×60 mL), washed with brine solution (60 mL), dried over anhydrous Na$_2$SO$_4$ and concentrated under reduced pressure. The crude product was purified by silica gel column chromatography (100-200 mesh; using 90% ethyl acetate in hexanes) to obtain 1-(5-(4-fluorophenyl)-1,3,4-oxadiazol-2-yl)-1-(pyridin-4-yl)ethanol as off-white solid (combined yield for 2 batches: 0.051 g, 4% yield). 1H NMR (400 MHz, DMSO-$d_6$): δ 8.58 (s, 2H), 7.99 (t, 2H), 7.48 (d, 2H), 7.04 (d, 2H), 6.98 (s, 1H), 1.94 (s, 3H); LC-MS m/z calculated for [M+H]$^+$ 286.09. found 286.08.

Example 32

3-(4-Fluorophenyl)-5-(1-(pyridin-4-yl)ethyl)isoxazole (Synthetic Method of Schemes 12 and 1)

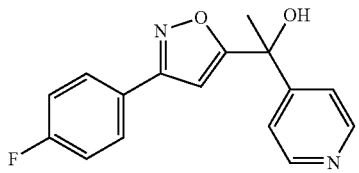 [SMILES: CC(O)(c1ccncc1)c1cc(-c2ccc(F)cc2)no1]

Step 1: 4-Fluorobenzaldehyde oxime

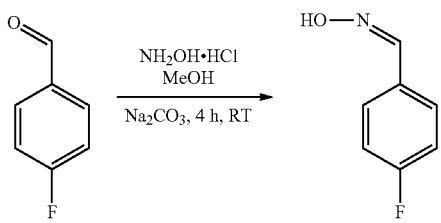 [SMILES: O=Cc1ccc(F)cc1 ; O/N=C\c1ccc(F)cc1]

To a solution of 4-fluorobenzaldehyde (3.0 g, 24.1 mmol) in MeOH (15 mL) was added NH$_2$OH.HCl (2.0 g, 29.1 mmol) and Na$_2$CO$_3$ (1.53 g, 14.4 mmol) and the reaction stirred for 4 hours at room temperature. The reaction was concentrated under reduced pressure, extracted with DCM (2×100 mL), and the organic layer washed with water (2×50 mL) followed by brine solution (2×25 mL). The organic layer was concentrated under reduced pressure to obtain 4-fluorobenzaldehyde oxime [Brain, J. Am. Chem. Soc., 133:949-957 (2011)] as white solid (2 g, 61% yield). 1H NMR (400 MHz, CDCl$_3$): δ 8.12 (s, 1H), 7.55 (dd, 2H), 7.06 (t, 2H).

Step 2: 1-(3-(4-FluorophenyBisoxazol-5-yl)ethanol

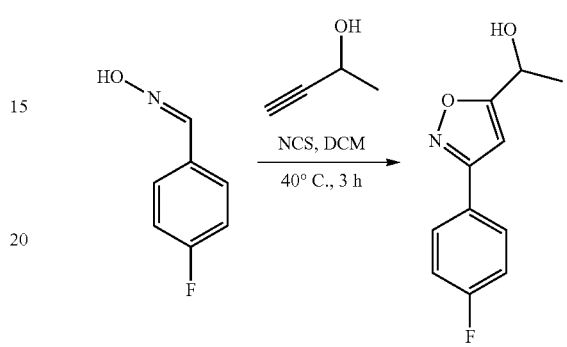

To a stirred solution of 4-fluorobenzaldehyde oxime (0.2 g, 1.4 mmol) in DCM (10 mL) was added N-chlorosuccinamide (0.1 g, 1.4 mmol) and the reaction stirred for 1 hour at room temperature. But-3-yn-2-ol (0.23 g, 1.68 mmol) was added and the reaction mixture stirred at reflux for 3 h. After completion of the reaction (as monitored by TLC), the mixture was extracted with DCM (3×100 mL), the organic layer washed with water (100 mL) followed by brine (100 mL), dried over sodium sulfate, and concentrated under reduced pressure. The crude product was purified by silica gel column chromatography (60-120 mesh; using 50% ethyl acetate in hexanes) to obtain 1-(3-(4-fluorophenyl)isoxazol-5-yl)ethanol as liquid (0.15 g, 50% yield). 1H NMR (400 MHz, CDCl$_3$): δ 7.76 (dd, 2H), 7.05 (t, 2H), 6.48 (s, 1H), 5.04 (q, 1H), 1.63 (d, 3H).

Step 3: 1-(3-(4-Fluorophenyl)isoxazol-5-yl)ethanone

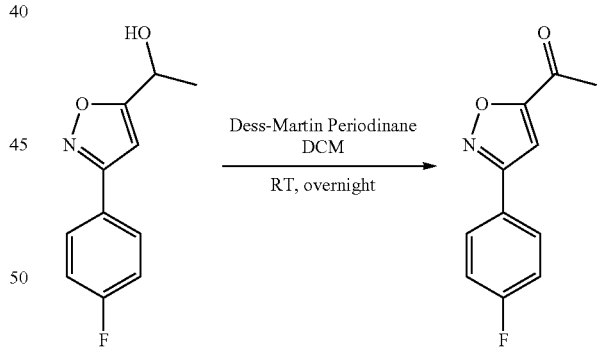

To a stirred solution of 1-(3-(4-fluorophenyl)isoxazol-5-yl)ethanol (0.15 g, 0.724 mmol) in DCM (10 mL) was added Dess-Martin periodinane (0.46 g, 1.08 mmol) at room temperature. The resulting solution was stirred for 16 h. The reaction mixture was filtered and washed with DCM (3×50 mL). The organic layer was washed with water (50 mL) followed by brine solution (50 mL), dried over sodium sulfate and concentrated under reduced pressure to obtain crude product. The crude product was purified by silica gel column chromatography (100-200 mesh; using 80% ethyl acetate in hexane) to obtain 1-(3-(4-fluorophenyl)isoxazol-5-yl)ethanone as off-white solid (0.1 g, 68% yield). 1H NMR (400 MHz, CDCl$_3$): δ 7.81 (t, 2H), 7.20 (s, 1H), 7.17 (d, 2H), 2.66 (s, 3H).

Step 4: 3-(4-Fluorophenyl)-5-(1-(pyridin-4-yl)ethyl) isoxazole

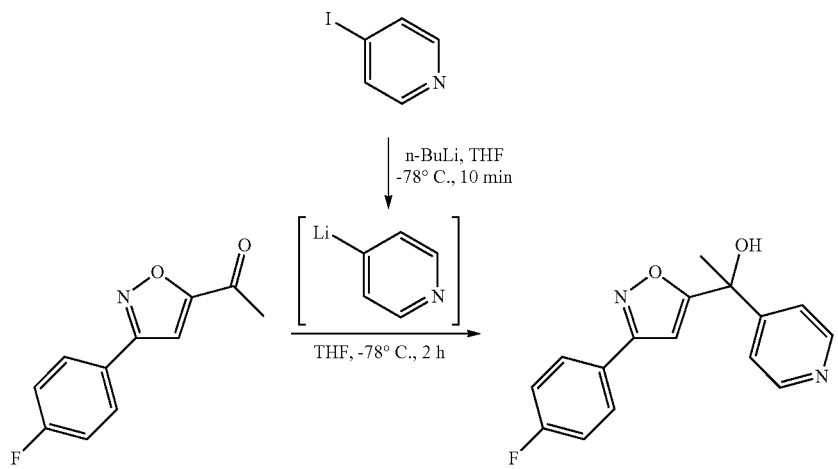

To a stirred solution of 4-iodopyridine (0.3 g, 1.463 mmol) in THF (10 mL) was added n-BuLi (0.6 mL, 0.96 mmol) at −78° C. and stirred for 10 min. A solution of 1-(3-(4-fluorophenyl)isoxazol-5-yl)ethanone (0.1 g, 0.484 mmol) in THF (5 mL) was added to the reaction and the mixture stirred at −78° C. for 2 h. The reaction was quenched with saturated ammonium chloride solution (10 mL) and diluted with ethyl acetate (50 mL). The organic layer was separated, washed with saturated ammonium chloride (3×150 mL) followed by brine solution (2×20 mL). The organic layer was dried over sodium sulfate, filtered and concentrated under reduced pressure to obtain crude product. The crude product was purified by column chromatography (100-200μ silica gel; 50% ethyl acetate in hexane) to obtain 3-(4-fluorophenyl)-5-(1-(pyridin-4-yl)ethyl)isoxazole as off-white solid (0.04 g, 29% yield). 1H NMR (400 MHz, DMSO-d$_6$): δ 8.55 (d, 2H), 7.91 (dd, 2H), 7.46 (d, 2H), 7.32 (t, 2H), 6.81 (s, 1H), 7.04 (s, 1H), 1.86 (s, 3H); LC-MS m/z calculated for [M+H]$^+$ 285.10. found 285.1.

Example 33

(2-(4-Fluorophenyl)thiazol-5-yl)(pyridin-4-yl)methanone (synthetic method of Schemes 1 and 2A)

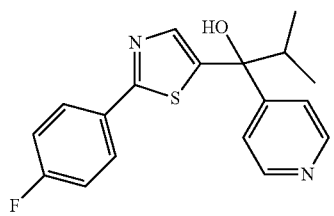 [SMILES: CC(C)C(O)(c1ccncc1)c1cnc(-c2ccc(F)cc2)s1]

Step 1: (2-(4-Fluorophenyl)thiazol-5-yl)(pyridin-4-yl)methanone

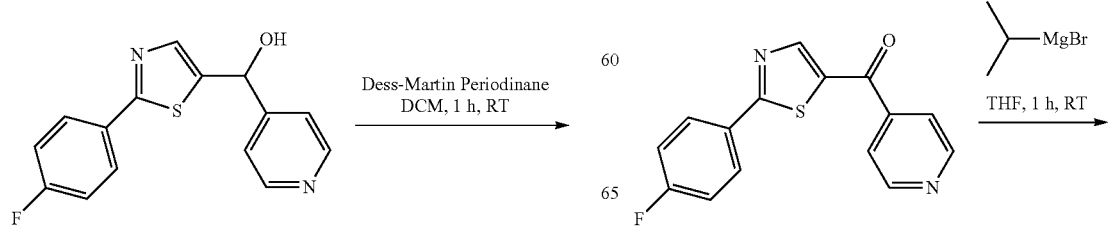

To a stirred solution of (2-(4-fluorophenyl)thiazol-5-yl)(pyridin-4-yl)methanol (0.55 g, 1.92 mol) in DCM (20 mL) was added Dess-Martin periodinane (1.6 g, 3.84 mol) at room temperature. The resulting solution was stirred for 1 h. To the reaction mixture was added NaHCO$_3$ solution (20 mL) and ethyl acetate (50 mL). The organic layer was extracted with ethyl acetate (2×20 mL), washed with brine solution (2×20 mL), dried over anhydrous sodium sulfate and the solvent removed via distillation under reduced pressure. The crude was purified through silica gel (100-200 mesh) column chromatography using 10% methanol in DCM) to obtain (2-(4-fluorophenyl)thiazol-5-yl)(pyridin-4-yl)methanone as off-white solid (0.4 g, 67% yield). 1H NMR (400 MHz, DMSO-d$_6$): δ 8.86 (d, 2H), 8.51 (s, 1H), 8.19 (dd, 2H), 7.82 (d, 2H), 7.45 (t, 2H); LC-MS m/z calculated for [M+H]$^+$ 285.04 found 284.98.

Step 2: 1-(2-(4-Fluorophenyl)thiazol-5-yl)-2-methyl-1-(pyridin-4-yl)propan-1-ol

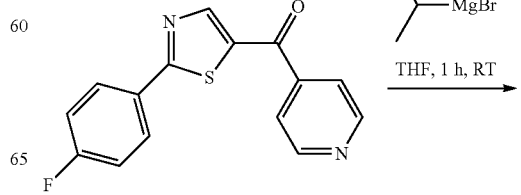

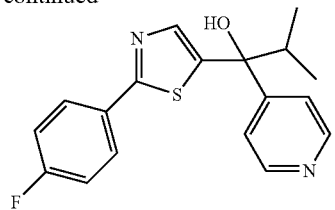

To a stirred solution of (2-(4-fluorophenyl)thiazol-5-yl)(pyridin-4-yl)methanone (0.1 g, 0.352 mmol) in THF (10 mL) was added isopropyl magnesium bromide (0.1 g, 0.704 mmol) at 0° C. The reaction mixture was stirred for 1 hour at room temperature. After completion of the reaction, the reaction mixture was quenched with ammonium chloride (5 mL) at 0° C., extracted with ethyl acetate (2×20 mL), washed with water followed by brine (20 mL), dried over $Na_2SO_4$, and concentrated under reduced pressure. The crude was purifying by the preparative TLC (Mobile phase: 10% MeOH in DCM) to obtain pure 1-(2-(4-fluorophenyl)thiazol-5-yl)-2-methyl-1-(pyridin-4-yl)propan-1-ol (0.023 g, 20% yield). 1H NMR (400 MHz, DMSO-$d_6$): δ 8.52 (d, 2H), 7.92 (t, 3H), 7.56 (d, 2H), 7.27 (t, 2H), 6.22 (s, 1H), 2.79 (t, 1H), 0.98 (d, 3H), 0.71 (d, 3H); LC-MS m/z calculated for [M+H]$^+$ 329.10. found 329.1.

Example 34

1-(3-(4-Fluorophenyl)-1,2,4-oxadiazol-5-yl)-1-(pyridin-4-yl)ethanol (Synthetic Method of Schemes 10B & 1)

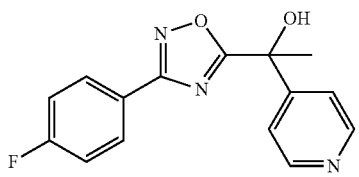

Step 1: Ethyl 2-hydroxy-2-(pyridin-4-yl)propanoate

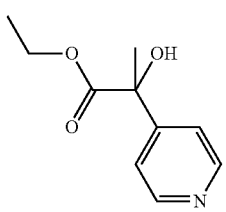

4-Iodopyridine (15.0 g, 73 mmol) was taken up in dry THF (600 mL) and cooled to 0° C. and then ethylmagnesium bromide (3M solution in THF, 41.8 mL) was gradually added, maintaining the temperature at 0° C. over the period of 30 mins. To the above reaction mixture was then added a solution of ethyl 2-oxopropanoate (12.13 g, 104 mmol) in THF (100 mL). The reaction mixture was stirred at 0° C. for 1 hr. The reaction progress was monitored by TLC using solvent system MeOH:DCM (5:95). After completion of reaction, the reaction mixture was quenched with ice-cold water and extracted with EtOAc (3×1 Lit). The combined organic layers were dried over $Na_2SO_4$, and concentrated under vacuum. The crude product residue was combined with a batch of crude product obtained from a second reaction carried out at the same scale, and was purified by column chromatography using silica (100-200 mesh) and solvent system EtOAc:Hexane (4:6) to obtain 7 g (25%) of ethyl 2-hydroxy-2-(pyridin-4-yl)propanoate as a yellow solid. $^1$H NMR (400 MHz, DMSO-$d_6$): δ 8.52 (d, 2H, J=6 Hz), 7.44 (d, 2H, J=6 Hz), 6.2 (s, 1H), 4.08 (q, 2H, J=7.2 Hz), 1.60 (s, 1H), 1.12 (t, 3H, J=7.2 Hz); LC-MS m/z calculated for [M+H]$^+$ 196.09. found 196.2.

Step 2: 4-Fluoro-N'-hydroxybenzimidamide

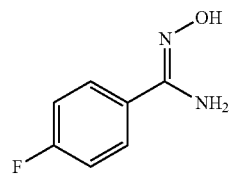 [SMILES: N/C(=N\O)c1ccc(F)cc1]

To a stirred solution of 4-fluorobenzonitrile (10 g, 82.5 mmol) in EtOH (71 mL) was added $NH_2OH.HCl$ (6.42 g, 92.1 mmol), followed by NaOH pellets (3.69 g, 92.1 mmol). The resulting reaction mixture was then heated at reflux for 3 h. The reaction progress was monitored by TLC using solvent system EtOAc:Hexane (1:1). After completion of reaction the solvent was evaporated under reduced pressure and the minimum amount of water (ca. 30 mL) was added to the residue. The mixture was extracted with dichloromethane (3×300 mL), dried over $Na_2SO_4$, and concentrated under vacuum. The crude compound obtained was recrystallized from hot toluene to obtain 8.0 g (63%) of 4-fluoro-N'-hydroxybenzimidamide as a colorless solid. $^1$H NMR (400 MHz, DMSO-$d_6$): δ 9.6 (s, 1H), 7.07-7.67 (m, 2H), 7.18 (t, 2H, J=8.8 Hz), 5.80 (br s, 2H); LC-MS m/z calculated for [M+H]$^+$ 155.05. found 155.1.

Step 3: 1-(3-(4-Fluorophenyl)-1,2,4-oxadiazol-5-yl)-1-(pyridin-4-yl)ethanol

Sodium hydride (60%, 6.00 g, 150 mmol) was taken up in THF (250 mL) under nitrogen atmosphere, and then a solution of 4-fluoro-N'-hydroxybenzimidamide (Step 2; 23.22 g, 150 mmol) in THF (250 mL) was added. The resulting reaction mixture was heated at 50° C. for 15 min, and then a solution of ethyl 2-hydroxy-2-(pyridin-4-yl)propanoate (Step 1; 25 g, 120 mmol) in THF (250 mL) was added. The mixture was stirred for 1 hr at 50° C. The progress of reaction was monitored by TLC using solvent system EtOAc:Hexane (7:3). After completion of reaction, the solvent was concentrated to one third of the total volume. The crude mixture was poured into ice water and extracted with EtOAc (3×500 mL). The combined organic extract was dried over $Na_2SO_4$ and concentrated under vacuum. The crude residue was washed with water several times to obtain a solid which was then washed with hexane (100 mL) followed by 50 mL of chilled ether to obtain 14 g (38%) of 1-(3-(4-fluorophenyl)-1,2,4-oxadiazol-5-yl)-1-(pyridin-4-yl)ethanol as a colorless solid. HPLC purity: 99.4%; $^1$H NMR (400 MHz, DMSO-d$_6$): δ 8.58 (d, 2H, J=5.6 Hz), 8.06-8.03 (m, 2H), 7.51 (d, 2H, J=6.4 Hz), 7.39 (t, 2H, J=8.8 Hz), 7.09 (s, 1H), 1.96 (s, 3H); LC-MS m/z calculated for [M+H]$^+$ 286.09. found 286.1.

Examples 35 & 36

Enantiomer #1 and Enantiomer #2 1-(3-(4-Fluorophenyl)-1,2,4-oxadiazol-5-yl)-1-(pyridin-4-yl)ethanol

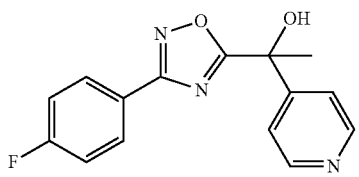

Racemic 1-(3-(4-fluorophenyl)-1,2,4-oxadiazol-5-yl)-1-(pyridin-4-yl)ethanol (Example 34) (20 g) was dissolved in mobile phase (90:10) n-heptane:ethanol containing 0.1% DEA and subjected to chiral HPLC purification (30 mg in 5 mL per injection) using Chiralpak IA column (250 mm×20 mm×5 µm), mobile phase (90:10) n-heptane:ethanol containing 0.1% DEA, flow rate 18.0 mL/min Eluted fractions of the two enantiomers were separately collected and each of these fractions was concentrated to afford 7.55 g (76% recovery) of (−)-1-(3-(4-fluorophenyl)-1,2,4-oxadiazol-5-yl)-1-(pyridin-4-yl)ethanol (Example 35) (Enantiomer #1, 99.78% ee, [α]$_D^{23.6}$−77.4 (c 1.0, MeOH)), and 8.10 g (81% recovery) of (+)-1-(3-(4-fluoro-phenyl)-1,2,4-oxadiazol-5-yl)-1-(pyridin-4-yl)ethanol (Example 36) (Enantiomer #2, 97.07% ee, [α]$_D^{23.3}$+77.26 (c 1.0, MeOH)).

Examples 54 & 55

Enantiomer #1 and Enantiomer #2 of 1-(5-(4-Fluorophenyl)thiazol-2-yl)-1-(pyridin-4-yl)ethanol

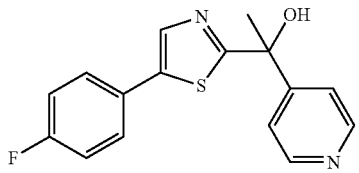 [SMILES: CC(O)(c1ccncc1)c1ncc(-c2ccc(F)cc2)s1]

Racemic 1-(5-(4-fluorophenyl)thiazol-2-yl)-1-(pyridin-4-yl)ethanol (Example 14) (3.5 g), was dissolved in mobile phase (100% ethanol containing 0.1% DEA) and subjected to chiral HPLC purification (50 mg in 5 mL per injection) using ChiralpaklA® IA [250 mm×4.6 mm×5 µm] column, mobile phase 100% ethanol containing 0.1% DEA; flow rate 9.0 mL/min Eluted fractions of the two enantiomers were separately collected and each of these fractions was concentrated to afford 1.6 g (91% recovery) of (−)-1-(5-(4-fluorophenyl)thiazol-2-yl)-1-(pyridin-4-yl)ethanol (Example 54) (Enantiomer #1, 99.8% ee, [α]$_D^{25.2}$−107.30 (c 1.0, DMF)), and 1.5 g (86% recovery) of (+)-1-(5-(4-fluorophenyl)thiazol-2-yl)-1-(pyridin-4-yl)ethanol (Example 55) (Enantiomer #2, 99.0% ee). Enantiomer #2 (1.5 g) was again purified by similar method to obtain 1.0 g (overall 57% recovery) with chiral purity of 99.9% ee, [α]$_D^{24.2}$+107.82 (c 1.0, DMF).

Example 65

1-(2-(4-Fluorophenyl)thiazol-5-yl)-1-(pyridin-4-yl)ethyl acetate (Synthetic Method of Scheme 19)

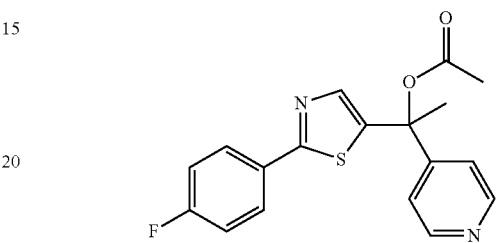

To a stirred solution of 1-(2-(4-fluorophenyl)thiazol-5-yl)-1-(pyridin-4-yl)ethanol (Example 7) (5.0 g, 16.6 mmol) in THF (200 mL) was added KOtBu (4.65 g, 41.5 mmol) at room temperature. The mixture was stirred for 15 mins, and then it was cooled to 0° C. Acetyl chloride (4.73 mL, 66.6 mmol) was added dropwise to the reaction mixture and stifling was continued at 0° C. for 20 min Water (250 mL) was added to the reaction mixture, which was then extracted with EtOAc (4×1 L). The combined organic layers were washed with cold water (3×150 mL) and brine (250 mL), and then concentrated under vacuum. The crude product residue obtained was purified by column chromatography using silica (100-200 mesh) and ethyl acetate/hexane (4:6) as eluent to afford 3.75 g (66%) of 1-(2-(4-fluorophenyl)thiazol-5-yl)-1-(pyridin-4-yl)ethyl acetate as a light brown solid. 1H NMR (400 MHz, CDCl$_3$): δ 8.62 (d, 1H, J=4.8 Hz), 7.87 (m, 2H), 7.62 (s, 1H), 7.29 (d, 2H, J=4.8 Hz), 7.10 (t, 1H, J=8.1 Hz), 2.28 (s, 3H), 2.15 (s, 3H); LC-MS m/z calculated for [M+H]$^+$343.08. found 343.1.

Example 68

1-(2-(4-Fluorophenyl)thiazol-5-yl)-1-(pyridin-4-yl)ethanamine (Synthetic Method of Scheme 18)

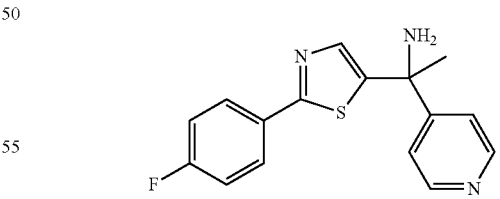

A stirred solution of N-(1-(2-(4-fluorophenyl)thiazol-5-yl)-1-(pyridin-4-yl)ethyl)acetamide (Example 69) (0.04 g, 0.12 mmol) in concentrated HCl (0.07 mL, 3.03 mmol) was heated at 100° C. for 24 hrs in a sealed glass tube. The reaction mixture was then cooled to room temperature and neutralized with 10% NaOH solution (2 mL). The aqueous layer was extracted with ethyl acetate (3×100 mL), and the combined organic layers were concentrated under vacuum. The crude product residue obtained was purified by preparative TLC using eluting solvent as MeOH:CH$_2$Cl$_2$ (3:7) to afford 20 mg (38%) of 1-(2-(4-fluorophenyl)thiazol-5-yl)-1-(Pyridin-4-yl)ethanamine as a colorless solid. $^1$H NMR (400 MHz, DMSO-d$_6$): δ 8.50 (d, 2H, J=5.6 Hz), 7.91-7.88 (m, 2H), 7.70 (s, 1H), 7.51 (d, 2H, J=6.4 Hz), 7.28 (t, 2H, J=8.8 Hz), 2.81 (s, 2H); 1.85 (s, 3H); LC-MS m/z calculated for [M+H]$^+$ 300.09. found 300.1.

Example 69

N-(1-(2-(4-Fluorophenyl)thiazol-5-yl)-1-(pyridin-4-yl)ethyl)acetamide (Synthetic Method of Scheme 18)

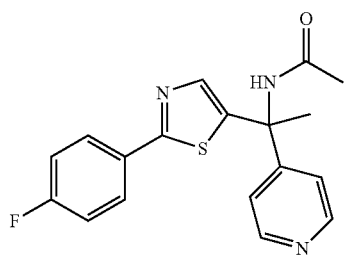 [SMILES: CC(=O)NC(C)(c1ccncc1)c1cnc(-c2ccc(F)cc2)s1]

A stirred solution of 1-(2-(4-fluorophenyl)thiazol-5-yl)-1-(pyridin-4-yl)ethanol (Example 7) (0.450 g, 1.50 mmol) in MeCN (2.25 mL) was heated at 90° C. and then conc. H$_2$SO$_4$ (0.58 mL) in MeCN (2.25 mL) was added. The reaction mixture was stirred at 90° C. for 3 hrs, then it was cooled to room temperature and ice was added. The resulting mixture was neutralized with 10% NaOH solution, extracted with ethyl acetate (3×250 mL), and the combined organic layers were concentrated under vacuum. The crude product obtained was purified by column chromatography using silica gel (100-200 mesh) and MeOH:CH$_2$Cl$_2$ (3:7) as eluent to afford 95 mg (19%) of N-(1-(2-(4-fluorophenyl)thiazol-5-yl)-1-(pyridin-4-yl)ethyl)acetamide as a colorless solid. $^1$H NMR (400 MHz, DMSO-d$_6$): δ 8.72 (br s, 1H), 8.48 (dd, 2H, J=4.4, 1.6 Hz), 7.93 (m, 2H), 7.80 (s, 1H), 7.29 (t, 2H, J=8.8 Hz), 7.20 (dd, 2H, J=4.4, 1.6 Hz); 1.97 (s, 3H), 1.90 (s, 3H), LC-MS m/z calculated for [M+H]$^+$ 342.10. found 342.1.

The following tables, i.e., Tables 1 and 2, provide a summary of the synthetic methods utilized to prepare the Compounds of the Invention identified therein. Table 1 provides the synthetic methods used with reference to the Schemes described above, and Table 2 provides the spectroscopic data obtained and utilized in the characterization of the prepared compounds.

TABLE 1

| Ex. | Structure | Name | Synthesis method (Scheme #) |
|---|---|---|---|
| 1 | 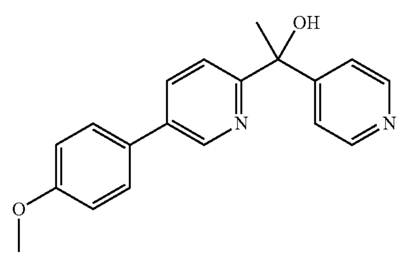 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol | 1 |
| 2 | 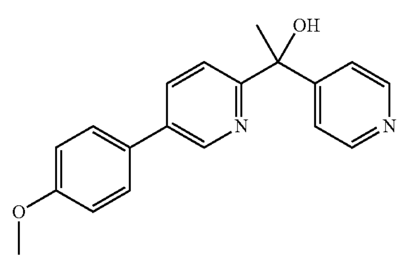 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol, enantiomer #1 | 1 |
| 3 | 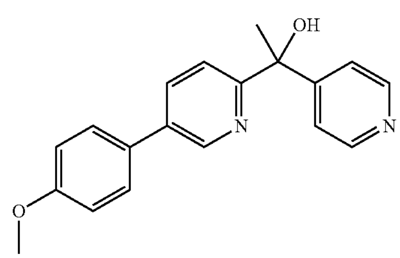 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol, enantiomer #2 | 1 |

TABLE 1-continued

| Ex. | Structure | Name | Synthesis method (Scheme #) |
|---|---|---|---|
| 4 | 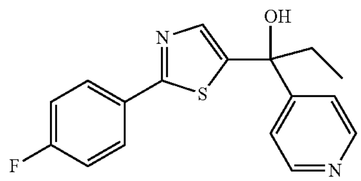 [SMILES: CCC(O)(c1ccncc1)c1cnc(-c2ccc(F)cc2)s1] | 1-(2-(4-fluorophenyl)-thiazol-5-yl)-1-(pyridin-4-yl)propan-1-ol | 1, 2 |
| 5 | 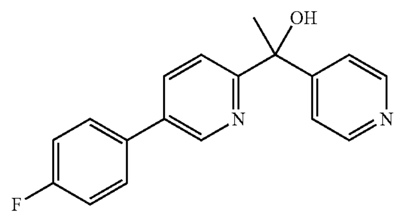 | 1-(5-(4-fluorophenyl)-pyridin-2-yl)-1-(pyridin-4-yl)ethanol | 1 |
| 6 | 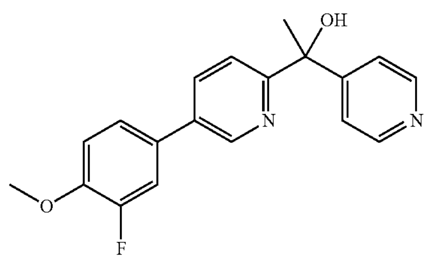 [SMILES: COc1ccc(-c2ccc(C(C)(O)c3ccncc3)nc2)cc1F] | 1-(5-(3-fluoro-4-methoxyphenyl)-pyridin-2-yl)-1-(pyridin-4-yl)ethanol | 1 |
| 7 | 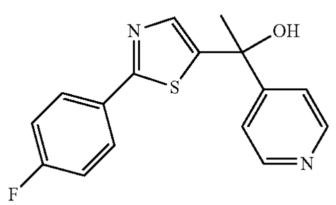 [SMILES: CC(O)(c1ccncc1)c1cnc(-c2ccc(F)cc2)s1] | 1-(2-(4-fluorophenyl)-thiazol-5-yl)-1-(pyridin-4-yl)ethanol | 1, 2, 3 |
| 8 | 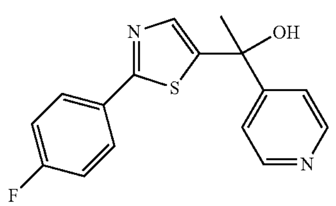 [SMILES: CC(O)(c1ccncc1)c1cnc(-c2ccc(F)cc2)s1] | (+)-1-(2-(4-fluorophenyl)-thiazol-5-yl)-1-(pyridin-4-yl)ethanol (enantiomer #1) | 3 |
| 9 | 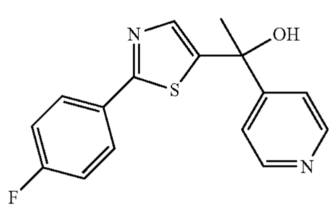 [SMILES: CC(O)(c1ccncc1)c1cnc(-c2ccc(F)cc2)s1] | (−)-1-(2-(4-fluorophenyl)-thiazol-5-yl)-1-(pyridin-4-yl)ethanol (enantiomer #2) | 3 |
| 10 | 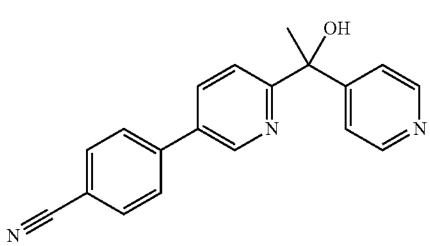 [SMILES: CC(O)(c1ccncc1)c1ccc(-c2ccc(C#N)cc2)cn1] | 4-(6-(1-hydroxy-1-(pyridin-4-yl)-ethyl)pyridin-3-yl)-benzonitrile | 1 |

TABLE 1-continued

| Ex. | Structure | Name | Synthesis method (Scheme #) |
|---|---|---|---|
| 11 | 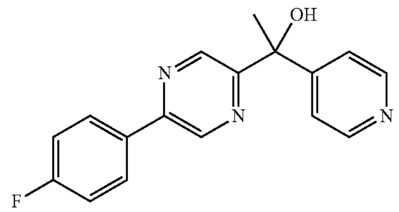 [SMILES: CC(O)(c1ccncc1)c1cnc(-c2ccc(F)cc2)cn1] | 1-(5-(4-fluorophenyl)pyrazin-2-yl)-1-(pyridin-4-yl)ethanol | 4 |
| 12 | 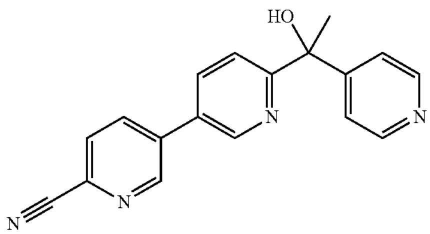 [SMILES: CC(O)(c1ccncc1)c1ccc(-c2ccc(C#N)nc2)cn1] | 6'-(1-hydroxy-1-pyridin-4-ylethyl)-3,3'-bipyridine-6-carbonitrile | 1 |
| 13 | 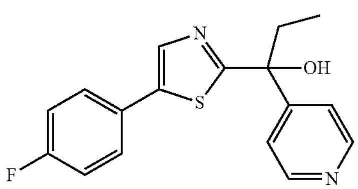 | 1-[5-(4-fluorophenyl)-1,3-thiazol-2-yl]-1-pyridin-4-ylpropan-1-ol | 7 |
| 14 | 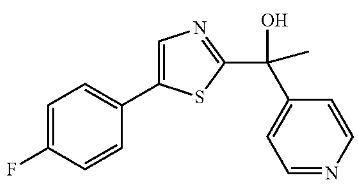 [SMILES: CC(O)(c1ccncc1)c1ncc(-c2ccc(F)cc2)s1] | 1-[5-(4-fluorophenyl)-1,3-thiazol-2-yl]-1-pyridin-4-ylethanol | 3 |
| 15 | 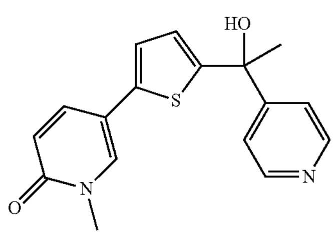 [SMILES: Cn1cc(-c2ccc(C(C)(O)c3ccncc3)s2)ccc1=O] | 5-[5-(1-hydroxy-1-pyridin-4-ylethyl)thien-2-yl]-1-methylpyridin-2(1H)-one | 6 |
| 16 | 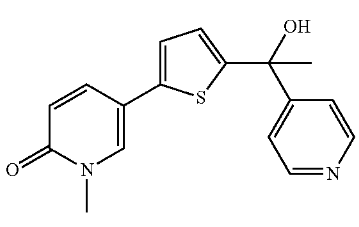 [SMILES: Cn1cc(-c2ccc(C(C)(O)c3ccncc3)s2)ccc1=O] | (+)-5-[5-(1-Hydroxy-1-pyridin-4-yl-ethyl)-thiophen-2-yl]-1-methyl-1H-pyridin-2-one (enantiomer #1) | 6 |
| 17 | 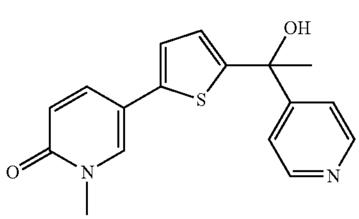 | (−)-5-[5-(1-Hydroxy-1-pyridin-4-yl-ethyl)-thiophen-2-yl]-1-methyl-1H-pyridin-2-one (enantiomer #2) | 6 |

TABLE 1-continued

| Ex. | Structure | Name | Synthesis method (Scheme #) |
|---|---|---|---|
| 18 | 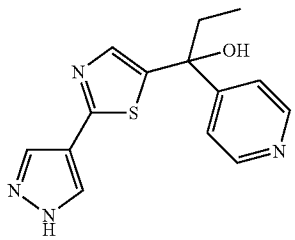 [SMILES: CCC(O)(c1ccncc1)c1cnc(-c2cn[nH]c2)s1] | 1-[2-(1H-pyrazol-4-yl)-1,3-thiazol-5-yl]-1-pyridin-4-ylpropan-1-ol | 1, 2, 3 |
| 19 | 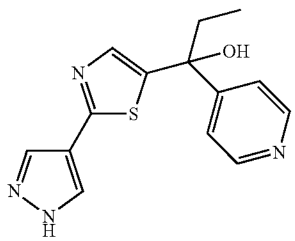 [SMILES: CCC(O)(c1ccncc1)c1cnc(-c2cn[nH]c2)s1] | (−)-1-[2-(1H-pyrazol-4-yl)-1,3-thiazol-5-yl]-1-pyridin-4-ylpropan-1-ol, (enantiomer #1) | 3 |
| 20 | 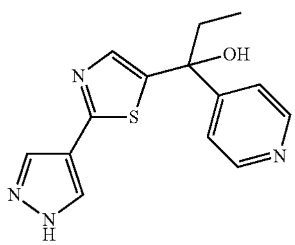 [SMILES: CCC(O)(c1ccncc1)c1cnc(-c2cn[nH]c2)s1] | (+)-1-[2-(1H-pyrazol-4-yl)-1,3-thiazol-5-yl]-1-pyridin-4-ylpropan-1-ol, (enantiomer #2) | 3 |
| 21 | 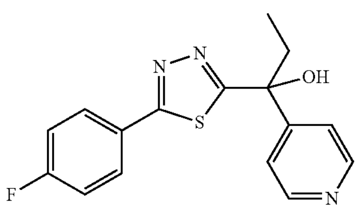 [SMILES: CCC(O)(c1ccncc1)c1nnc(-c2ccc(F)cc2)s1] | 1-[5-(4-fluorophenyl)-1,3,4-thiadiazol-2-yl]-1-pyridin-4-ylpropan-1-ol | 9, 2, 1 |
| 22 | 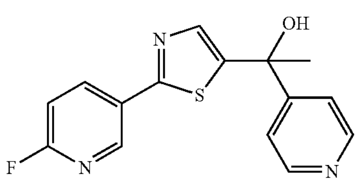 [SMILES: CC(O)(c1ccncc1)c1cnc(-c2ccc(F)nc2)s1] | 1-[2-(6-fluoropyridin-3-yl)-1,3-thiazol-5-yl]-1-pyridin-4-ylethanol | 6 |
| 23 | 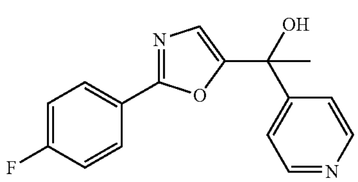 [SMILES: CC(O)(c1ccncc1)c1cnc(-c2ccc(F)cc2)o1] | 1-[2-(4-fluorophenyl)-1,3-oxazol-5-yl]-1-pyridin-4-ylethanol | 7 |
| 24 | 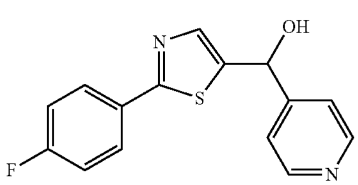 [SMILES: OC(c1ccncc1)c1cnc(-c2ccc(F)cc2)s1] | [2-(4-fluorophenyl)-1,3-thiazol-5-yl](pyridin-4-yl)methanol | 3 |

| Ex. | Structure | Name | Synthesis method (Scheme #) |
|---|---|---|---|
| 25 | 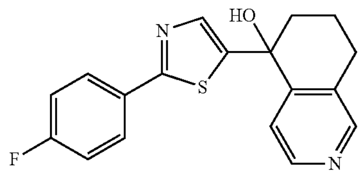 [SMILES: OC1(c2cnc(-c3ccc(F)cc3)s2)CCCc2cnccc21] | 5-[2-(4-Fluoro-phenyl)-thiazol-5-yl]-5,6,7,8-tetrahydro-isoquinolin-5-ol | 3 |
| 26 | 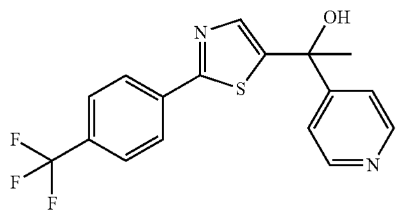 [SMILES: CC(O)(c1ccncc1)c1cnc(-c2ccc(C(F)(F)F)cc2)s1] | 1-Pyridin-4-yl-1-[2-(4-trifluoromethyl-phenyl)-thiazol-5-yl]-ethanol | 3 |
| 27 | 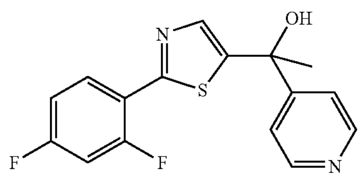 [SMILES: CC(O)(c1ccncc1)c1cnc(-c2ccc(F)cc2F)s1] | 1-[2-(2,4-Difluoro-phenyl)-thiazol-5-yl]-1-pyridin-4-yl-ethanol | 3 |
| 28 | 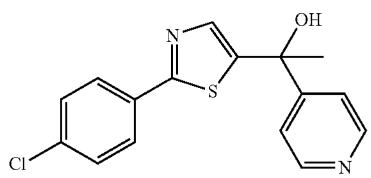 [SMILES: CC(O)(c1ccncc1)c1cnc(-c2ccc(Cl)cc2)s1] | 1-[2-(4-Chloro-phenyl)-thiazol-5-yl]-1-pyridin-4-yl-ethanol | 3 |
| 29 | 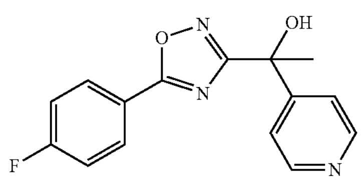 [SMILES: CC(O)(c1ccncc1)c1noc(-c2ccc(F)cc2)n1] | 1-[5-(4-Fluoro-phenyl)-[1,2,4]oxadiazol-3-yl]-1-pyridin-4-yl-ethanol | 10A, 1 |
| 30 | 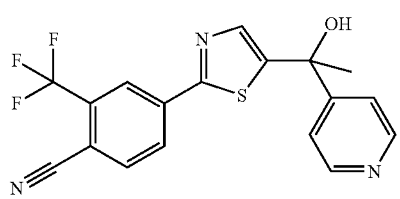 [SMILES: CC(O)(c1ccncc1)c1cnc(-c2ccc(C#N)c(C(F)(F)F)c2)s1] | 4-[5-(1-Hydroxy-1-pyridin-4-yl-ethyl)-thiazol-2-yl]-2-trifluoromethyl-benzonitrile | 8A, 3 |
| 31 | 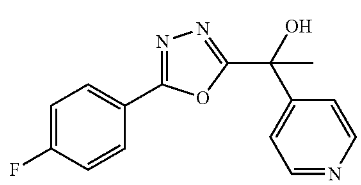 [SMILES: CC(O)(c1ccncc1)c1nnc(-c2ccc(F)cc2)o1] | 1-[5-(4-Fluoro-phenyl)-[1,3,4]oxadiazol-2-yl]-1-pyridin-4-yl-ethanol | 11, 3 |
| 32 | 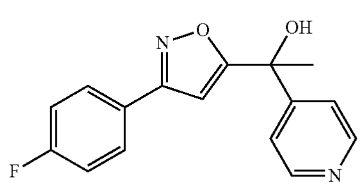 | 1-[3-(4-Fluoro-phenyl)-isoxazol-5-yl]-1-pyridin-4-yl-ethanol | 12, 1 |

TABLE 1-continued

| Ex. | Structure | Name | Synthesis method (Scheme #) |
|---|---|---|---|
| 33 | 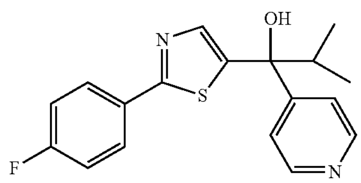 [SMILES: CC(C)C(O)(c1ccncc1)c1cnc(-c2ccc(F)cc2)s1] | 1-[2-(4-Fluoro-phenyl)-thiazol-5-yl]-2-methyl-1-pyridin-4-yl-propan-1-ol | 1, 2A |
| 34 | 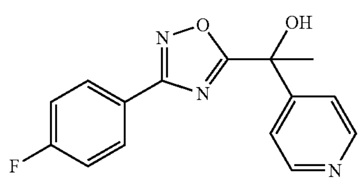 | 1-(3-(4-Fluorophenyl)-1,2,4-oxadiazol-5-yl)-1-(pyridin-4-yl)ethanol | 10B, 1 |
| 35 | 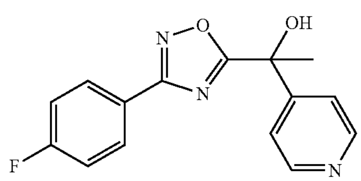 | (−)-1-(3-(4-Fluorophenyl)-1,2,4-oxadiazol-5-yl)-1-(pyridin-4-yl)ethanol (enantiomer #1) | 10B, 1 |
| 36 | 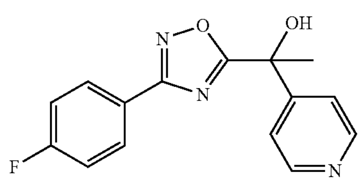 | (+)-1-(3-(4-Fluorophenyl)-1,2,4-oxadiazol-5-yl)-1-(pyridin-4-yl)ethanol (enantiomer #2) | 10B, 1 |
| 37 | 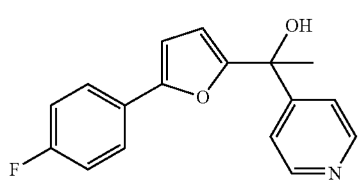 [SMILES: CC(O)(c1ccncc1)c1ccc(-c2ccc(F)cc2)o1] | 1-(5-(4-fluorophenyl)furan-2-yl)-1-(pyridin-4-yl)ethanol | 8B, 3 |
| 38 | 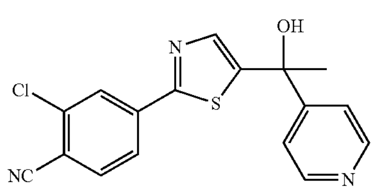 [SMILES: CC(O)(c1ccncc1)c1cnc(-c2ccc(C#N)c(Cl)c2)s1] | 2-chloro-4-(5-(1-hydroxy-1-(pyridin-4-yl)ethyl)thiazol-2-yl)benzonitrile | 3 |
| 39 | 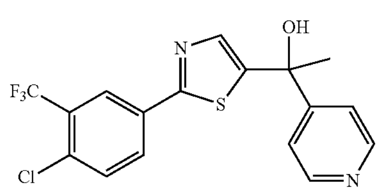 [SMILES: CC(O)(c1ccncc1)c1cnc(-c2ccc(Cl)c(C(F)(F)F)c2)s1] | 1-(2-(4-chloro-3-(trifluoromethyl)phenyl)thiazol-5-yl)-1-(pyridin-4-yl)ethanol | 3 |
| 40 | 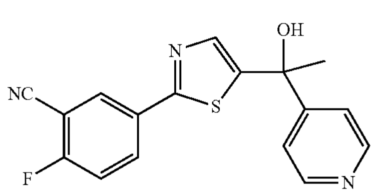 | 2-fluoro-5-(5-(1-hydroxy-1-(pyridin-4-yl)ethyl)thiazol-2-yl)benzonitrile | 8A, 3 |

TABLE 1-continued

| Ex. | Structure | Name | Synthesis method (Scheme #) |
|---|---|---|---|
| 41 | 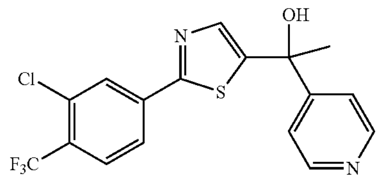 | 1-(2-(3-chloro-4-(trifluoromethyl)phenyl)thiazol-5-yl)-1-(pyridin-4-yl)ethanol | 8A, 3 |
| 42 | 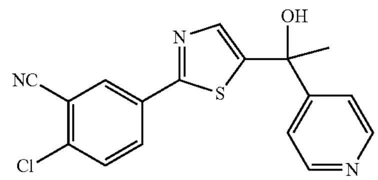 [SMILES: CC(O)(c1ccncc1)c1cnc(-c2ccc(Cl)c(C#N)c2)s1] | 2-chloro-5-(5-(1-hydroxy-1-(pyridin-4-yl)ethyl)thiazol-2-yl)benzonitrile | 3 |
| 43 | 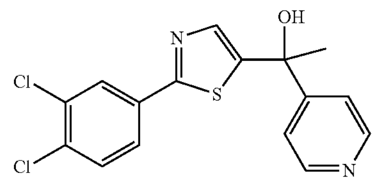 [SMILES: CC(O)(c1ccncc1)c1cnc(-c2ccc(Cl)c(Cl)c2)s1] | 1-(2-(3,4-dichlorophenyl)thiazol-5-yl)-1-(pyridin-4-yl)ethanol | 3 |
| 44 | 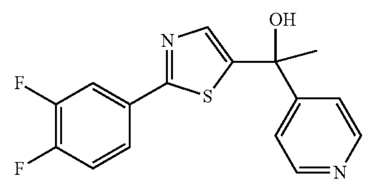 [SMILES: CC(O)(c1ccncc1)c1cnc(-c2ccc(F)c(F)c2)s1] | 1-(2-(3,4-difluorophenyl)thiazol-5-yl)-1-(pyridin-4-yl)ethanol | 3 |
| 45 | 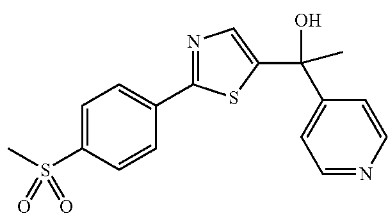 [SMILES: CC(O)(c1ccncc1)c1cnc(-c2ccc(S(C)(=O)=O)cc2)s1] | 1-(2-(4-(methylsulfonyl)phenyl)thiazol-5-yl)-1-(pyridin-4-yl)ethanol | 3 |
| 46 | 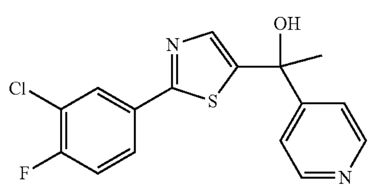 [SMILES: CC(O)(c1ccncc1)c1cnc(-c2ccc(F)c(Cl)c2)s1] | 1-(2-(3-chloro-4-fluorophenyl)thiazol-5-yl)-1-(pyridin-4-yl)ethanol | 3 |
| 47 | 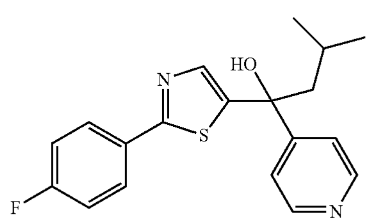 [SMILES: CC(C)CC(O)(c1ccncc1)c1cnc(-c2ccc(F)cc2)s1] | 1-(2-(4-fluorophenyl)thiazol-5-yl)-3-methyl-1-(pyridin-4-yl)butan-1-ol | 3, 2A |
| 48 | 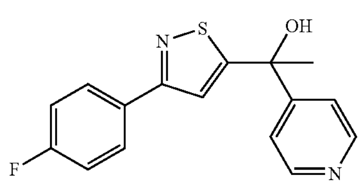 | 1-(3-(4-fluorophenyl)isothiazol-5-yl)-1-(pyridin-4-yl)ethanol | 13, 3 |

TABLE 1-continued

| Ex. | Structure | Name | Synthesis method (Scheme #) |
|---|---|---|---|
| 49 | 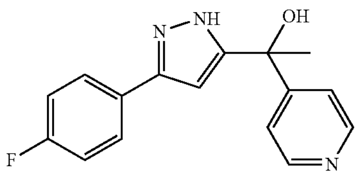 [SMILES: CC(O)(c1ccncc1)c1cc(-c2ccc(F)cc2)n[nH]1] | 1-(3-(4-fluorophenyl)-1H-pyrazol-5-yl)-1-(pyridin-4-yl)ethanol | 14, 2A |
| 50 | 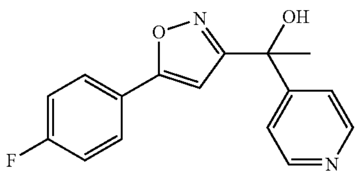 | 1-(5-(4-fluorophenyl)isoxazol-3-yl)-1-(pyridin-4-yl)ethanol | 15, 2A |
| 51 | 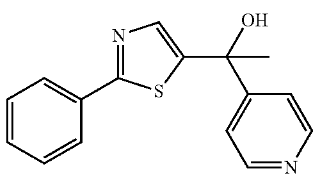 [SMILES: CC(O)(c1ccncc1)c1cnc(-c2ccccc2)s1] | 1-(2-phenylthiazol-5-yl)-1-(pyridin-4-yl)ethanol | 3 |
| 52 | 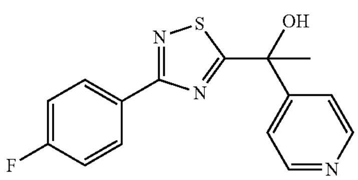 | 1-(3-(4-fluorophenyl)-1,2,4-thiadiazol-5-yl)-1-(pyridin-4-yl)ethanol | 16, 1 |
| 53 | 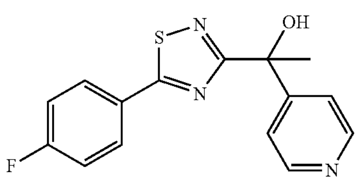 [SMILES: CC(O)(c1ccncc1)c1nsc(-c2ccc(F)cc2)n1] | 1-(5-(4-fluorophenyl)-1,2,4-thiadiazol-3-yl)-1-(pyridin-4-yl)ethanol | 4, 17, 1 |
| 54 | 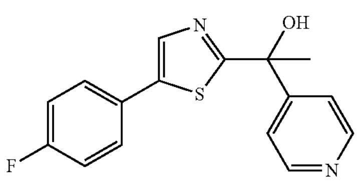 [SMILES: CC(O)(c1ccncc1)c1ncc(-c2ccc(F)cc2)s1] | (−)-1-(5-(4-fluorophenyl)thiazol-2-yl)-1-(pyridin-4-yl)ethanol (enantiomer #1) | 3 |
| 55 | 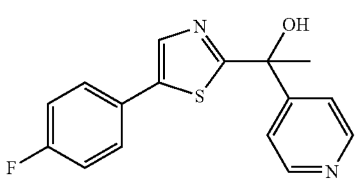 [SMILES: CC(O)(c1ccncc1)c1ncc(-c2ccc(F)cc2)s1] | (+)-1-(5-(4-fluorophenyl)thiazol-2-yl)-1-(pyridin-4-yl)ethanol (enantiomer #2) | 3 |
| 56 | 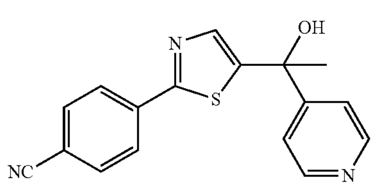 [SMILES: CC(O)(c1ccncc1)c1cnc(-c2ccc(C#N)cc2)s1] | 4-(5-(1-hydroxy-1-(pyridin-4-yl)ethyl)thiazol-2-yl)benzonitrile | 3 |

TABLE 1-continued

| Ex. | Structure | Name | Synthesis method (Scheme #) |
|---|---|---|---|
| 57 | 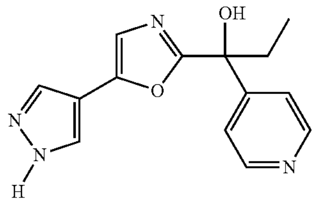 [SMILES: CCC(O)(c1ccncc1)c1ncc(-c2cn[nH]c2)o1] | 1-(5-(1H-pyrazol-4-yl)oxazol-2-yl)-1-(pyridin-4-yl)propan-1-ol | 3 |
| 58 | 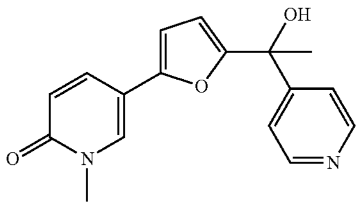 [SMILES: Cn1cc(-c2ccc(C(C)(O)c3ccncc3)o2)ccc1=O] | 5-(5-(1-hydroxy-1-(pyridin-4-yl)ethyl)furan-2-yl)-1-methylpyridin-2(1H)-one | 6 |
| 59 | 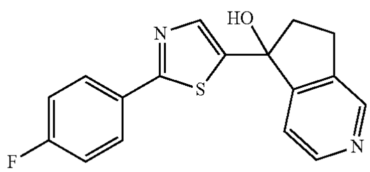 [SMILES: OC1(c2cnc(-c3ccc(F)cc3)s2)CCc2cnccc21] | 5-(2-(4-fluorophenyl)thiazol-5-yl)-6,7-dihydro-5H-cyclopenta[c]pyridin-5-ol | 3 |
| 60 | 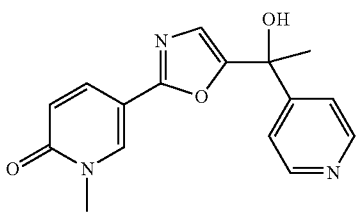 [SMILES: Cn1cc(-c2ncc(C(C)(O)c3ccncc3)o2)ccc1=O] | 5-(5-(1-hydroxy-1-(pyridin-4-yl)ethyl)oxazol-2-yl)-1-methylpyridin-2(1H)-one | 8C, 3 |
| 61 | 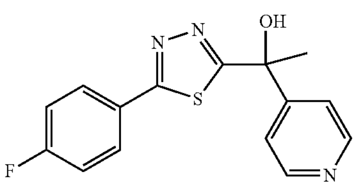 [SMILES: CC(O)(c1ccncc1)c1nnc(-c2ccc(F)cc2)s1] | 1-(5-(4-fluorophenyl)-1,3,4-thiadiazol-2-yl)-1-(pyridin-4-yl)ethanol | 9, 2, 1 |
| 62 | 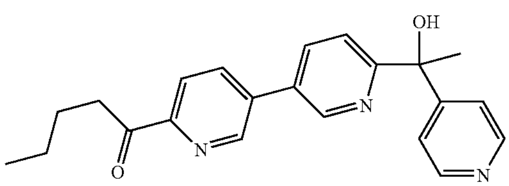 [SMILES: CCCCC(=O)c1ccc(-c2ccc(C(C)(O)c3ccncc3)nc2)cn1] | 1-(6'-(1-hydroxy-1-(pyridin-4-yl)ethyl)-[3,3'-bipyridin]-6-yl)pentan-1-one | 1 |
| 63 | 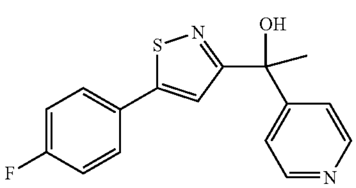 [SMILES: CC(O)(c1ccncc1)c1cc(-c2ccc(F)cc2)sn1] | 1-(5-(4-fluorophenyl)isothiazol-3-yl)-1-(pyridin-4-yl)ethanol | 7, 17, 1 |
| 64 | 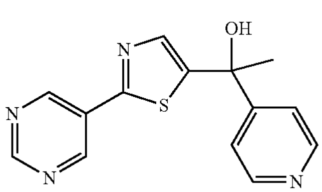 [SMILES: CC(O)(c1ccncc1)c1cnc(-c2cncnc2)s1] | 1-(pyridin-4-yl)-1-(2-(pyrimidin-5-yl)thiazol-5-yl)ethanol | 3 |

TABLE 1-continued
| Ex. | Structure | Name | Synthesis method (Scheme #) |
|---|---|---|---|
| 65 | 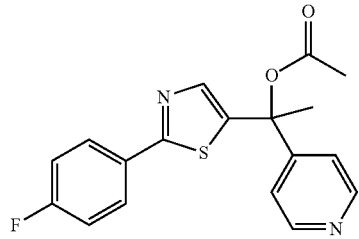 [SMILES: CC(=O)OC(C)(c1ccncc1)c1cnc(-c2ccc(F)cc2)s1] | 1-(2-(4-fluorophenyl)thiazol-5-yl)-1-(pyridin-4-yl)ethyl acetate | 19 |
| 66 | 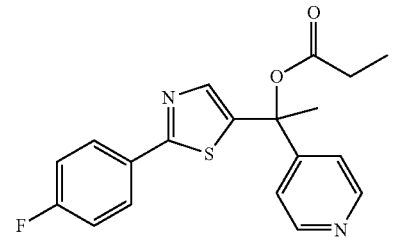 [SMILES: CCC(=O)OC(C)(c1ccncc1)c1cnc(-c2ccc(F)cc2)s1] | 1-(2-(4-fluorophenyl)thiazol-5-yl)-1-(pyridin-4-yl)ethyl propionate | 19 |
| 67 | 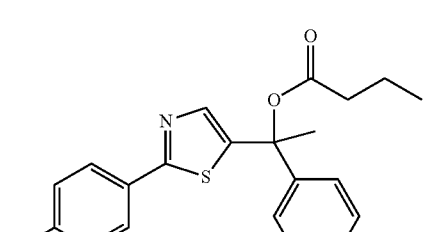 | 1-(2-(4-fluorophenyl)thiazol-5-yl)-1-(pyridin-4-yl)ethyl butyrate | 19 |
| 68 | 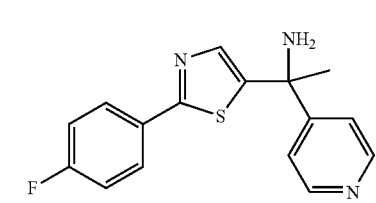 [SMILES: CC(N)(c1ccncc1)c1cnc(-c2ccc(F)cc2)s1] | 1-(2-(4-fluorophenyl)thiazol-5-yl)-1-(pyridin-4-yl)ethanamine | 18 |
| 69 | 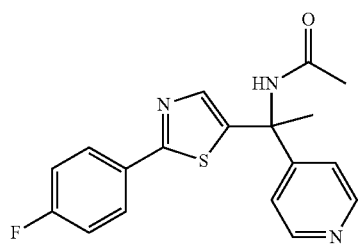 | N-(1-(2-(4-fluorophenyl)thiazol-5-yl)-1-(pyridin-4-yl)ethyl)acetamide | 18 |

All compounds that have a chiral center are racemic mixtures, except as indicated.

TABLE 2

| Ex. | Structure | Name | Exact mass | LC-MS [M + H]+ (m/z) | LC-MS retention time (min) |
| --- | --- | --- | --- | --- | --- |
| 1 | 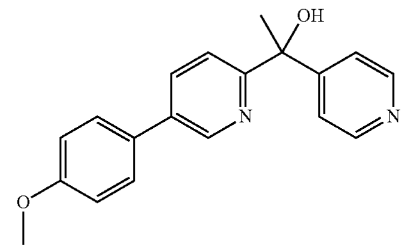 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol | 306.14 | 307.3 | 1.17 |
| 2 | 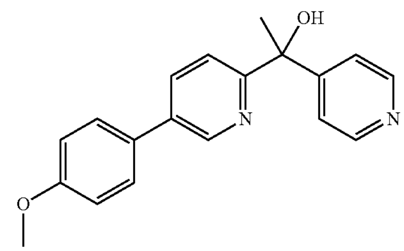 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol, enantiomer #1 | 306.14 | 307.1 | 1.15 |
| 3 | 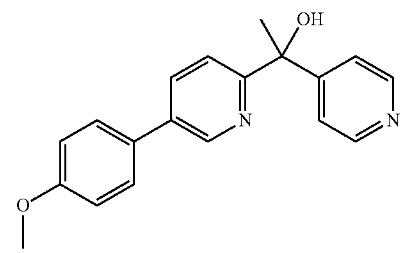 [SMILES: COc1ccc(-c2ccc(C(C)(O)c3ccncc3)nc2)cc1] | 1-(5-(4-methoxyphenyl)-pyridin-2-yl)-1-(pyridin-4-yl)-ethanol, enantiomer #2 | 306.14 | 307.1 | 1.15 |
| 4 | 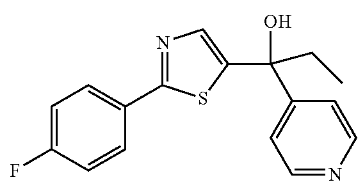 [SMILES: CCC(O)(c1ccncc1)c1cnc(-c2ccc(F)cc2)s1] | 1-(2-(4-fluorophenyl)-thiazol-5-yl)-1-(pyridin-4-yl) propan-1-ol | 314.09 | 315.1 | 1.60 |
| 5 | 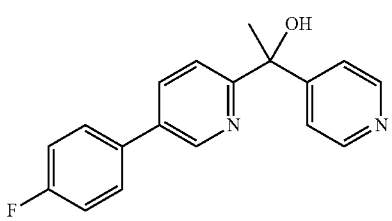 | 1-(5-(4-fluorophenyl)-pyridin-2-yl)-1-(pyridin-4-yl)ethanol | 294.12 | 295.5 | 1.49 |
| 6 | 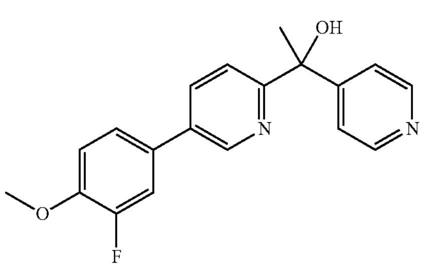 [SMILES: COc1ccc(-c2ccc(C(C)(O)c3ccncc3)nc2)cc1F] | 1-(5-(3-fluoro-4-methoxyphenyl)-pyridin-2-yl)-1-(pyridin-4-yl)ethanol | 324.13 | 325.5 | 1.46 |

TABLE 2-continued

| Ex. | Structure | Name | Exact mass | LC-MS [M + H]+ (m/z) | LC-MS retention time (min) |
|---|---|---|---|---|---|
| 7 | 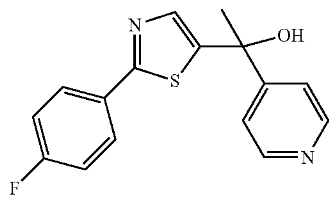 [SMILES: CC(O)(c1ccncc1)c1cnc(-c2ccc(F)cc2)s1] | 1-(2-(4-fluorophenyl)-thiazol-5-yl)-1-(pyridin-4-yl)ethanol | 300.07 | 301.6 | 1.01 |
| 8 | 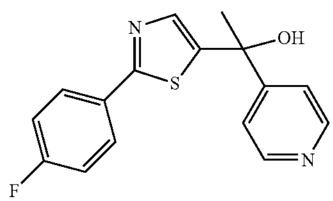 [SMILES: CC(O)(c1ccncc1)c1cnc(-c2ccc(F)cc2)s1] | (+)-1-(2-(4-fluorophenyl)-thiazol-5-yl)-1-(pyridin-4-yl)ethanol (enantiomer #1) | 300.07 | 301.5 | 1.08 |
| 9 | 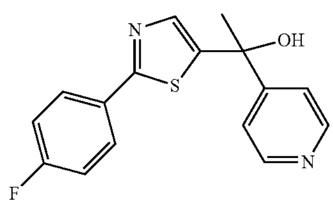 [SMILES: CC(O)(c1ccncc1)c1cnc(-c2ccc(F)cc2)s1] | (−)-1-(2-(4-fluorophenyl)-thiazol-5-yl)-1-(pyridin-4-yl)ethanol (enantiomer #2) | 300.07 | 301.5 | 1.09 |
| 10 | 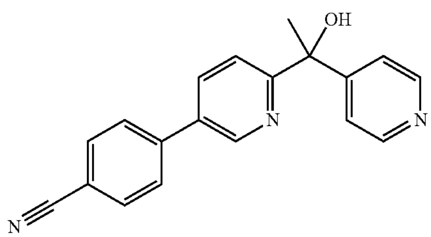 [SMILES: CC(O)(c1ccncc1)c1ccc(-c2ccc(C#N)cc2)cn1] | 4-(6-(1-hydroxy-1-(pyridin-4-yl)-ethyl)pyridin-3-yl)-benzonitrile | 301.12 | 302.2 | 0.46 |
| 11 | 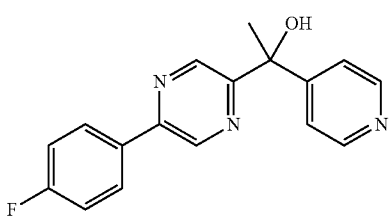 [SMILES: CC(O)(c1ccncc1)c1cnc(-c2ccc(F)cc2)cn1] | 1-(5-(4-fluorophenyl)pyrazin-2-yl)-1-(pyridin-4-yl)ethanol | 295.11 | 296.1 | 0.82 |
| 12 | 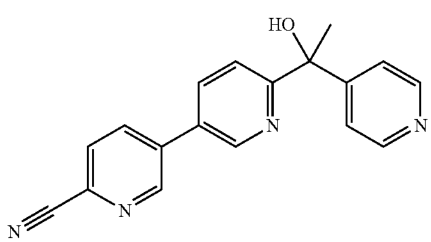 [SMILES: CC(O)(c1ccncc1)c1ccc(-c2ccc(C#N)nc2)cn1] | 6'-(1-hydroxy-1-pyridin-4-ylethyl)-3,3'-bipyridine-6-carbonitrile | 302.12 | 303.1 | 1.50 |
| 13 | 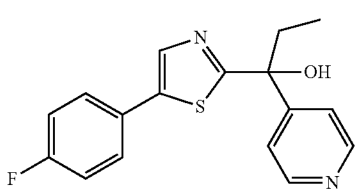 [SMILES: CCC(O)(c1ccncc1)c1ncc(-c2ccc(F)cc2)s1] | 1-[5-(4-fluorophenyl)-1,3-thiazol-2-yl]-1-pyridin-4-ylpropan-1-ol | 314.09 | 315.1 | 1.01 |

TABLE 2-continued

| Ex. | Structure | Name | Exact mass | LC-MS [M + H]+ (m/z) | LC-MS retention time (min) |
| --- | --- | --- | --- | --- | --- |
| 14 | 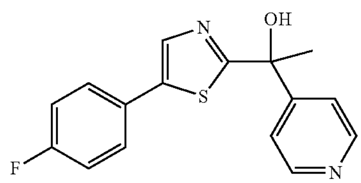 [SMILES: CC(O)(c1ccncc1)c1ncc(-c2ccc(F)cc2)s1] | 1-[5-(4-fluorophenyl)-1,3-thiazol-2-yl]-1-pyridin-4-ylethanol | 300.07 | 301.4 | 0.92 |
| 15 | 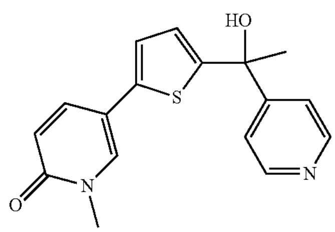 [SMILES: Cn1cc(-c2ccc(C(C)(O)c3ccncc3)s2)ccc1=O] | 5-[5-(1-hydroxy-1-pyridin-4-ylethyl)thien-2-yl]-1-methylpyridin-2(1H)-one | 312.09 | 313.1 | 0.40 |
| 16 | 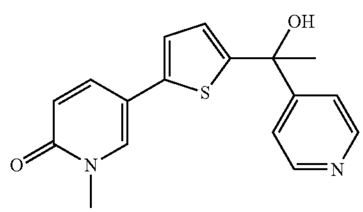 [SMILES: Cn1cc(-c2ccc(C(C)(O)c3ccncc3)s2)ccc1=O] | (+)-5-[5-(1-Hydroxy-1-pyridin-4-yl-ethyl)-thiophen-2-yl]-1-methyl-1H-pyridin-2-one (enantiomer #1) | 312.09 | 313.6 | 0.95 |
| 17 | 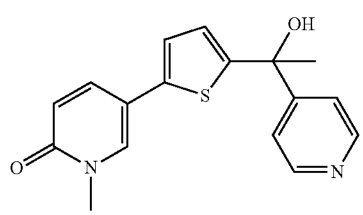 | (−)-5-[5-(1-Hydroxy-1-pyridin-4-yl-ethyl)-thiophen-2-yl]-1-methyl-1H-pyridin-2-one (enantiomer #2) | 312.09 | 313.6 | 0.95 |
| 18 | 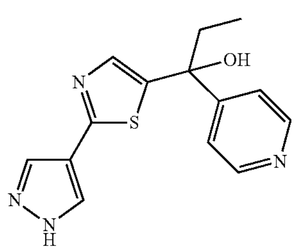 [SMILES: CCC(O)(c1ccncc1)c1cnc(-c2cn[nH]c2)s1] | 1-[2-(1H-pyrazol-4-yl)-1,3-thiazol-5-yl]-1-pyridin-4-ylpropan-1-ol | 286.09 | 287.1 | 0.51 |
| 19 | 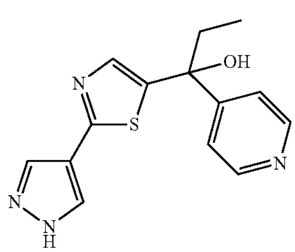 [SMILES: CCC(O)(c1ccncc1)c1cnc(-c2cn[nH]c2)s1] | (−)-1-[2-(1H-pyrazol-4-yl)-1,3-thiazol-5-yl]-1-pyridin-4-ylpropan-1-ol (enantiomer #1) | 286.09 | 287.1 | 0.78 |

TABLE 2-continued

| Ex. | Structure | Name | Exact mass | LC-MS [M + H]+ (m/z) | LC-MS retention time (min) |
|---|---|---|---|---|---|
| 20 | 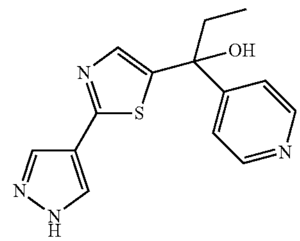 [SMILES: CCC(O)(c1ccncc1)c1cnc(-c2cn[nH]c2)s1] | (+)-1-[2-(1H-pyrazol-4-yl)-1,3-thiazol-5-yl]-1-pyridin-4-ylpropan-1-ol (enantiomer #2) | 286.09 | 287.1 | 0.85 |
| 21 | 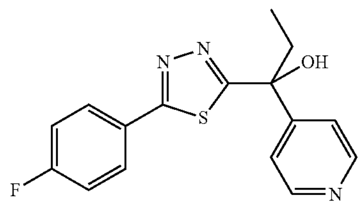 [SMILES: CCC(O)(c1ccncc1)c1nnc(-c2ccc(F)cc2)s1] | 1-[5-(4-fluorophenyl)-1,3,4-thiadiazol-2-yl]-1-pyridin-4-ylpropan-1-ol | 315.08 | 316.1 | 1.29 |
| 22 | 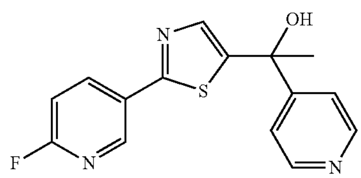 [SMILES: CC(O)(c1ccncc1)c1cnc(-c2ccc(F)cc2)o1] | 1-[2-(6-fluoropyridin-3-yl)-1,3-thiazol-5-yl]-1-pyridin-4-ylethanol | 301.07 | 302.1 | 1.10 |
| 23 | 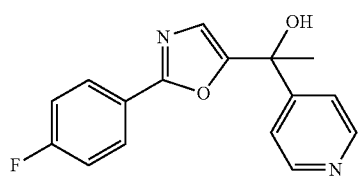 | 1-[2-(4-fluorophenyl)-1,3-oxazol-5-yl]-1-pyridin-4-ylethanol | 284.10 | 285.1 | 1.15 |
| 24 | 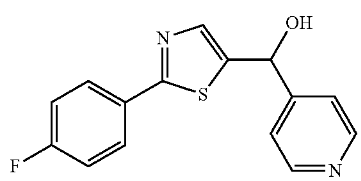 [SMILES: OC(c1ccncc1)c1cnc(-c2ccc(F)cc2)s1] | [2-(4-fluorophenyl)-1,3-thiazol-5-yl](pyridin-4-yl)methanol | 286.06 | 287.0 | 4.97 |
| 25 | 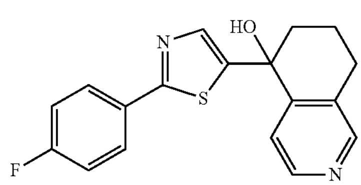 [SMILES: OC1(c2cnc(-c3ccc(F)cc3)s2)CCCc2cnccc21] | 5-[2-(4-Fluorophenyl)-thiazol-5-yl]-5,6,7,8-tetrahydro-isoquinolin-5-ol | 326.09 | 327.1 | 5.49 |
| 26 | 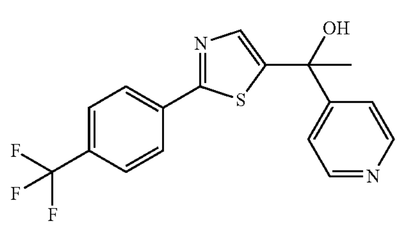 [SMILES: CC(O)(c1ccncc1)c1cnc(-c2ccc(C(F)(F)F)cc2)s1] | 1-Pyridin-4-yl-1-[2-(4-trifluoromethyl-phenyl)-thiazol-5-yl]-ethanol | 350.07 | 351.0 | 1.47 |

TABLE 2-continued

| Ex. | Structure | Name | Exact mass | LC-MS [M + H]+ (m/z) | LC-MS retention time (min) |
| --- | --- | --- | --- | --- | --- |
| 27 | 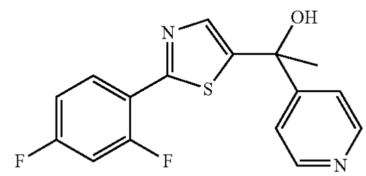 [SMILES: CC(O)(c1ccncc1)c1cnc(-c2ccc(F)cc2F)s1] | 1-[2-(2,4-Difluoro-phenyl)-thiazol-5-yl]-1-pyridin-4-yl-ethanol | 318.06 | 319.0 | 1.32 |
| 28 | 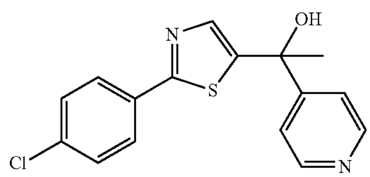 [SMILES: CC(O)(c1ccncc1)c1cnc(-c2ccc(Cl)cc2)s1] | 1-[2-(4-Chloro-phenyl)-thiazol-5-yl]-1-pyridin-4-yl-ethanol | 316.04 | 317.4 | 1.40 |
| 29 | 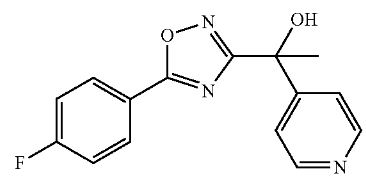 | 1-[5-(4-Fluoro-phenyl)-[1,2,4]oxadiazol-3-yl]-1-pyridin-4-yl-ethanol | 285.09 | 286.2 | 4.92 |
| 30 | 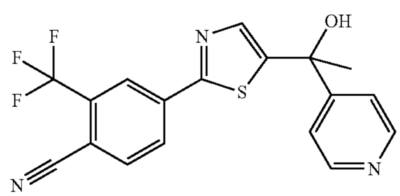 [SMILES: CC(O)(c1ccncc1)c1cnc(-c2ccc(C#N)c(C(F)(F)F)c2)s1] | 4-[5-(1-Hydroxy-1-pyridin-4-yl-ethyl)-thiazol-2-yl]-2-trifluoromethyl-benzonitrile | 375.07 | 375.7 | 1.32 |
| 31 | 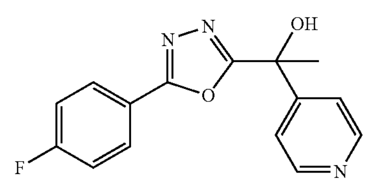 | 1-[5-(4-Fluoro-phenyl)-[1,3,4]oxadiazol-2-yl]-1-pyridin-4-yl-ethanol | 285.09 | 286.1 | 4.45 |
| 32 | 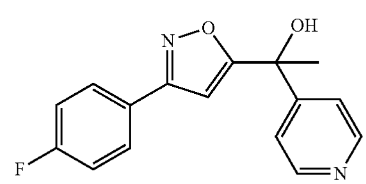 | 1-[3-(4-Fluoro-phenyl)-isoxazol-5-yl]-1-pyridin-4-yl-ethanol | 284.10 | 285.1 | 5.11 |
| 33 | 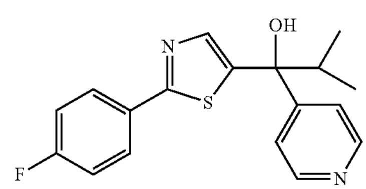 [SMILES: CC(C)C(O)(c1ccncc1)c1cnc(-c2ccc(F)cc2)s1] | 1-[2-(4-Fluoro-phenyl)-thiazol-5-yl]-2-methyl-1-pyridin-4-yl-propan-1-ol | 328.10 | 329.1 | 5.75 |
| 34 | 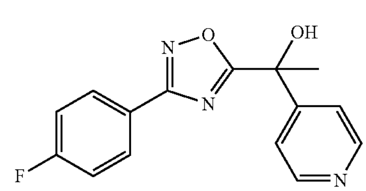 | 1-(3-(4-Fluorophenyl)-1,2,4-oxadiazol-5-yl)-1-(pyridin-4-yl)ethanol | 285.09 | 286.1 | 5.18 |

TABLE 2-continued

| Ex. | Structure | Name | Exact mass | LC-MS [M + H]+ (m/z) | LC-MS retention time (min) |
|---|---|---|---|---|---|
| 35 | 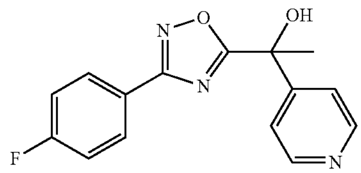 [SMILES: CC(O)(c1ccncc1)c1nc(-c2ccc(F)cc2)no1] | 1-(3-(4-Fluorophenyl)-1,2,4-oxadiazol-5-yl)-1-(pyridin-4-yl)ethanol (enantiomer #1) | 285.09 | 286.1 | 2.36 |
| 36 | 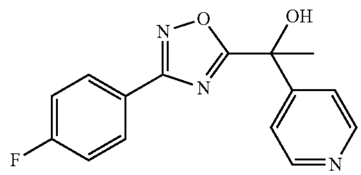 | 1-(3-(4-Fluorophenyl)-1,2,4-oxadiazol-5-yl)-1-(pyridin-4-yl)ethanol (enantiomer #2) | 285.09 | 286.7 | 2.31 |
| 37 | 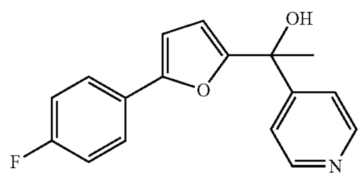 | 1-(5-(4-fluorophenyl)furan-2-yl)-1-(pyridin-4-yl)ethanol | 283.10 | 284.1 | 1.27 |
| 38 | 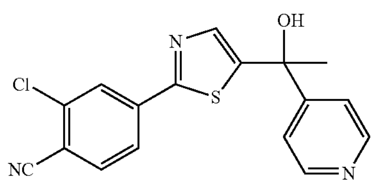 [SMILES: CC(O)(c1ccncc1)c1cnc(-c2ccc(C#N)c(Cl)c2)s1] | 2-chloro-4-(5-(1-hydroxy-1-(pyridin-4-yl)ethyl)thiazol-2-yl)benzonitrile | 341.04 | 342.1 | 5.42 |
| 39 | 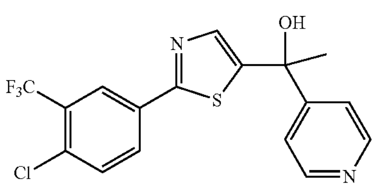 [SMILES: CC(O)(c1ccncc1)c1cnc(-c2ccc(Cl)c(C(F)(F)F)c2)s1] | 1-(2-(4-chloro-3-(trifluoromethyl)phenyl)thiazol-5-yl)-1-(pyridin-4-yl)ethanol | 384.03 | 385.1 | 1.62 |
| 40 | 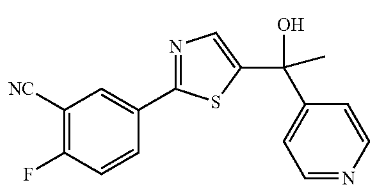 [SMILES: CC(O)(c1ccncc1)c1cnc(-c2ccc(F)c(C#N)c2)s1] | 2-fluoro-5-(5-(1-hydroxy-1-(pyridin-4-yl)ethyl)thiazol-2-yl)benzonitrile | 325.07 | 326.6 | 1.30 |
| 41 | 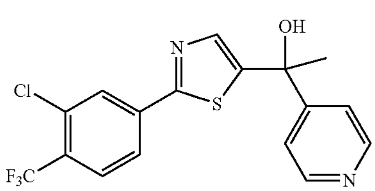 [SMILES: CC(O)(c1ccncc1)c1cnc(-c2ccc(C(F)(F)F)c(Cl)c2)s1] | 1-(2-(3-chloro-4-(trifluoromethyl)phenyl)thiazol-5-yl)-1-(pyridin-4-yl)ethanol | 384.03 | 385.6 | 1.60 |
| 42 | 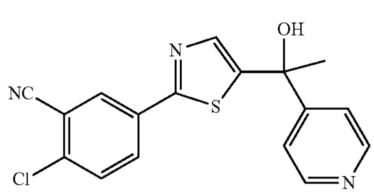 [SMILES: CC(O)(c1ccncc1)c1cnc(-c2ccc(Cl)c(C#N)c2)s1] | 2-chloro-5-(5-(1-hydroxy-1-(pyridin-4-yl)ethyl)thiazol-2-yl)benzonitrile | 341.04 | 342.5 | 1.15 |

TABLE 2-continued

| Ex. | Structure | Name | Exact mass | LC-MS [M + H]+ (m/z) | LC-MS retention time (min) |
|---|---|---|---|---|---|
| 43 | 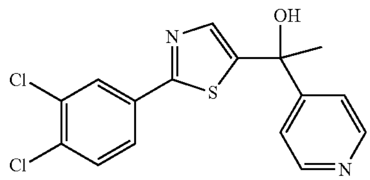 [SMILES: CC(O)(c1ccncc1)c1cnc(-c2ccc(Cl)c(Cl)c2)s1] | 1-(2-(3,4-dichlorophenyl)thiazol-5-yl)-1-(pyridin-4-yl)ethanol | 350.00 | 351.3 | 1.47 |
| 44 | 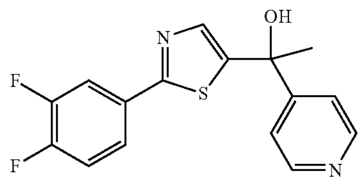 [SMILES: CC(O)(c1ccncc1)c1cnc(-c2ccc(F)c(F)c2)s1] | 1-(2-(3,4-difluorophenyl)thiazol-5-yl)-1-(pyridin-4-yl)ethanol | 318.06 | 319.1 | 5.39 |
| 45 | 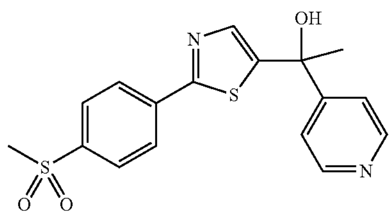 [SMILES: CC(O)(c1ccncc1)c1cnc(-c2ccc(S(C)(=O)=O)cc2)s1] | 1-(2-(4-(methylsulfonyl)phenyl)thiazol-5-yl)-1-(pyridin-4-yl)ethanol | 360.06 | 361.1 | 1.36 |
| 46 | 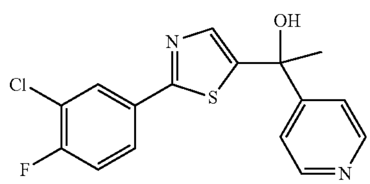 | 1-(2-(3-chloro-4-fluorophenyl)thiazol-5-yl)-1-(pyridin-4-yl)ethanol | 334.03 | 335.1 | 3.01 |
| 47 | 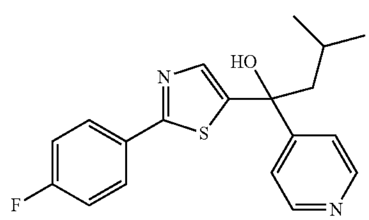 [SMILES: CC(C)CC(O)(c1ccncc1)c1cnc(-c2ccc(F)cc2)s1] | 1-(2-(4-fluorophenyl)thiazol-5-yl)-3-methyl-1-(pyridin-4-yl)butan-1-ol | 342.12 | 343.1 | 6.08 |
| 48 | 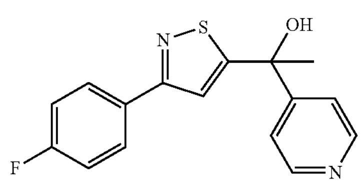 | 1-(3-(4-fluorophenyl)isothiazol-5-yl)-1-(pyridin-4-yl)ethanol | 300.07 | 301.1 | 5.45 |
| 49 | 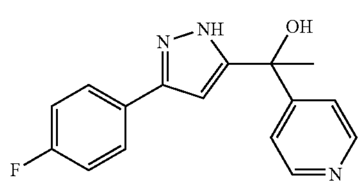 [SMILES: CC(O)(c1ccncc1)c1cc(-c2ccc(F)cc2)ns1] | 1-(3-(4-fluorophenyl)-1H-pyrazol-5-yl)-1-(pyridin-4-yl)ethanol | 283.11 | 285.1 | 4.64 |
| 50 | 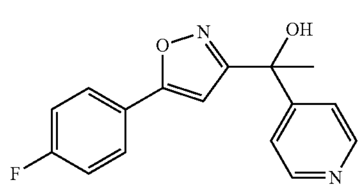 [SMILES: CC(O)(c1ccncc1)c1cc(-c2ccc(F)cc2)on1] | 1-(5-(4-fluorophenyl)isoxazol-3-yl)-1-(pyridin-4-yl)ethanol | 284.10 | 285.1 | 5.21 |

TABLE 2-continued

| Ex. | Structure | Name | Exact mass | LC-MS [M + H]+ (m/z) | LC-MS retention time (min) |
|---|---|---|---|---|---|
| 51 | 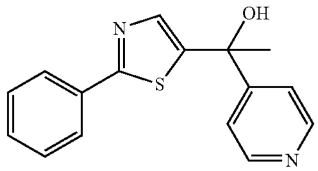 [SMILES: CC(O)(c1ccncc1)c1cnc(-c2ccccc2)s1] | 1-(2-phenylthiazol-5-yl)-1-(pyridin-4-yl)ethanol | 282.08 | 283.1 | 5.02 |
| 52 | 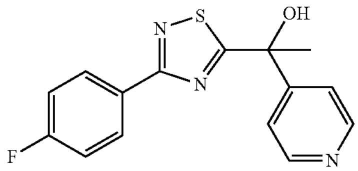 | 1-(3-(4-fluorophenyl)-1,2,4-thiadiazol-5-yl)-1-(pyridin-4-yl)ethanol | 301.07 | 302.9 | 5.75 |
| 53 | 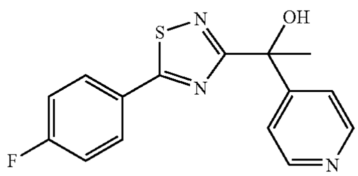 | 1-(5-(4-fluorophenyl)-1,2,4-thiadiazol-3-yl)-1-(pyridin-4-yl)ethanol | 301.07 | 302.1 | 5.24 |
| 54 | 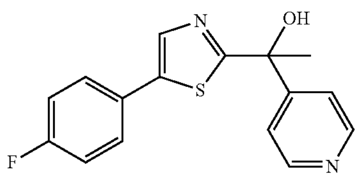 | 1-(5-(4-fluorophenyl)thiazol-2-yl)-1-(pyridin-4-yl)ethanol (enantiomer #1) | 300.07 | 301.1 | 1.65 |
| 55 | 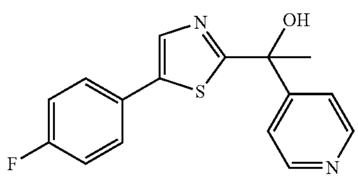 | 1-(5-(4-fluorophenyl)thiazol-2-yl)-1-(pyridin-4-yl)ethanol (enantiomer #2) | 300.07 | 301.1 | 1.63 |
| 56 | 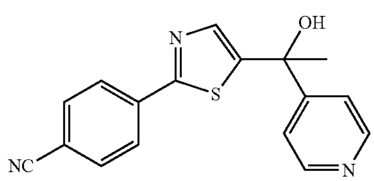 [SMILES: CC(O)(c1ccncc1)c1cnc(-c2ccc(C#N)cc2)s1] | 4-(5-(1-hydroxy-1-(pyridin-4-yl)ethyl)thiazol-2-yl)benzonitrile | 307.08 | 308.5 | 1.57 |
| 57 | 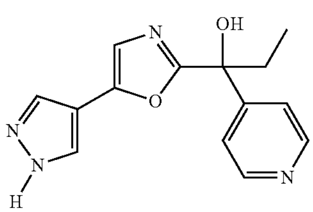 [SMILES: CCC(O)(c1ccncc1)c1ncc(-c2cn[nH]c2)o1] | 1-(5-(1H-pyrazol-4-yl)oxazol-2-yl)-1-(pyridin-4-yl)propan-1-ol | 270.11 | 271.5 | 1.36 |
| 58 | 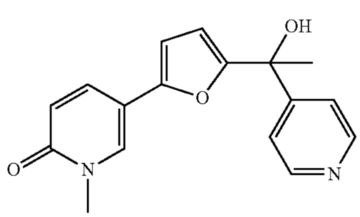 | 5-(5-(1-hydroxy-1-(pyridin-4-yl)ethyl)furan-2-yl)-1-methylpyridin-2(1H)-one | 296.12 | 297.1 | 0.92 |

TABLE 2-continued

| Ex. | Structure | Name | Exact mass | LC-MS [M + H]+ (m/z) | LC-MS retention time (min) |
| --- | --- | --- | --- | --- | --- |
| 59 | 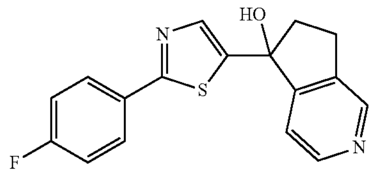 [SMILES: OC1(c2cnc(-c3ccc(F)cc3)s2)CCc2cnccc21] | 5-(2-(4-fluorophenyl)thiazol-5-yl)-6,7-dihydro-5H-cyclopenta[c]pyridin-5-ol | 312.07 | 313.1 | 5.2 |
| 60 | 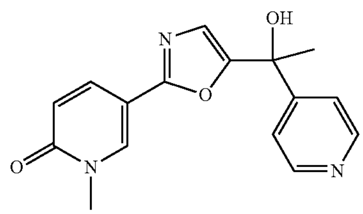 [SMILES: Cn1cc(-c2ncc(C(C)(O)c3ccncc3)o2)ccc1=O] | 5-(5-(1-hydroxy-1-(pyridin-4-yl)ethyl)oxazol-2-yl)-1-methylpyridin-2(1H)-one | 297.11 | 298.1 | 1.30 |
| 61 | 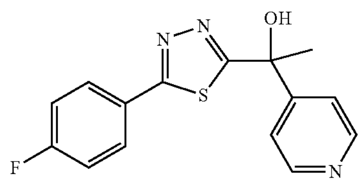 [SMILES: CC(O)(c1ccncc1)c1nnc(-c2ccc(F)cc2)s1] | 1-(5-(4-fluorophenyl)-1,3,4-thiadiazol-2-yl)-1-(pyridin-4-yl)ethanol | 301.07 | 302.1 | 1.99 |
| 62 | 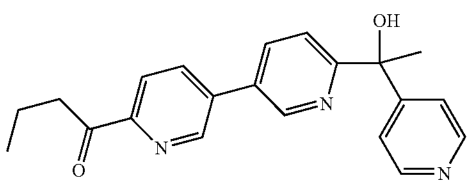 [SMILES: CCCC(=O)c1ccc(-c2ccc(C(C)(O)c3ccncc3)nc2)cn1] | 1-(6'-(1-hydroxy-1-(pyridin-4-yl)ethyl)-[3,3'-bipyridin]-6-yl)pentan-1-one | 361.18 | 362.2 | 2.42 |
| 63 | 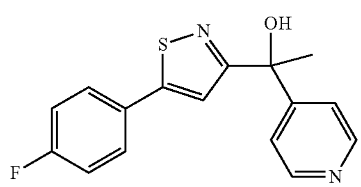 [SMILES: CC(O)(c1ccncc1)c1cc(-c2ccc(F)cc2)sn1] | 1-(5-(4-fluorophenyl)isothiazol-3-yl)-1-(pyridin-4-yl)ethanol | 300.07 | 301.5 | 1.43 |
| 64 | 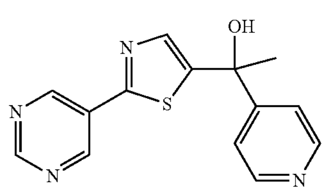 [SMILES: CC(O)(c1ccncc1)c1cnc(-c2cncnc2)s1] | 1-(pyridin-4-yl)-1-(2-(pyrimidin-5-yl)thiazol-5-yl)ethanol | 284.07 | 285.0 | 1.08 |

TABLE 2-continued

| Ex. | Structure | Name | Exact mass | LC-MS [M + H]+ (m/z) | LC-MS retention time (min) |
|---|---|---|---|---|---|
| 65 | 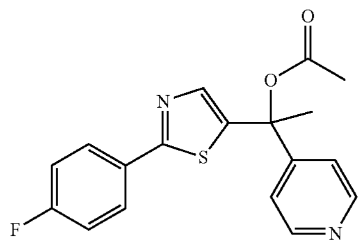 [SMILES: CC(=O)OC(C)(c1ccncc1)c1cnc(-c2ccc(F)cc2)s1] | 1-(2-(4-fluorophenyl)thiazol-5-yl)-1-(pyridin-4-yl)ethyl acetate | 342.08 | 343.1 | 2.43 |
| 66 | 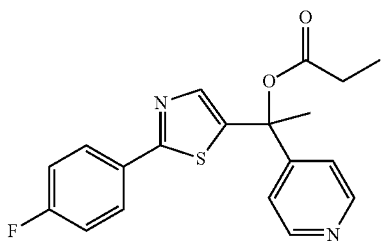 [SMILES: CCC(=O)OC(C)(c1ccncc1)c1cnc(-c2ccc(F)cc2)s1] | 1-(2-(4-fluorophenyl)thiazol-5-yl)-1-(pyridin-4-yl)ethyl propionate | 356.10 | 357.2 | 4.94 |
| 67 | 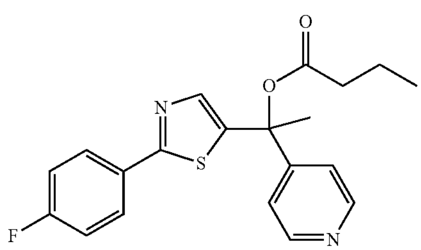 [SMILES: CCCC(=O)OC(C)(c1ccncc1)c1cnc(-c2ccc(F)cc2)s1] | 1-(2-(4-fluorophenyl)thiazol-5-yl)-1-(pyridin-4-yl)ethyl butyrate | 370.12 | 371.2 | 5.31 |
| 68 | 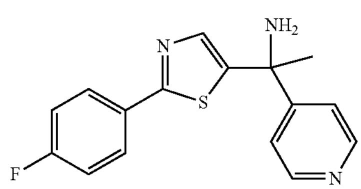 [SMILES: CC(N)(c1ccncc1)c1cnc(-c2ccc(F)cc2)s1] | 1-(2-(4-fluorophenyl)thiazol-5-yl)-1-(pyridin-4-yl)ethanamine | 299.09 | 300.1 | 4.26 |
| 69 | 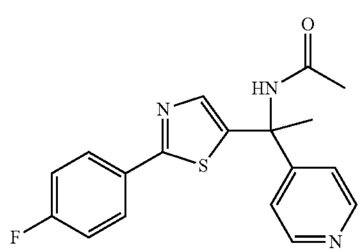 [SMILES: CC(=O)NC(C)(c1ccncc1)c1cnc(-c2ccc(F)cc2)s1] | N-(1-(2-(4-fluorophenyl)thiazol-5-yl)-1-(pyridin-4-yl)ethyl)acetamide | 341.10 | 342.1 | 1.05 |

Examples 70-83

The following compounds are prepared using the procedures discussed in Schemes 1-19 and Examples 1-69 noted above:

a) 4-(5-(1-hydroxy-1-(pyridin-4-yl)ethyl)thiazol-2-yl)-1H-pyrrole-2-carbonitrile

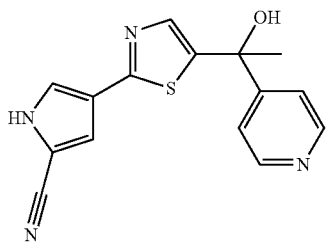

b) 4-(5-(1-hydroxy-1-(pyridin-4-yl)propyl)thiazol-2-yl)-1H-pyrrole-2-carbonitrile

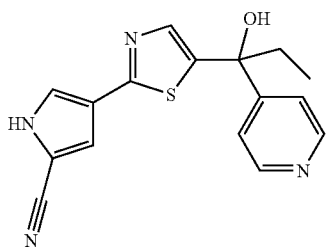 [SMILES: CCC(O)(c1ccncc1)c1cnc(-c2c[nH]c(C#N)c2)s1]

c) 4-(5-(1-hydroxy-1-(pyridin-4-yl)ethyl)-1,3,4-thiadiazol-2-yl)-1H-pyrrole-2-carbonitrile

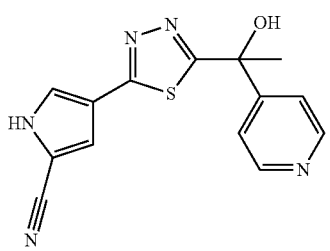 [SMILES: CC(O)(c1ccncc1)c1nnc(-c2c[nH]c(C#N)c2)s1]

d) 4-(5-(1-hydroxy-1-(pyridin-4-yl)ethyl)-1,2,4-oxadiazol-3-yl)-1H-pyrrole-2-carbonitrile

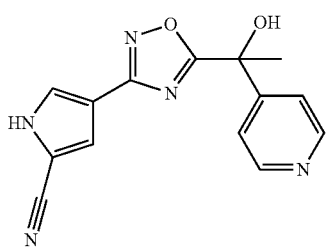 [SMILES: CC(O)(c1ccncc1)c1nc(-c2c[nH]c(C#N)c2)no1]

e) 4-(5-(1-amino-1-(pyridin-4-yl)ethyl)thiazol-2-yl)-1H-pyrrole-2-carbonitrile

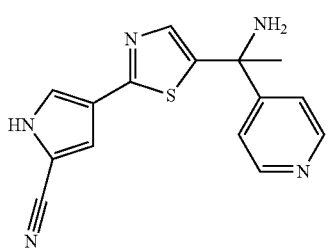 [SMILES: CC(N)(c1ccncc1)c1cnc(-c2c[nH]c(C#N)c2)s1]

f) 1-(2-(4-fluorophenyl)thiazol-5-yl)-1-(pyridin-4-yl)ethanamine

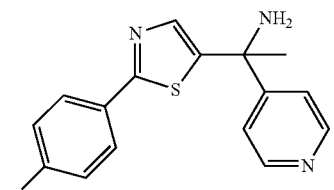

g) 1-(2-(4-fluorophenyl)thiazol-5-yl)-1-(pyridin-4-yl)propan-1-amine

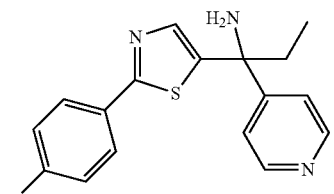

h) 1-(3-(4-fluorophenyl)-1,2,4-oxadiazol-5-yl)-1-(pyridin-4-yl)ethanamine

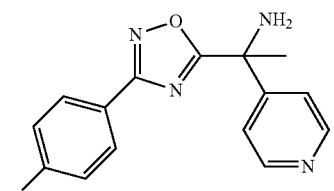

i) 1-(2-(3-chloro-4-fluorophenyl)thiazol-5-yl)-1-(pyridin-4-yl)ethanamine

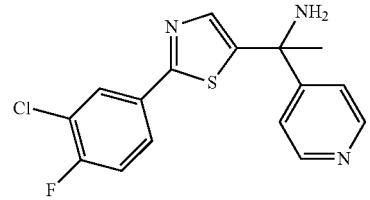 [SMILES: CC(N)(c1ccncc1)c1cnc(-c2ccc(F)c(Cl)c2)s1]

j) 1-(5-(4-fluorophenyl)pyridin-2-yl)-1-(pyridin-4-yl)ethanamine

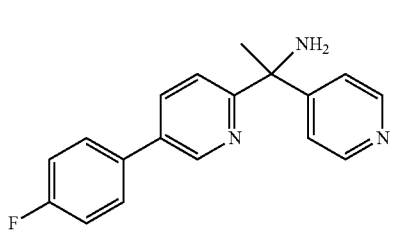 [SMILES: CC(N)(c1ccncc1)c1ccc(-c2ccc(F)cc2)cn1]

k) 5-(5-(1-amino-1-(pyridin-4-yl)ethyl)thiophen-2-yl)-1-methylpyridin-2(1H)-one

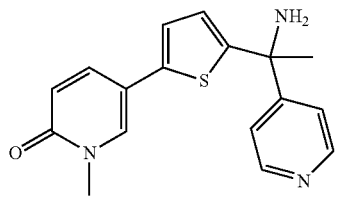 [SMILES: Cn1cc(-c2ccc(C(C)(N)c3ccncc3)s2)ccc1=O]

l) 1-(2-(1H-pyrazol-4-yl)thiazol-5-yl)-1-(pyridin-4-yl)propan-1-amine

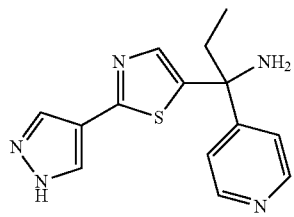 [SMILES: CCC(N)(c1ccncc1)c1cnc(-c2cn[nH]c2)s1]

m) 1-(2-(5-cyano-1H-pyrrol-3-yl)thiazol-5-yl)-1-(pyridin-4-yl)ethyl acetate

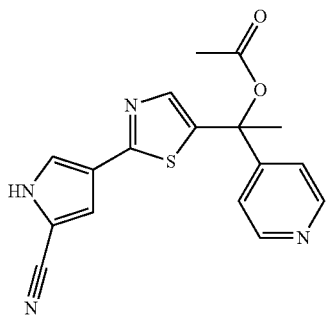 [SMILES: CC(=O)OC(C)(c1ccncc1)c1cnc(-c2c[nH]c(C#N)c2)s1]

n) N-(1-(3-(4-fluorophenyl)-1,2,4-oxadiazol-5-yl)-1-(pyridin-4-yl)ethyl)acetamide

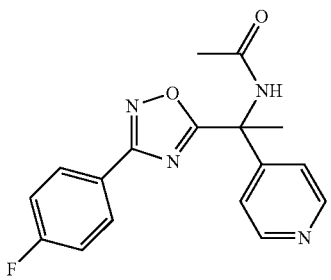 [SMILES: CC(=O)NC(C)(c1ccncc1)c1nc(-c2ccc(F)cc2)no1]

Example 84

CYP17 Inhibition Assay in Rat Testicular Microsomes (Rat CYP17) or Yeast Microsome Overexpressing human CYP17

A. Materials

1. NADPH (Sigma): A working stock was prepared by adding 25 µL of 6.5 mM NADPH in each tube. The final concentration of NADPH used in the assay was 325 µM.

2. Potassium Phosphate Buffer: One molar (1M) solutions of $K_2HPO_4$ and $KH_2PO_4$ were prepared. Eight mL of the 1 M $KH_2PO_4$ and 1.98 mL of the 1 M $K_2HPO_4$ were combined and the pH was adjusted to 7.4.

3. $^3H_3$-17α-hydroxypregnenolone (American Radiolabeled Chemicals, Inc., stock 1 µCi/µL): A 1:1 dilution of $^3H_3$-17α-hydroxypregnenolone in ethanol was prepared by combining 100 µL $^3H_3$-17α-hydroxypregnenolone+100 µL ethanol for one complete 96 well plate. For the reaction, 2 µL of the diluted $^3H_3$-17α-hydroxypregnenolone was added in each tube, i.e., 1 µCi/reaction.

4. Microsome Isolation Buffer: The microsome isolation buffer was prepared by combining 250 mM Sucrose, 5 mM EDTA, 10 mM Tris HCl, 4 mM DTT, and adjusting to pH 7.4.

5. TEG Buffer: The TEG buffer was prepared by combining 50 mM Tris HCl, 1 mM EDTA, and 20% Glycerol.

6. Rat Testicular Microsomes: Rat testis tissue was collected and disrupted with 30 strokes of a glass homogenizer on ice with 250 µL of microsome isolation buffer, followed by centrifugation at 10,000 g for 10 minutes at 4° C. The supernatant was collected and centrifuged at 100,000 g for 45 minutes at 4° C. The pellet was dissolved in TEG Buffer and the protein was quantified. The homogenized microsome samples were then frozen at −80° C.

7. Yeast Microsomes which overexpress the human CYP17 enzyme were obtained from Premas Biotech, India.

B. Procedure

Potassium phosphate buffer (470 µL) was prepared as described above and was added to each well of a deep well plate. The test compound was diluted using a TECAN liquid handler and 5 µL of diluted compound was transferred to each well (96 deep well/1 mL). A solution (25 µL) of 6.5 mM NADPH was added (final concentration of 325 µM in the assay). $^3H_3$-17α-hydroxypregnenolone (2 µL of the working stock) was added to each tube. The plates were then pre-incubated for 15 minutes at 37° C. Following the pre-incubation, either 5 µL rat testicular microsomes (150-160 µg) or 5 µL of yeast microsomes expressing human CYP17 (1.7 pmol), was added. Incubation was at 37° C. for 60 minutes in the presence of oxygen. The plates were then placed in ice and chloroform (500 µL) was added, mixed well and incubated at 4° C. for 20 minutes. The plates were then centrifuged at 1000 rpm for 15 minutes at 4° C.

A portion (300 µL) of the aqueous solution was collected and mixed with a 5% aqueous suspension of activated charcoal (300 µL). The plates were then incubated at 4° C. for 30 minutes, after which the plates were centrifuged at 1000 rpm for 15 minutes at 4° C. From this, 125 µL of the aqueous solution was collected and plated into a 96 well plate. Microscint™ 40 [125 µL, Perkin-Elmer; containing a mixture of a polymer based on alkylphenolethoxylate (20-40%), diethanolamine-phosphoric acid ester ammonium salt (10-20%), sodium dioctyl sulphosuccinate (2.5-10%), triethyl phosphate (2.5-10%), 3,6-dimethyl-4-octyne-3,6-diol (<2.5%), a polymer based on nonylphenolethoxylate (<2.5%), diisopropyl naphthalene isomers (40-60%), 2,5-diphenyloxazole (<2.5%), and 9,10-dimethylanthracene] was added and mixed well. After 30 minutes of incubation, the samples were analyzed with a MicroBeta® Trilux microplate liquid scintillation counter and luminometer (Perkin-Elmer).

Compounds of formula (I) caused inhibition of rat microsomal CYP17 and recombinant human CYP17 enzyme activity as determined by these assays. Data are listed in Table 3.

Example 85

Cell-Based Human CYP17 Inhibition Assay

A. Materials

1. H295R Adrenocortical Carcinoma Cells and Growth Media: The media for the H295R Adrenocortical carcinoma cells [NCI-H295A, ATCC Number CRL-2128, American Type Culture Collection, Manassas, Va., US] (500 mL) was a DMEM:F12 Mix 1:1 with 5% (2 mL) BD Nu Serum; 1% (5 mL) ITS+Premix [BD Biosciences] and 1% Penstrep.

2. LNCap-CYP17 Cells and Growth Media: Full length hCYP17a1 gene (NCBI Reference Sequence: NM_000102.3) was cloned in pcDNA3.1(+) vector between HindIII and XhoI site. The pcDNA3.1(+) vector contains the Neomycin resistance gene and was used for selection of stable cell line. The hCYP17a1 containing pcDNA3.1(+) was transfected into LNCap cells to create the LNCap-CYP17 cell line. The media for the LNCaP-CYP17 cells was RPMI 1640, 10% FBS, 1% PenStrep, Geneticin 400 µg/mL.

B. Procedure

The H295R cells or LNCaP-hCYP17 cells were subcultured and 30,000 cells per well were seeded in a poly-d lysine plate and incubated overnight at 37° C. The next day the media was removed and 200 µL of fresh media with $^3H_3$-17α-hydroxypregnenolone (1:1000) was added. 50 µL of serially diluted compounds from a 5× plate (5 times the final desired concentration) was added. The working concentration range for active, new compounds started from a high concentration of 10 µM with 3-fold serial dilutions generating up to 10 concentrations. The serial dilution in the 100× plate (in DMSO) and the stamping of a 5× plate (in media) from the 100× plate were carried out using a TECAN liquid handling device.

The plates were incubated overnight (16 hours) at 37° C. After 16 hours, the media was removed (approximately 220 µL) and an equal amount of chloroform was added, mixed and incubated for 30 minutes at 4 degrees. The plate was centrifuged at 4000 rpm for 15 minutes at 4° C., following which the top aqueous layer was carefully removed and added into a new deep well plate. An equal volume of activated 5% charcoal was added, mixed and incubated for 30 minutes at 4° C. The plate was then centrifuged at 4000 rpm for 15 minutes at 4° C. and the top layer carefully separated, avoiding any charcoal contamination, and placed in a white, clear bottom plate (plate cat #3610, Corning Life Sciences). An equal volume of Microscint™ 40 was added and mixed well. Following the incubation for 30 minutes, readings for the radiotracer were taken using a Microbeta® trilux.

Compounds of formula (I) caused inhibition of human CYP17 enzyme activity as determined by these cell assays. Data are listed in Table 3.

Example 86

Cell-Based Functional Assay for Testosterone Production

H295R cells (ATCC Number CRL-2128) were subcultured, seeded (30,000 cells per well in a poly-d lysine plate) and left overnight at 37° C. The next day (after approximately 24 hours), the media were removed and 200 µL fresh media were added. Then, 50 µL of serially diluted compounds were added from a 5× plate. The serial dilution in the 100× plate (in DMSO) and the stamping of a 5× plate (in media) from the 100× plate were carried out using a TECAN liquid handling device. The plate was incubated at 37° C. for 72 hours. After incubation, the media was removed, diluted 5 to 10 times with calibration diluent RD5-48, and the assay performed as per manufacturer's protocol (Parameter Testosterone Assay, Cat. No. KGE010, R&D systems; http://www.rndsystems.com/pdf/KGE010.pdf).

Compounds of formula (I) caused inhibition of testosterone production in H295R cells as determined by this assay. Data are listed in Table 3.

Example 87

In vivo Inhibition of Testosterone Production

Male rats aged 8 to 10 weeks old were dosed orally with compounds at 10 or 30 mg/kg. Blood samples were drawn at 0.5, 3, 8, and 24 hours and were processed to plasma samples. Samples were analyzed for compound levels by LC-MS/MS method and for testosterone levels with an ELISA performed as per manufacturer's protocol (Parameter Testosterone Assay, Cat. No. KGE010, R&D systems; http://www.rndsystems.com/pdf/KGE010.pdf). The serum testosterone level was calculated from standards using GraphPad® Prism software and % inhibition at a given time was calculated by comparing the testosterone level in vehicle control animals at the same time of day.

Compounds of formula (I) decreased serum testosterone levels as determined by this assay protocol. For example, the compound of Example 14 decreased serum testosterone levels 60-80% at 3-8 hours after a 30 mg/kg oral dose compared to vehicle-dosed control animals sampled at the same time of day. The compound of Example 7 decreased serum testosterone levels 70-85% at 3-8 hours after a 10 mg/kg oral dose compared to vehicle-dosed control animals sampled at the same time of day. The compound of Example 17 decreased serum testosterone levels 30-60% at 3-8 hours after a 30 mg/kg oral dose compared to vehicle-dosed control animals sampled at the same time of day. The dosing formulations used were 5% hydroxy propyl-β-cyclodextrin in 30 mM methane sulfonic acid solution (v/v) for Example 7, and Tween-80™ reagent, 0.5% methyl cellulose for Examples 14 and 17. In one study, the compounds of Examples 17, 34 and 36 decreased serum testosterone levels about 85-95% at 3 hours after a 30 mg/kg oral dose compared to vehicle-dosed control animals sampled at the same time of day.

Example 88

In Vivo Reduction of Prostate and Seminal Vesicle Weights

Male rats aged 8 to 10 weeks old (5 animals per group) were dosed orally with compounds once or twice a day at 12-hour intervals for 14 days. On day 14 the animals were euthanized and organs were surgically removed for wet weight determination including the prostate, seminal vesicles and testes.

Compounds of formula (I) decreased prostate and seminal vesicle weights as determined by this assay protocol. For example, the compounds of Examples 7 and 9, when dosed at 10 mg/kg orally twice a day for 14 days, reduced prostate weights by 20 to 30% and reduced seminal vesicle weights by 30 to 50%. The compound of Example 7, when dosed at 30 mg/kg orally once a day for 14 days, reduced prostate weight by about 50% and seminal vesicle weights by about 60%. The dosing formulation used was 5% hydroxy propyl-β-cyclodextrin in 30 mM methane sulfonic acid solution (v/v). The compounds of Examples 17, 34 and 36, when dosed at 30 mg/kg orally twice a day for 14 days, reduced prostate weight by about 50% and seminal vesicle weights by about 50-70%.

TABLE 3

| Ex. | CYP17 (rat testicular microsomes) | CYP17 (human, yeast microsomes) | CYP17 (human H295R adrenal cells) | CYP17 (human LNCap-CYP17 cells) | Testosterone (human H295R adrenal cells) |
|---|---|---|---|---|---|
| 1 | A | C | B | C | B |
| 2 | A |   | B |   | B |
| 3 | B |   | C |   | B |
| 4 | A |   | B |   | A |
| 5 | A |   | C |   |   |
| 6 | A |   | B |   |   |
| 7 | A | B | B |   | A |
| 8 | A | C | C |   | B |
| 9 | A | B | A |   | A |
| 10 | A |   | C |   |   |
| 11 | A |   | C |   |   |
| 12 | A |   | B |   |   |
| 13 | A |   | C |   |   |
| 14 | A |   | A |   |   |
| 15 | A | C | B |   |   |
| 16 | B |   | B |   |   |
| 17 | A | B | A |   |   |
| 18 | A |   | A |   |   |
| 19 | A |   | A |   |   |
| 20 | C |   |   |   |   |
| 21 | A |   | C |   |   |
| 22 | C |   |   |   |   |
| 23 | A |   | C |   |   |
| 24 | A |   | B |   |   |
| 25 | A |   | C |   |   |
| 26 | A |   | B |   |   |
| 27 | A |   | A |   |   |
| 28 | A |   | A |   |   |
| 29 | A |   | C |   |   |
| 30 | A |   | B |   |   |
| 31 | B |   | C |   |   |
| 32 | A |   | B |   |   |
| 33 | A |   | A |   |   |
| 34 | A |   | A |   |   |
| 35 | A |   | C |   |   |
| 36 | A | A | A |   |   |
| 37 | B |   | B |   |   |
| 38 | A |   | B |   |   |
| 39 | A |   | B |   |   |
| 40 | A |   | A |   |   |
| 41 | A |   | A |   |   |
| 42 | A |   | A |   |   |
| 43 | A |   | A |   |   |
| 44 | A |   | A |   |   |
| 45 | B |   | C |   |   |
| 46 | A |   | A |   |   |
| 47 | A |   | A |   |   |
| 48 | A |   | A |   |   |
| 49 | A |   | C |   |   |
| 50 | A |   | B |   |   |
| 51 | A |   | A |   |   |
| 52 | A |   | A |   |   |
| 53 | B |   | C |   |   |
| 54 | A |   | A |   |   |
| 55 | A |   | B |   |   |
| 56 | A |   | B |   |   |
| 57 | B |   | C |   |   |
| 58 | B |   | C |   |   |
| 59 | B |   | C |   |   |
| 60 | C |   | C |   |   |
| 61 | A |   | B |   |   |
| 62 | B |   | C |   |   |
| 63 | A |   | A |   |   |
| 64 | A |   | C |   |   |
| 65 | A |   |   |   |   |
| 66 | A |   |   |   |   |
| 67 | A |   |   |   |   |
| 68 | A |   | B |   |   |
| 69 | B |   | C |   |   |

Activities (nM):

A: $IC_{50} < 50$;

B: $IC_{50} = 50\text{-}200$;

C: $IC_{50} = 201\text{-}10000$.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. 1-(2-(4-Fluorophenyl)-thiazol-5-yl)-1-(pyridin-4-yl)-ethanol, and pharmaceutically acceptable salts and prodrugs thereof.

2. 1-(2-(4-Fluorophenyl)-thiazol-5-yl)-1-(pyridin-4-yl)-ethanol, in the form of an acid salt.

3. The acid salt compound of claim 2, wherein the acid is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic salts.

4. The acid salt compound of claim 3, wherein the acid is selected from the group consisting of hydrochloric, 4-methylbenzene sulfonic, benzene sulfonic, methanesulfonic, sulfuric and nitric acids.

5. A pharmaceutical composition comprising 1-(2-(4-fluorophenyl)-thiazol-5-yl)-1-(pyridin-4-yl)-ethanol or a pharmaceutically acceptable salt or prodrug thereof, and a pharmaceutically acceptable carrier.

6. The pharmaceutical composition of claim 5, comprising 1-(2-(4-fluorophenyl)-thiazol-5-yl)-1-(pyridin-4-yl)-ethanol in the form of an acid salt, and a pharmaceutically acceptable carrier.

7. The pharmaceutical composition of claim 6, wherein the acid is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic salts.

8. The pharmaceutical composition of claim 7, wherein the acid is selected from the group consisting of hydrochloric, 4-methylbenzene sulfonic, benzene sulfonic, methanesulfonic, sulfuric and nitric acids.

9. 1-(2-(4-Fluorophenyl)-thiazol-5-yl)-1-(pyridin-4-yl)-ethanol.

10. A pharmaceutical composition comprising 1-(2-(4-fluorophenyl)-thiazol-5-yl)-1-(pyridin-4-yl)-ethanol of claim 9, and a pharmaceutically acceptable carrier.

* * * * *